(12) United States Patent
Granger et al.

(10) Patent No.: US 12,354,753 B2
(45) Date of Patent: *Jul. 8, 2025

(54) METHOD AND USES OF DIAGNOSING AND RECOMMENDING TREATMENT FOR A PSYCHOTIC DISORDER

(71) Applicant: Cambridge Cognition Limited, Cambridge (GB)

(72) Inventors: Kiri Granger, Kilby (GB); Jennifer Barnett, Burwell (GB)

(73) Assignee: Cambridge Cognition Limited, Cambridge (GB)

( * ) Notice: Subject to any disclaimer, the term of this patent is extended or adjusted under 35 U.S.C. 154(b) by 64 days.

This patent is subject to a terminal disclaimer.

(21) Appl. No.: 18/514,845

(22) Filed: Nov. 20, 2023

(65) Prior Publication Data
US 2024/0087749 A1 Mar. 14, 2024

Related U.S. Application Data

(63) Continuation of application No. 16/824,067, filed on Mar. 19, 2020, now Pat. No. 11,862,337.
(Continued)

(51) Int. Cl.
*G06Q 50/00* (2024.01)
*A61B 5/00* (2006.01)
(Continued)

(52) U.S. Cl.
CPC ............ *G16H 50/20* (2018.01); *A61B 5/162* (2013.01); *A61B 5/165* (2013.01); *A61B 5/4088* (2013.01);
(Continued)

(58) Field of Classification Search
CPC ........ G16H 20/10; G16H 40/20; G06Q 30/06; G06Q 40/08; G06Q 50/22
(Continued)

(56) References Cited

U.S. PATENT DOCUMENTS

| 6,187,752 B1 | 2/2001 | Sudilovsky et al. |
| 7,163,513 B2 | 1/2007 | Darby et al. |

(Continued)

FOREIGN PATENT DOCUMENTS

| JP | 2018-130454 A | 8/2018 |
| WO | WO 2001/040261 A1 | 6/2001 |
| WO | WO 2013/057687 A2 | 4/2013 |

OTHER PUBLICATIONS

Granger, Enhanced latent inhibition in high schizotypy individuals, 2016, Personality and Individual Differences, vol. 91, March, pp. 31-39 (Year: 2016).*

(Continued)

*Primary Examiner* — Kambiz Abdi
*Assistant Examiner* — Tran N Nguyen
(74) *Attorney, Agent, or Firm* — Klarquist Sparkman, LLP

(57) ABSTRACT

The present specification discloses systems and computer implemented assessment methods including a system and method of assigning an individual to a group participating in a clinical study regarding a psychotic disorder, a system and method of determine whether and what type of psychotic disorder an individual may be suffering from; and a system and method of recommending a therapy to treat an individual with a psychotic disorder. All disclosed systems and computer implemented assessment methods use a noninvasive computational device-based test that uses a graphical user interface to measure a latent inhibition response of an individual to calculate a latent inhibition score and assess working memory. The latent inhibition score determines whether the individual exhibits an attenuated latent inhibition response, a normal latent inhibition response or an enhanced latent inhibition response.

24 Claims, 6 Drawing Sheets

Related U.S. Application Data

(60) Provisional application No. 62/820,490, filed on Mar. 19, 2019.

(51) Int. Cl.

| | |
|---|---|
| *A61B 5/16* | (2006.01) |
| *G16H 10/20* | (2018.01) |
| *G16H 10/60* | (2018.01) |
| *G16H 20/70* | (2018.01) |
| *G16H 50/20* | (2018.01) |
| *G16H 50/50* | (2018.01) |
| *G16H 50/70* | (2018.01) |
| *G06Q 10/00* | (2023.01) |

(52) U.S. Cl.
CPC ........... *A61B 5/4848* (2013.01); *G16H 10/20* (2018.01); *G16H 10/60* (2018.01); *G16H 20/70* (2018.01); *G16H 50/50* (2018.01); *G16H 50/70* (2018.01)

(58) Field of Classification Search
USPC ........................................................ 705/2–3
See application file for complete search history.

(56) References Cited

U.S. PATENT DOCUMENTS

| | | | |
|---|---|---|---|
| 7,816,362 B2 | 10/2010 | Childers et al. | |
| 7,935,500 B2 | 5/2011 | Gerber et al. | |
| 8,334,262 B2 | 12/2012 | Rosenblum et al. | |
| 9,145,372 B2 | 9/2015 | Lowe, III | |
| 9,526,721 B2 | 12/2016 | Miller et al. | |
| 9,605,260 B2 | 3/2017 | Ecker et al. | |
| 9,801,879 B2 | 10/2017 | Lowe, III | |
| 2003/0046114 A1 | 3/2003 | Davies et al. | |
| 2004/0014095 A1 | 1/2004 | Gerber et al. | |
| 2004/0103447 A1 | 5/2004 | Nawa et al. | |
| 2005/0158715 A1 | 7/2005 | Fuchs et al. | |
| 2005/0177065 A1 | 8/2005 | Ghajar | |
| 2006/0210633 A1 | 9/2006 | Dharmadhikari et al. | |
| 2007/0050151 A1 | 3/2007 | Satoh et al. | |
| 2007/0129403 A1 | 6/2007 | Smith et al. | |
| 2008/0206727 A1* | 8/2008 | Ghajar ................... | A61B 5/162 434/258 |
| 2008/0312513 A1 | 12/2008 | Ely et al. | |
| 2009/0287064 A1* | 11/2009 | Dougherty, Jr. ....... | G16H 50/20 600/300 |
| 2011/0020778 A1* | 1/2011 | Forbes ................... | A61B 5/167 434/236 |
| 2011/0136738 A1 | 6/2011 | Murphy et al. | |
| 2012/0094315 A1 | 4/2012 | Fryar-Williams | |
| 2014/0154650 A1 | 6/2014 | Stack | |
| 2015/0275303 A1 | 10/2015 | Feuerbach et al. | |
| 2016/0038463 A1 | 2/2016 | Gallagher et al. | |

OTHER PUBLICATIONS

Barak et al., "Pro-Cognitive and Antipsychotic Efficacy of the a7 Nicotinic Partial Agonist SSR180711 in Pharmacological and Neurodevelopment Latent Inhibition Models of Schizophrenia," *Neuropsychopharmacol.* 34: 1753-1763, 2009.
Braff, Information Processing and Attention Dysfunctions in Schizophrenia, *Schizophrenia Bulletin* 19.2: 233-259, 1993.
Burch et al., "Trials-to-Criterion Latent Inhibition in Humans as a Function of Stimulus Pre-Exposure and Positive-Schizotypy," *Br J Psychol.* 95: 179-196, 2004.
Burch et al., "Personality, Creativity and Latent Inhibition," *Eur J Pers.* 20: 107-122, 2006.
Diaz et al., "Latent Inhibition in Human Affective Learning," *Emotion* 2.3: 242-250, 2002.
Evans et al., "A New Continuous Within-Participants Latent Inhibition Task: Examining Associations with Schizotypy Dimensions, Smoking Status and Gender," *Biol Psychol.* 74: 365-373, 2007.
Frishman, "A historical perspective on the Development of β-adrenergic blockers," *Journal of Clinical Hypertension* 9.4(Suppl. 3): 19-27, Apr. 2007.
Granger et al., "Disruption of Overshadowing and Latent Inhibition in High Schizotypy Individuals," *Behav Brain Res.* 233: 201-208, 2012.
Granger et al., "Enhanced Latent Inhibition in High Schizotypy Individuals," *Personality and Individual Differences* 91: 31-39, 2016.
Gray et al., "Context Dependent Latent Inhibition in Adult Humans," *Q J Exper Psychol.* 54B.3: 233-245, 2001.
Kaplan et al., "Obsessive-Compulsive Disorder Patients Display Enhanced Latent Inhibition on a Visual Search Task," *Behav Res Ther.* 44: 1137-1145, 2006.
Lubow, "Performance on the Visual Search Analog of Latent Inhibition is Modulated by an Interaction Between Schizotypy and Gender," *Schizophren Res.* 52: 275-287, 2001.
Lv, "The Involvement of Working Memory and Inhibition Functions in the Different Phases of Insight Problem Solving," *Mem Cogn.* 43: 709-722, 2015.
Mason and Claridge, "The Oxford-Liverpool inventory of feelings and experiences (O-LIFE): further description and extended norms," *Schizophrenia Research* 82: 203-211, e-PUB Jan. 18, 2006.
Mason et al., "New scales for the assessment of schizotypy," *Personality and Individual Differences* 18.1: 7-13, Jan. 1995.
Schmidt-Hansen et al., "Latent Inhibition, Learned Irrelevance, and Schizotypy: Assessing their Relationship," *Cognitive Neuropsychiatry* 14.1: 11-29, 2009.
Swerdlow et al., "Enhanced Visual Latent Inhibition in Obsessive-Compulsive Disorder," *Biol Psychiatry.* 45: 482-488, 1999.
Wang et al., "High schizotypal individuals are more creative? The medication roles of overinclusive thinking and cognitive inhibition," *Frontiers in Psychology* 9: 1766, Sep. 21, 2018 (14 pages).
Yogev et al., "Latent Inhibition and Overswitching in Schizophrenia," *Schizophrenia Bulletin* 30.4: 713-726, 2004.
Granger, "Dissociating Variations in Attention with Schizotypy and Anxiety," Thesis, University of Nottingham, 2017 (269 pages).
International Search Report and Written Opinion mailed in International Application No. PCT/EP2020/057670 by the European Patent Office as International Searching Authority on Aug. 7, 2020 (13 pages).
Weiner and Arad, "Using the pharmacology of latent inhibition to model domains of pathology in schizophrenia and their treatment," *Behavioural Brain Research* 204:369-386, 2009.

\* cited by examiner

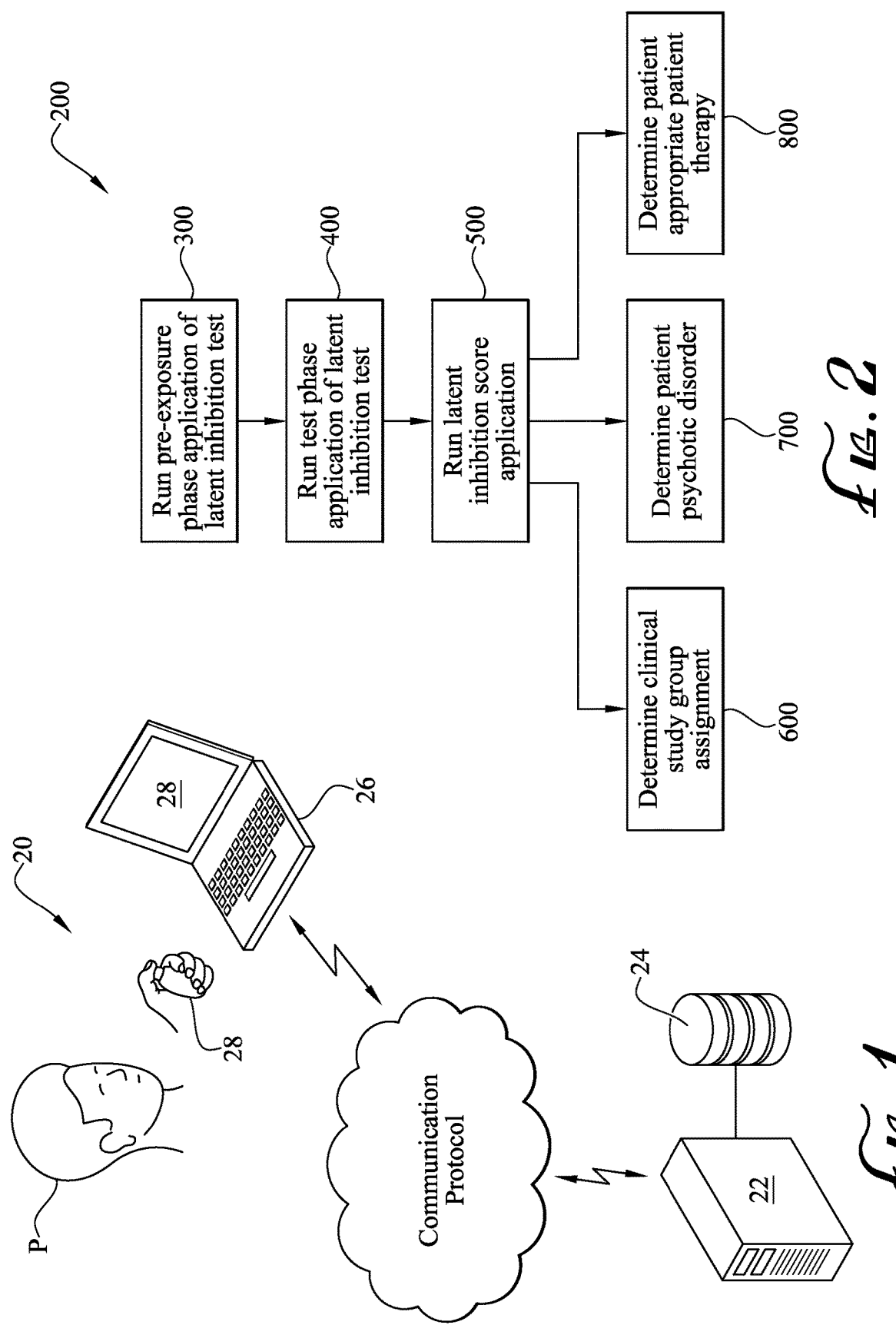

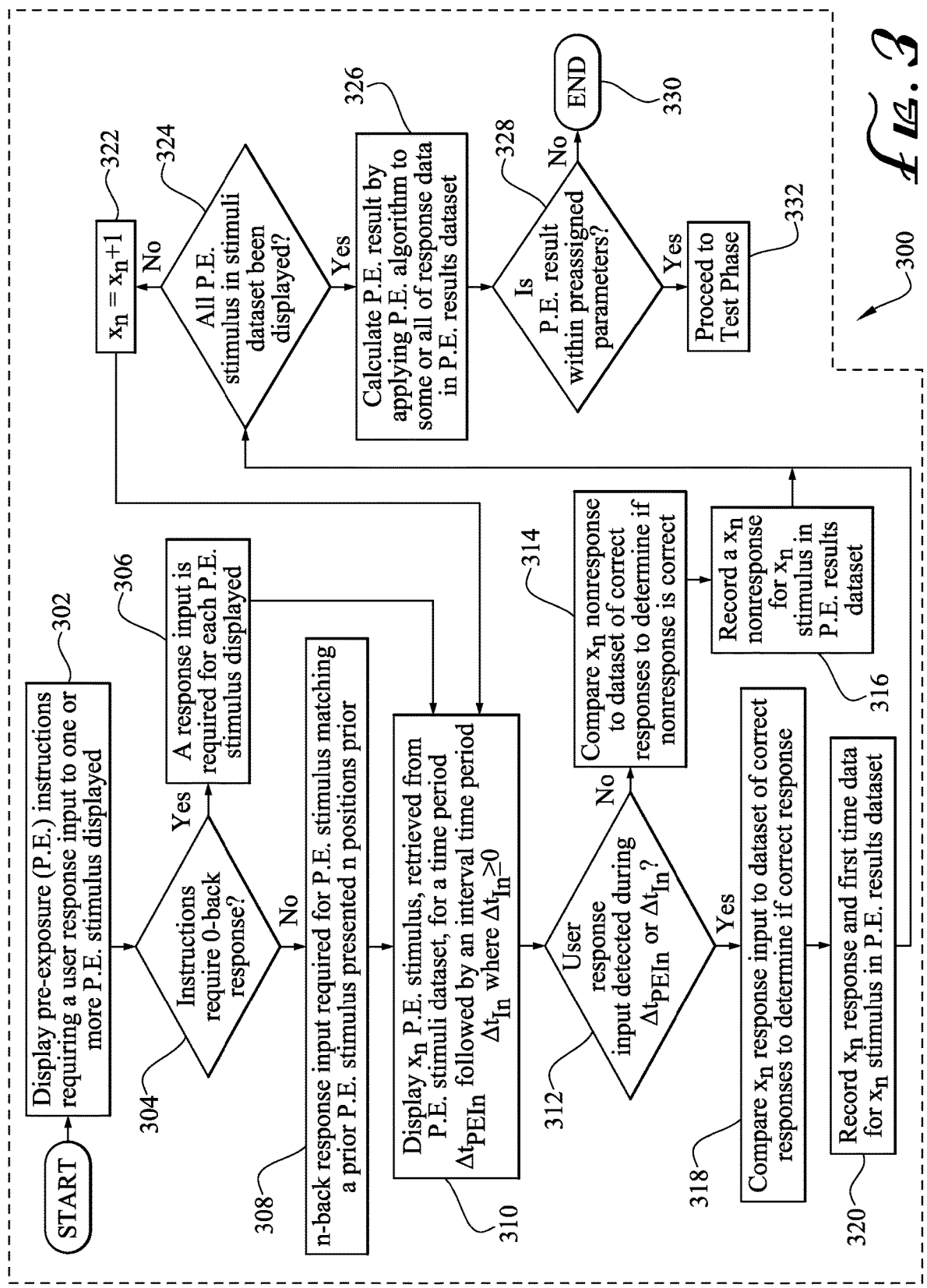

| Patient Situation | Definition | Latent Inhibition | Diagnosis | Therapy Recommendation |
|---|---|---|---|---|
| Case 1. Ultra-High Risk (UHR) | • Do no currently have psychotic symptoms<br>• No history of psychotic disorder<br>• No history of drug resistance | Attenuated | UHR | Treat with APD |
| | | Normal | Non-UHR | Do not treat |
| | | Enhanced | UHR (TRS likely) | Treat with PCD |
| Case 2. First Episode Psychosis (FEP) | • Currently have psychotic symptoms<br>• No history of psychotic disorder<br>• No history of drug resistance | Attenuated | FEP | Treat with APD |
| | | Normal | Non-FEP | Maintain current treatment |
| | | Enhanced | FEP (TRS likely) | Clozapine + PCD |
| Case 3. Chronic Treatment Responsive Schizophrenia (TSR) | • May currently have psychotic symptoms<br>• Diagnosed history of psychotic disorder<br>• No history of drug resistance | Attenuated | Psychotic disorder | Treat with APD + PCD |
| | | Normal | Psychosis absent | Maintain current treatment |
| | | Enhanced | Psychotic disorder | PCD add-on treatment |
| Case 4. Treatment Resistant Schizophrenia (TSR) | • Currently have moderate to sever psychotic symptoms<br>• Diagnosed history of psychotic disorder<br>• History of drug resistance | Attenuated | TRS | Treat with APD + PCD |
| | | Normal | Non-treatment resistant | Maintain current treatment |
| | | Enhanced | TRS | Clozapine + PCD |
| Case 5. Anti-psychotic drug action | • Currently have psychotic symptoms<br>• Diagnosed history of psychotic disorder<br>• Currently taking medication | Attenuated | --- | Increase dose of current medication |
| | | Normal | --- | Maintain current treatment dose |
| | | Enhanced | --- | Decrease dose of current medication |

FIG. 6

| Patient Situation | Definition | Latent Inhibition | Working Memory | Diagnosis | Therapy Recommendation |
|---|---|---|---|---|---|
| Case 1. Ultra-High Risk (UHR) | • Do no currently have psychotic symptoms<br>• No history of psychotic disorder<br>• No history of drug resistance | Attenuated | Deficit | UHR | Treat with APD + PCD |
| | | | No Deficit | Non-UHR | Do not treat |
| | | Normal | Deficit | UHR | Treat with PCD |
| | | | No Deficit | Non-UHR | Do not treat |
| | | Enhanced | Deficit | UHR | Treat with PCD |
| | | | No Deficit | Non-UHR | Do not treat |
| Case 2. First Episode Psychosis (FEP) | • Currently have psychotic symptoms<br>• No history of psychotic disorder<br>• No history of drug resistance | Attenuated | Deficit | FEP | Treat with APD + PCD |
| | | | No Deficit | FEP | Treat with APD |
| | | Normal | Deficit | FEP | Maintain current treatment + PCD |
| | | | No Deficit | Non-FEP | Maintain current treatment |
| | | Enhanced | Deficit | FEP | Clozapine + PCD |
| | | | No Deficit | FEP | Treat with PCD |
| Case 3. Treatment Responsive Schizophrenia (TSR) | • May currently have psychotic symptoms<br>• Diagnosed history of psychotic disorder<br>• No history of drug resistance | Attenuated | Deficit | Psychotic disorder | Treat with APD + PCD |
| | | | No Deficit | Psychotic disorder | Treat with APD |
| | | Normal | Deficit | Psychotic disorder | Maintain current treatment + PCD |
| | | | No Deficit | Psychotic absent | Maintain current treatment |
| | | Enhanced | Deficit | Psychotic disorder | Treat with APD + PCD |
| | | | No Deficit | Psychotic disorder | Treat with PCD |
| Case 4. Treatment Resistant Schizophrenia (TSR) | • Currently have moderate to sever psychotic symptoms<br>• Diagnosed history of psychotic disorder<br>• History of drug resistance | Attenuated | Deficit | TRS | Treat with APD + PCD |
| | | | No Deficit | TRS | Treat with APD |
| | | Normal | Deficit | Non-TRS | Current treatment + PCD |
| | | | No Deficit | Non-TRS | Maintain current treatment |
| | | Enhanced | Deficit | TRS | Clozapine + PCD |
| | | | No Deficit | TRS | Clozapine + PCD |

FIG. 7

METHOD AND USES OF DIAGNOSING AND RECOMMENDING TREATMENT FOR A PSYCHOTIC DISORDER

This application is a continuation of U.S. patent application Ser. No. 16/824,067, filed Mar. 19, 2020, which claims the benefit of priority and the filing date pursuant to 35 U.S.C. § 119(e) to U.S. Provisional Patent Application 62/820,490, filed Mar. 19, 2019, the entire contents of each of which are hereby incorporated by reference in their entireties.

A psychotic disorder is an abnormal condition of the mind characterized by severe mental disruptions that cause abnormal thinking and perceptions in an individual. These disruptions are generally classified into three groups. The first is psychotic symptoms such as hallucinations, where an individual sees, hears and believes things that aren't real, and delusions, where an individual has strange, persistent thoughts, behaviors and emotions. The second, cognitive symptoms, include problems with executive functions, where an individual has difficulty absorbing and interpreting information and making decisions based on that information, an inability to sustain attention, and working memory deficits. Lastly, negative symptoms are deficits or reductions in normal emotion and behavior, including flat or blunted affect (immobile expression, monotonous voice), lack of pleasure in everyday life (anhedonia, like depression) and lack of motivation (avolition), decreased ability to initiate and sustain planned activity, poverty of speech (alogia) and infrequent speech (even when forced to interact). As such, an individual suffering from a psychotic disorder has difficulty recognizing what is real. There is not one specific cause of a psychotic disorder.

A psychotic disorder may be a result of a mental health condition, a physical illness or injury, substance abuse, emotional trauma, genetic makeup, or any combination thereof. Given the complex nature of a psychotic disorder and diversity of causes, it is incredibly difficult to diagnosis the underlying cause of a psychotic disorder in an individual. Psychotic disorders affect at least 1% of the population globally and are lifelong, disabling illnesses. In the United States about 3% of the population will manifest a psychotic disorder at some point in time.

One problem currently faced by the healthcare profession is that the diagnosis of a psychotic disorder due to a mental health condition first requires excluding other potential causes. If causes such as, e.g., a physical illness or injury like a central nervous system disease, a brain tumor, an infection, epilepsy, toxin exposure or sleep deprivation; a substance abuse like alcohol, marijuana, LSD, or amphetamines; an emotional trauma like a death, war or sexual assault; or other health problems as a cause, then a mental health condition might be the reason for the psychotic disorder. If the cause is related to a mental health condition, early diagnosis is critical as early treatment provides the best hope of recovery. Research shows that the earlier an individual experiencing a psychotic disorder receives treatment, the better the individual's long-term quality of life.

Another problem facing the healthcare profession is that the only drugs approved for treating a psychotic disorder are dopaminergic-based anti-psychotic drugs (APDs) like dopamine receptor blockers. However, such APDs merely treat the psychotic symptoms of a psychotic disorder such as delusions and hallucinations. APDs have no effect on negative or cognitive symptoms, which are the most disabling impairments to an individual in leading a normal life, and that most affect their quality of living. Despite considerable recent effort by the pharmaceutical industry, no novel mechanisms have yet been approved for addressing the cognitive and negative symptoms associated with a psychotic disorder and there have been many late-stage failures. As cognitive and negative symptoms are almost universal to all psychotic disorders, the ineffectiveness of APDs is a driving factor for the poor social and functional outcomes that bring high personal and societal costs to an individual suffering from a psychotic disorder.

Sadly, psychotic disorders currently cannot be prevented. This is why the sooner a diagnosis is determined and a proper therapy initiated, the better the outcome for an individual. For example, early treatment may help prevent all symptoms associated with a psychotic disorder and seeking help as soon as possible can help the person's life, family, and relationships. In addition, a more accurate diagnosis of a psychotic disorder can better assist the healthcare provider in prescribing the correct medication. For example, given the great heterogeneity in terms of causes underlying a psychotic disorder, symptoms associated with a psychotic disorder, mechanisms involved in the pathology, and responses to a particular APD, a therapy is many times initiated as a trial and error process until the best medicine is identified. Thus, developing better more accurate methods to diagnosis a psychotic disorder is critical to effectively treating an individual suffering from this condition.

SUMMARY

In one aspect, the present specification discloses a system and method of assigning an individual or patient to a group for a clinical study on a psychotic disorder using a non-invasive computational device-based test. The disclosed group assignment system and method comprises a) having the individual perform the latent inhibition test program running on the computational device; b) measuring a latent inhibition response of the individual to calculate a latent inhibition score to determine whether the individual exhibits an attenuated latent inhibition response, a normal latent inhibition response or an enhanced latent inhibition response; and c) assigning the individual to a group designated by the clinical study. Disclosed latent inhibition test program procedures comprises a pre-exposure phase and a test phase.

In another aspect, the present specification discloses a system and method to determine a psychotic disorder of an individual using a non-invasive computational device-based test. The disclosed psychotic disorder determination system and method comprises a) entering information about the individual into a latent inhibition test program running on a computational device; b) having the individual perform the latent inhibition test program running on the computational device; c) measuring a latent inhibition response of the individual to calculate a latent inhibition score to determine whether the individual exhibited an attenuated latent inhibition response, a normal latent inhibition response or an enhanced latent inhibition response; and d) calculating the psychotic disorder of the individual. The disclosed information includes medical history of the individual including whether this is an initial assessment or a subsequent assessment for a psychotic disorder, whether or not the individual is currently experiencing psychotic symptoms, whether or not the individual has a history of a psychotic disorder, and/or whether or not the individual has a history of resistance to anti-psychotic drug treatment. The disclosed latent inhibition test program includes procedures comprising a pre-exposure phase and a test phase.

In another aspect, the present specification discloses a system and method of recommending a therapy to treat an individual with a psychotic disorder using a non-invasive computational device-based test. The disclosed therapy recommendation system and method comprises a) entering information about the individual into a latent inhibition test program running on a computational device; b) having the individual perform the latent inhibition test program running on the computational device' c) measuring a latent inhibition response of the individual to calculate a latent inhibition score to determine whether the individual exhibited an attenuated latent inhibition response, a normal latent inhibition response or an enhanced latent inhibition response; and d) calculating the recommend therapy to treat an individual. The disclosed information includes medical history of the individual including whether this is an initial assessment or a subsequent assessment for a psychotic disorder, whether or not the individual is currently experiencing psychotic symptoms, whether or not the individual has a history of a psychotic disorder, and/or whether or not the individual has a history of resistance to anti-psychotic drug treatment. The disclosed latent inhibition test program includes procedures comprising a pre-exposure phase and a test phase. The disclosed recommended therapy including, e.g., i) no therapy recommendation; or ii) a therapy recommendation including treating with a pro-cognitive drug, treating with an anti-psychotic drug, treating with clozapine or an alternative drug for treatment-resistant psychotic symptoms, or any combination thereof.

BRIEF DESCRIPTION OF THE DRAWINGS

The accompanying drawings illustrate aspects of the present invention. In such drawings:

FIG. 1 is a schematic representation of an exemplary computer system disclosed herein;

FIG. 2 is a flow chart of the present computer implemented assessment method;

FIG. 3 is a flow chart of the pre-exposure portion of the present computer implemented assessment method of FIG. 2;

FIG. 6 is a matrix of diagnosis and treatment recommendations according to scores based on latent inhibition using the systems and methods disclosed herein;

FIG. 7 is a matrix of diagnosis and treatment recommendations according to scores based on latent inhibition and working memory using the systems and methods disclosed herein; and The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DESCRIPTION

Figure 4:
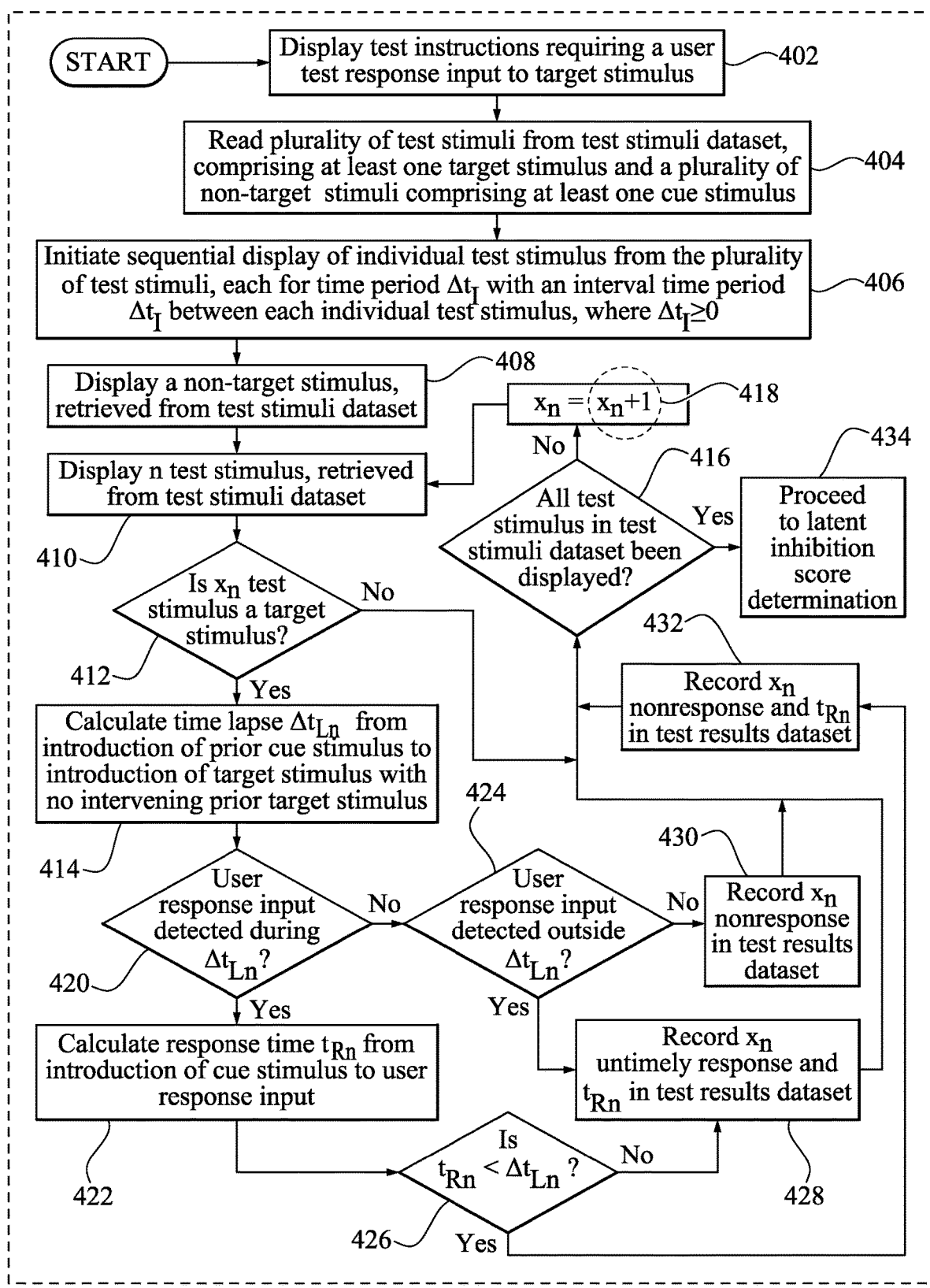
FIG. 4 is a flow chart of the test portion of the present computer implemented assessment method of FIG. 2.

Each of us experience an influx of emotions, sensations, and sounds throughout our daily life. If we had to consciously decide at all times what to ignore and what to pay attention to, we would quickly become overstimulated. However, most of us are able to screen and shut out of our awareness to this constant stream of previously tagged incoming stimuli using a behavioral phenomenon called latent inhibition.

Latent inhibition refers to the reduced ability to learn the relevance of a stimulus if there has already been previous learning about that same stimulus in different or even neutral context. As such, a familiar or irrelevant stimulus takes longer to acquire meaning or salience compared to a new or relevant stimulus. This process enables us to reduce our attention or ignore such benign stimuli (attentional filtering) and selectively attend to the new or relevant stimuli. Thus, latent inhibition can be seen as a measure of the ability to ignore irrelevant stimuli. This tendency to disregard previously irrelevant stimuli is involuntary, meaning the brain automatically carries out the process, and is believed to prevent sensory overload.

Latent inhibition is a normal modulation of associative learning. The basic idea of latent inhibition is that it is often easier to learn something new than to unlearn something familiar. In particular, once you have learned to recognize something or associate it with something else, it is difficult to unlearn it if its meaning changes. It is often easier to make associations to something new than to reassign associations that have already been made to something familiar. The prior learning produces an interference effect.

An individual demonstrating the inability to discriminate between relevant and irrelevant stimuli has latent inhibition dysfunction. There are two poles of latent inhibition dysfunction: 1) attenuated latent inhibition defect which is a failure to ignore irrelevant stimuli; and 2) enhanced latent inhibition defect which is a failure to dis-ignore irrelevant stimuli when they become relevant.

Also known as a disrupted or reduced latent inhibition defect, in an individual manifesting an attenuated latent inhibition defect there is an absence of slower learning to previously irrelevant stimulus (pre-exposed cue) compared to a novel stimulus (non-pre-exposed cue). An individual who shows an inability to ignore previously exposed irrelevant stimuli. An individual who maintains attention to all stimuli, regardless of its relevance because the individual is unable to focus and disregard irrelevant information.

Also known as a potentiated or persistent latent inhibition defect, in an individual manifesting an enhanced latent inhibition defect there is an exaggeration in the reduction in learning to a previously irrelevant stimulus (pre-exposed cue), compared to a novel stimulus (non-pre-exposed cue). An individual fails to stop ignoring the irrelevant stimulus once it becomes relevant. An individual shows behavioral inflexibility or attentional perseveration. Facilitated learning of inattention to the previously irrelevant stimulus.

Latent inhibition assays have been developed in order to determine whether latent inhibition of an individual is functioning within normal ranges. These assays generally fall into one of two study designs, namely between-participant design and within-participant design.

In a between-participant design of a latent inhibition assay, participants are allocated either to a pre-exposed group or a non-pre-exposed group. Both groups participate in the pre-exposure phase in which the pre-exposed stimulus is rendered familiar (often in conjunction with a masking paradigm). In the test phase, participants in the pre-exposed group are assessed on their ability to learn an association between the pre-exposed stimulus and a target outcome (pre-exposure condition), while participants in the non-pre-exposed group are assessed on their ability to learn an association between the pre-exposed stimulus and a novel stimulus with the same target outcome (non-pre-exposure condition). Latent inhibition is demonstrated when participants from the pre-exposed group are slower to learn the cue-target association than the participants from the non-pre-exposed group.

The procedure used in a latent inhibition assay using the between-participant design has several limitations, the most prominent being that both the pre-exposed and non-pre-exposed groups are composed of different participants which makes it difficult to match patients with identical states across groups and as such confounds are introduced when comparing an effect of latent inhibition in patients to the performance level seen in relative control group of participants.

In a within-participant design of a latent inhibition assay, all participants participate in the pre-exposure phase in which the pre-exposed stimulus is rendered familiar/irrelevant (often in conjunction with a masking paradigm). A within-participant design further includes a test phase. In the test phase, participants are measured in their ability to learn an association between the pre-exposed stimulus and a target outcome (pre-exposure condition) and a novel stimulus with the same target outcome (non-pre-exposure condition).

Within-participant designs have advantages over between-participant designs in that they allow for performance and learning about both the pre-exposed and non-pre-exposed stimuli to be compared within the same individual. In between-participant designs, different participants are assigned to either a pre-exposed or non-pre-exposed group and then compared for their performance; as such between-participant designs do not allow for a measure of latent inhibition per individual and make it difficult to match participants and patients with identical symptom states across the two groups.

However, the procedures used in latent inhibition assays relying on current within-participant designs have several limitations, the most prominent being that an expectation of the stimulus-target is established prior to the test phase through instruction which generates a procedure that aligns itself with other learning phenomena other than latent inhibition. For example, by creating an expectation of target appearance during the pre-exposure phase, an effect of conditioned inhibition (instead of latent inhibition) is learned because the target outcome was expected to appear (and did not) at a time when the pre-exposed stimulus was presented. Conditioned inhibition occurs when there is a reduction in learning of the cue-target association during the test stage due to the cue predicting the absence of the target during pre-exposure. This negative prediction error results in the formation of an inhibitory association between the pre-exposed stimulus and the target outcome, slowing later learning for reasons other than latent inhibition.

In addition, exposing the target outcome from the test phase in the pre-exposure phase, unpaired with the cue, establishes an alternative limitation, learned irrelevance. Learned irrelevance occurs when there is a reduction in learning due to the cue being an infrequent predictor of the target outcome during the pre-exposure phase. This negative prediction error results in the formation of a positive association between the pre-exposed stimulus and the absence of the target outcome, slowing later learning for reasons other than latent inhibition.

The present specification discloses systems and methods of measuring latent inhibition that address the problems associated with current within-participant latent inhibition paradigms, including the confounds of conditioned inhibition and learned irrelevance. The disclosed systems and methods ensure this, in part, by setting up no expectation of the target stimulus either through instruction or explicit exposure to the target outcome prior to the pre-exposure phase. This is achieved, in part, by establishing all stimuli as relevant during the pre-exposure phase, and an expectation of the target stimulus is only introduced prior to the test stage. This removes the influence/observation of other learning effects, including the cognitive-behavioral effects of conditioned inhibition and learned irrelevance. By overcoming the design and interpretational problems of current latent inhibition testing, the disclosed systems and methods enhance the development of cognitive explanations about schizophrenia and the utility of latent inhibition assessment as a diagnostic and screening tool.

Computer networks in general are well known in the art, often having one or more client computers and one or more servers, on which any of the methods and systems of various disclosed embodiments may be implemented. In particular the computer system, or server in this example, may represent any of the computer systems and physical components necessary to perform the computerized methods discussed in connection with the present figures and, in particular, may represent a server (cloud, array, etc.), client, or other computer system upon which e-commerce servers, websites, databases, web browsers and/or web analytic applications may be instantiated.

As shown in FIG. 1, the present computer system 20 includes in at least one example embodiment, an optional illustrated exemplary server 22 with associated database 24 and client computing device 26 (which may also be referred to as a patient computer or patient computing device), and a patient response device 28 (which may be separate or integral with the patient computing device 26). Although the system 20 is described as separate components, the present system may be integrated into a single device, where the patient computer 26 could be a laptop, tablet computer, smartphone, or a dedicated device, with the database 24 being stored in locally within the patient computer 26 and/or being communicated to one or more other devices, such as a service provider's device (physician, clinician, etc.). Each computing device within the present system 20 is generally known to a person of ordinary skill in the art, and each may include a processor, a bus for communicating information, a main memory coupled to the bus for storing information and instructions to be executed by the processor and for storing temporary variables or other intermediate information during the execution of instructions by processor, a static storage device or other non-transitory computer readable medium for storing static information and instructions for the processor, and a storage device, such as a hard disk, may also be provided and coupled to the bus for storing information and instructions. The server 22 and client computer 26 may optionally be coupled to a display for displaying information. However, in the case of server 22, such a display may not be present and all administration of the server may be via remote clients. Further, the server 22 and client computer 26 may optionally include connection to an input device for communicating information and command selections to the processor, such as a keyboard, mouse, touchpad, microphone, and the like. Moreover, the client computer 26 may optionally include connection to an output device for communicating information and command selections to the patient P or the therapist such as a speaker, etc.

At the outset, it should be noted that communication between each of the server 22 and client computer 26 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the terms "patient device" (and equivalent names for computing devices that describe the user) are intended to include any type of computing or electronic device now known or later developed, such as desktop computers, mobile phones, smartphones, laptop computers, tablet computers, virtual reality systems, personal data assistants, gaming devices, unattended terminals, access control devices, point of interaction ("POI") systems, etc.

The server 22 and client computer 26 may also include a communication interface coupled to the bus, for providing two-way, wired and/or wireless data communication to and from the server and/or client computers. For example, the communications interface may send and receive signals via a local area network, public network, intranet, private network (e.g., a VPN), or other network, including the Internet.

In the present illustrated example, the hard drive of the server 22 (including an optional third-party server and/or mobile app backend service, and the like) and/or one or all of the client computer 26 is encoded with executable instructions, that when executed by a processor cause the processor to perform acts as described in the methods of FIGS. 2-5. The server 22 communicates through the Internet, intranet, or other network with the client computer 26 to cause information and/or graphics to be displayed on the screen, such as HTML code, text, images, and the like, sound to be emitted from the speakers, etc. The server 22 may host a URL site with information, which may be accessed by the client computer 26. Information transmitted to the client computer 26 may be stored and manipulated according to the methods described below, using the software encoded on the client device 26. Although the computing devices are illustrated schematically as laptops, the computing devices may include desktops, tablets, cellular devices (e.g., smart phones, such as iOS devices, ANDROID devices, WINDOWS devices, and the like), or any other computing device now known or later developed. Further, although the patient response device 28 is illustrated as a hand-held response device, the patient P can enter a response into the system 20 in a number of ways, including interacting with a touchscreen (e.g., touching a user interface element, such as a button, etc.), a verbal input (e.g., speaking into the microphone, with the response analyzed by known speech recognition systems, etc.), a keyboard input (such as, typing a response word or series of characters, or contacting a particular key to register a response, etc.), or other input means now known or later developed.

Still looking at FIG. 1, the computing devices may be one of many available computing devices capable of running executable programs and/or a browser instance. For example, they may be a mobile device, such as a tablet computer or a mobile phone device with computer capabilities, a laptop, a desktop, or other computing device. Executable instructions for the present method may be installed on the server 22 that hosts a web or other application caused to display a user interface on the client device 26. Alternatively, executable instructions for all or at least part of the present method may be installed locally on the client device 26, with the various datasets generated being stored locally. In an example embodiment, the client device 26 access and interact with the graphical user interface through a web browser instance, such as FIREFOX, CHROME, SAFARI, INTERNET EXPLORER, and the like, or through a desktop application. The web application is hosted on an application server with application hosting capabilities. In another example embodiment, the client device 26 can access and interact with the graphical user interface through either a web application running on a mobile web browser or a mobile application (commonly called an "app").

Alternatively, executable instructions for carrying out all or at least part of the present method may be installed locally on the client device 26. For example, the client device 26 may be required to locally install an application on a smartphone device for carrying out all or part of the present method. In an example embodiment, an executable application file is installed on the client device 26 so that messages can be sent to and received from the server 22 (or between the devices, if any addition devices are connected to the system 20), with the server sending, receiving, and/or relaying the messages to the client device 26. The messages may be comprised of various forms of data, such as alphanumeric text, pictures, animations, links, and so on. In yet another example embodiment, one party may have an application installed on the computing device, while the other party sends and receives messages through a browser instance.

The present specification discloses three systems and computer implemented assessment methods: 1) a system and method of assigning an individual to a group participating in a clinical study regarding a psychotic disorder; 2) a system and method of determine whether and what type of psychotic disorder an individual may be suffering from; and 3) a system and method of recommending a therapy to treat an individual with a psychotic disorder. All three disclosed systems and computer implemented assessment methods use a non-invasive computational device-based test. In addition, as discussed in detail below, while some aspects of the non-invasive computational device-based test are common to all three disclosed systems and methods, other aspects are present in only two of the three while some aspects are present in one of the disclosed systems and methods.

FIG. 2 illustrates an example embodiment of the present computer implemented assessment method 200, broadly showing the optional steps in carrying out the method 200. The present method 200 may be carried out utilizing discrete modules or separate applications or launching a single application capable of performing all steps of the present method 200. Broadly described, the present latent inhibition test method 200 includes the step of initializing a pre-exposure portion of the application 300, initializing the test portion of the application 400, initializing the latent inhibition scoring portion of the application 500. Once a latent inhibition score and/or outcome assessment has been calculated, one or more of the methods of determining a clinical study group assignment 208, determining a patient psychotic disorder 210, and determining an appropriate patient therapy 212 can be implemented selectively or automatically.

A psychotic disorder determination method and a therapy recommendation method disclosed herein comprise a step of entering information about an individual into a latent inhibition test program running on a computational device. A group assignment method disclosed herein may optionally comprise a step of entering information about an individual into a latent inhibition test program running on a computational device. Typically this information includes an individual's medical history and current condition. Information disclosed herein includes, without limitation, whether this is an initial assessment or a subsequent assessment of an individual, whether or not the individual is currently experiencing psychotic symptoms, whether or not the individual has a history of a psychotic disorder, and whether or not the individual has a history of resistance to anti-psychotic drug treatment.

A group assignment method, a psychotic disorder determination method, and a therapy recommendation method disclosed herein comprises, in part, a step of having an individual perform a latent inhibition test program running on a computational device. In one embodiment, a latent inhibition test program includes procedures comprising a pre-exposure phase and a test phase.

Turning to the flow chart of FIG. 3, an example embodiment of the pre-exposure phase or portion of the application 300 is illustrated in greater detail. After initializing the application, the pre-exposure (P.E.) instructions are displayed 302 on the patient computing device 26, for example, by displaying the instructions to the patient P on a monitor or screen of the patient computing device 26. Any data received/transmitted by the patient computing device 26 in the present computer method can be communicated from/to a local database (e.g., stored on the patient computing device 26 hard drive) or communicated from/to a remote server on a local intranet or through the Internet, or other known transmission means. The P.E. instructions establish a set of rules which should be followed by the patient P during the pre-exposure portion of the present method 200 for the successful completion of the pre-exposure phase 300. In one or more embodiments, certain parameters of the P.E. instructions can be set by the professional administering the assessment, such as the time period that a stimulus is displayed, the time interval between the display stimulus, the particular pre-exposure dataset being used (if multiple datasets are available, etc.). Although the present method 200 describes "displaying" instructions, stimuli, or other data to the patient P through the patient computing device 26 as a form of communication, the form of communication can vary, including an audio communication (e.g., through a speaker on a computer, etc.); and thus, is not limited to displaying on the computer screen or other display means. For example, a pre-exposure phase disclosed herein includes presenting an individual with a first set of directions for how to respond to each stimulus of a first group of stimuli that will be presented to the individual while performing a latent inhibition test program disclosed herein. In an aspect of this embodiment, a first set of directions disclosed herein includes pre-exposure phase instructions which inform the individual on how to respond to each stimulus of the first group of stimuli that will be presented to the individual during a pre-exposure phase disclosed herein.

The pre-exposure dataset is retrieved from the database by the application. The application determines in step 304 the type of responses required as an input from the patient computing device 26. In one embodiment, pre-exposure phase instructions include n-back instructions. When a n-back response is required 308, then the application requires an input from the patient computing device 26 for a P.E. stimulus displayed that matches a prior P.E. stimulus (a prior matching P.E. stimulus) displayed n-positions prior (where "n" can be any predetermined number, depending on the dataset and the design of the assessment, such as 0, 1, 2, 3, 4, . . . ). The application requires an input from the patient computing device 26 within a predetermined time interval after the start of display of each stimulus in the P.E. stimuli dataset retrieved from the database 306. The "n" value is generally related to the particular P.E. dataset utilized, but may be set by the profession in one or more example embodiments.

In an aspect of this embodiment, pre-exposure phase instructions require the individual to respond to a stimulus of a first group of stimuli as it appears on the screen (0-back). In another aspect of this embodiment, pre-exposure phase instructions require the individual to respond to a current stimulus of the first group of stimuli only if the current stimulus is the same as a stimulus shown one position back in a sequence of the first group of stimuli (1-back). In yet another aspect of this embodiment, pre-exposure phase instructions require the individual to respond to a current stimulus of the first group of stimuli only if the current stimulus is the same as a stimulus shown two positions back in a sequence of the first group of stimuli (2-back). In another aspect of this embodiment, an individual is asked to respond to each stimulus in a specific manner, including, without limitation, verbally acknowledge the that a stimulus was presented or by physically inputting the response into a computational device, such as by pressing a button on a keypad or clicking a control device like a mouse.

A pre-exposure phase disclosed herein includes presenting an individual with a first group of stimuli. The application causes each of the P.E. stimuli in the P.E. stimulus dataset to be displayed sequentially in a predetermined order (or, optionally, a random order in one or more example embodiments) 310. The $x_n$ stimulus is displayed for a time period $\Delta t_{PEn}$ with an interval time period of $\Delta t_{In}$ where $\Delta t_{In}$ can be greater than or equal to 0 seconds. Although, $\Delta t_{PEn}$ and $\Delta t_{In}$ are generally constant throughout the P.E. phase, the times can be varied in one or more example embodiments. The P.E. stimulus dataset comprises one or more pre-exposed stimulus, one or more neutral stimuli, and optionally, other stimuli. If a patient response input is detected 312, it is determined if the response is detected during the time period permitted for response, which can be $\Delta t_{PEn}$, $\Delta t_{PEn}$+ $\Delta t_{In}$, or other predetermined time period for which a patient response input in appropriate. In the illustrated example embodiment method, for each time period, the application determines whether a patient ("user") response input is detected (e.g., from a response clicker, a keyboard input, a voice response input, etc.). If no patient response input is detected, the application compares the nonresponse to the dataset of correct responses for that particular iteration "n" to determine if the nonresponse is correct, step 314, thereafter, recording the nonresponse as correct or incorrect in the P.E. results dataset, in step 316. Likewise, if a patient response input is detected, the application compares the response to the dataset of correct responses for that particular iteration "n" to determine if the response is correct 318 (e.g., the response was received during a time period associated with a prior matching P.E. stimulus displayed n stimuli prior), thereafter, recording the response as correct or incorrect in the P.E. results dataset, in step 320. Of course, this comparison need not be immediately be made; the application can collect a dataset of responses and time for each response for comparison at any point in time, including a later analysis conducted at a time in the future. The application will continue to display P.E. stimuli in iterations 322 until all P.E. stimuli in the P.E. stimuli dataset have been displayed, step 324. Alternately, the number of P.E. stimuli in the P.E. stimuli dataset can be accessed by the application (e.g., the known number can be entered, or associated with the dataset, etc.), where the application displays successive P.E. stimuli up to that number known number. After all the P.E. stimuli have been displayed and the time period for any patient response has ended, using one or more of the disclosed algorithms on the P.E. results dataset, the application calculates a P.E. result, step 326. As the P.E. result can be used in conjunction with test phase and/or to determine whether to proceed with the test stage, it is determined if the P.E. results calculated are within parameters that are predetermined, 328, or set by the professional administering or analyzing the present assessment. The application can proceed automatically to the test phase of the assessment 332, or the application can terminate the assessment at the end of the P.E. phase 330 or at any time, or the application can stop and await manual instruction input from the administrator/professional.

In an aspect of this embodiment, stimuli belonging to a first group of stimuli disclosed herein are presented to an individual in a random order. In this step, an individual, without his knowledge, is familiarize to a preexposure stimulus without any association to a target stimulus because the first group of stimuli does not contain a target stimulus. If a 1-back or a 2-back design, but not a 0-back design, is employed, a pre-exposure phase procedure is also used to assess working memory. The purpose of presenting this first group of stimuli is to mitigate the effects of conditional learning and learned irrelevance. Conditional learning is mitigated because a target stimulus is not presented in the preexposure phase. This avoids the expectation of a target stimulus being presented during the preexposure phase when in fact it will not be, thereby mitigating conditional learning. Learned irrelevance is also mitigated because a target stimulus is not presented during the preexposure phase. This avoids any association of the target stimulus with the pre-exposure stimulus.

Each stimulus from the first group of stimuli being presented to the individual is done so for a defined period of time. Generally, a defined period of time for presenting a stimulus from the first group of stimuli to an individual needs to be of a long enough duration that the individual can perceive that the stimulus is being presented to the individual. In an aspect of this embodiment, a defined period of time for presenting a stimulus from the first group of stimuli can be between, e.g., about 10 msec to about 10,000 msec, about 100 msec to about 5,000 msec, about 250 msec to about 2,500 msec, about 500 msec to about 1,500 msec, about 750 msec to about 1,250 msec, or about 1,000 msec In other aspects of this embodiment, a defined period of time for presenting a stimulus from the first group of stimuli can be, e.g., about 10 msec, about 50 msec, about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1,000 msec, about 1,100 msec, about 1,200 msec, about 1,300 msec, about 1,400 msec, about 1,500 msec, about 1,600 msec, about 1,700 msec, about 1,800 msec, about 1,900 msec, about 2,000 msec, about 2,500 msec, or about 3,000 msec. In yet other aspects of this embodiment, a defined period of time for presenting a stimulus from the first group of stimuli can be, e.g., at least 10 msec, at least 50 msec, at least 100 msec, at least 150 msec, at least 200 msec, at least 250 msec, at least 300 msec, at least 350 msec, at least 400 msec, at least 450 msec, at least 500 msec, at least 550 msec, at least 600 msec, at least 650 msec, at least 700 msec, at least 750 msec, at least 800 msec, at least 850 msec, at least 900 msec, at least 950 msec, at least 1,000 msec, at least 1,100 msec, at least 1,200 msec, at least 1,300 msec, at least 1,400 msec, at least 1,500 msec, at least 1,600 msec, at least 1,700 msec, at least 1,800 msec, at least 1,900 msec, at least 2,000 msec, at least 2,500 msec, or at least 3,000 msec. In still other aspects of this embodiment, a defined period of time for presenting a stimulus from the first group of stimuli can be, e.g., at most 10 msec, at most 50 msec, at most 100 msec, at most 150 msec, at most 200 msec, at most 250 msec, at most 300 msec, at most 350 msec, at most 400 msec, at most 450 msec, at most 500 msec, at most 550 msec, at most 600 msec, at most 650 msec, at most 700 msec, at most 750 msec, at most 800 msec, at most 850 msec, at most 900 msec, at most 950 msec, at most 1,000 msec, at most 1,100 msec, at most 1,200 msec, at most 1,300 msec, at most 1,400 msec, at most 1,500 msec, at most 1,600 msec, at most 1,700 msec, at most 1,800 msec, at most 1,900 msec, at most 2,000 msec, at most 2,500 msec, or at most 3,000 msec.

In further other aspects of this embodiment, a defined period of time for presenting a stimulus from the first group of stimuli can be from, e.g., about 10 msec to about 100 msec, about 10 msec to about 200 msec, about 10 msec to about 300 msec, about 10 msec to about 400 msec, about 10 msec to about 500 msec, about 10 msec to about 600 msec, about 10 msec to about 700 msec, about 10 msec to about 800 msec, about 10 msec to about 900 msec, about 10 msec to about 1,000 msec, about 10 msec to about 1,100 msec, about 10 msec to about 1,200 msec, about 10 msec to about 1,300 msec, about 10 msec to about 1,400 msec, about 10 msec to about 1,500 msec, about 10 msec to about 1,600 msec, about 10 msec to about 1,700 msec, about 10 msec to about 1,800 msec, about 10 msec to about 1,900 msec, about 10 msec to about 2,000 msec, about 10 msec to about 3,000 msec, about 100 msec to about 200 msec, about 100 msec to about 300 msec, about 100 msec to about 400 msec, about 100 msec to about 500 msec, about 100 msec to about 600 msec, about 100 msec to about 700 msec, about 100 msec to about 800 msec, about 100 msec to about 900 msec, about 100 msec to about 1,000 msec, about 100 msec to about 1,100 msec, about 100 msec to about 1,200 msec, about 100 msec to about 1,300 msec, about 100 msec to about 1,400 msec, about 100 msec to about 1,500 msec, about 100 msec to about 1,600 msec, about 100 msec to about 1,700 msec, about 100 msec to about 1,800 msec, about 100 msec to about 1,900 msec, about 100 msec to about 2,000 msec, about 100 msec to about 3,000 msec, about 250 msec to about 300 msec, about 250 msec to about 400 msec, about 250 msec to about 500 msec, about 250 msec to about 600 msec, about 250 msec to about 700 msec, about 250 msec to about 800 msec, about 250 msec to about 900 msec, about 250 msec to about 1,000 msec, about 250 msec to about 1,100 msec, about 250 msec to about 1,200 msec, about 250 msec to about 1,300 msec, about 250 msec to about 1,400 msec, about 250 msec to about 1,500 msec, about 250 msec to about 1,600 msec, about 250 msec to about 1,700 msec, about 250 msec to about 1,800 msec, about 250 msec to about 1,900 msec, about 250 msec to about 2,000 msec, about 250 msec to about 3,000 msec, about 500 msec to about 600 msec, about 500 msec to about 700 msec, about 500 msec to about 800 msec, about 500 msec to about 900 msec, about 500 msec to about 1,000 msec, about 500 msec to about 1,100 msec, about 500 msec to about 1,200 msec, about 500 msec to about 1,300 msec, about 500 msec to about 1,400 msec, about 500 msec to about 1,500 msec, about 500 msec to about 1,600 msec, about 500 msec to about 1,700 msec, about 500 msec to about 1,800 msec, about 500 msec to about 1,900 msec, about 500 msec to about 2,000 msec, about 500 msec to about 3,000 msec, about 750 msec to about 800 msec, about 750 msec to about 900 msec, about 750 msec to about 1,000 msec, about 750 msec to about 1,100 msec, about 750 msec to about 1,200 msec, about 750 msec to about 1,300 msec, about 750 msec to about 1,400 msec, about 750 msec to about 1,500 msec, about 750 msec to about 1,600 msec, about 750 msec to about 1,700 msec, about 750 msec to about 1,800 msec, about 750 msec to about 1,900 msec, about 750 msec to about 2,000 msec, about 750 msec to about 3,000 msec, about 1,000 msec to about 1,100 msec, about 1,000 msec to about 1,200 msec, about 1,000 msec to about 1,300 msec, about 1,000 msec to about 1,400 msec, about 1,000 msec to about 1,500 msec, about 1,000 msec to about 1,600 msec, about 1,000 msec to about 1,700 msec, about 1,000 msec to about 1,800 msec, about 1,000 msec to about 1,900 msec, about 1,000 msec to about 2,000 msec, about 1,000 msec to about 3,000 msec, about 1,250 msec to about 1,300 msec, about 1,250 msec to about 1,400 msec, about 1,250 msec to about 1,500 msec, about 1,250 msec to about 1,600 msec, about 1,250 msec to about 1,700 msec, about 1,250 msec to about 1,800 msec, about 1,250 msec to about 1,900 msec, about 1,250 msec to about 2,000 msec, about 1,250 msec to about 3,000 msec, about 1,500 msec to about 1,600 msec, about 1,500 msec to about 1,700 msec, about 1,500 msec to about 1,800 msec, about 1,500 msec to about 1,900 msec, about 1,500 msec to about 2,000 msec, about 1,500 msec to about 3,000 msec, about 2,000 msec to about 3,000 msec, or about 2,500 msec to about 3,000 msec.

Presentation of a stimulus from the first group of stimuli may optionally include an interval of time where no stimulus is presented to an individual performing the pre-exposure phase. These intervals are simply gaps between the presentation of each stimulus. An interval of time between the presentation of each stimulus from the first group of stimuli is done for a defined period of time. In one embodiment, presentation of each stimuli from the first group of stimuli does not include an interval period of time. In another embodiment, an interval period of time is present between the presentation of each stimulus. In an aspect of this embodiment, an interval period of time between the presentation of a stimulus from the first group of stimuli can be between, e.g., about 1 msec to about 10,000 msec, about 5 msec to about 1,000 msec, about 10 msec to about 500 msec, about 15 msec to about 250 msec, about 20 msec to about 100 msec, about 25 msec to about 75 msec, or about 50 msec.

In other aspects of this embodiment, an interval period of time between the presentation of a stimulus from the first group of stimuli can be, e.g., about 10 msec, about 50 msec, about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1,000 msec, about 1,100 msec, about 1,200 msec, about 1,300 msec, about 1,400 msec, about 1,500 msec, about 1,600 msec, about 1,700 msec, about 1,800 msec, about 1,900 msec, about 2,000 msec, about 2,500 msec, or about 3,000 msec. In yet other aspects of this embodiment, an interval period of time between the presentation of a stimulus from the first group of stimuli can be, e.g., at least 10 msec, at least 50 msec, at least 100 msec, at least 150 msec, at least 200 msec, at least 250 msec, at least 300 msec, at least 350 msec, at least 400 msec, at least 450 msec, at least 500 msec, at least 550 msec, at least 600 msec, at least 650 msec, at least 700 msec, at least 750 msec, at least 800 msec, at least 850 msec, at least 900 msec, at least 950 msec, at least 1,000 msec, at least 1,100 msec, at least 1,200 msec, at least 1,300 msec, at least 1,400 msec, at least 1,500 msec, at least 1,600 msec, at least 1,700 msec, at least 1,800 msec, at least 1,900 msec, at least 2,000 msec, at least 2,500 msec, or at least 3,000 msec. In still other aspects of this embodiment, an interval period of time between the presentation of a stimulus from the first group of stimuli can be, e.g., at most 10 msec, at most 50 msec, at most 100 msec, at most 150 msec, at most 200 msec, at most 250 msec, at most 300 msec, at most 350 msec, at most 400 msec, at most 450 msec, at most 500 msec, at most 550 msec, at most 600 msec, at most 650 msec, at most 700 msec, at most 750 msec, at most 800 msec, at most 850 msec, at most 900 msec, at most 950 msec, at most 1,000 msec, at most 1,100 msec, at most 1,200 msec, at most 1,300 msec, at most 1,400 msec, at most 1,500 msec, at most 1,600 msec, at most 1,700 msec, at most 1,800 msec, at most 1,900 msec, at most 2,000 msec, at most 2,500 msec, or at most 3,000 msec.

In further other aspects of this embodiment, an interval period of time between the presentation of a stimulus from the first group of stimuli can be, e.g., about 10 msec to about 100 msec, about 10 msec to about 200 msec, about 10 msec to about 300 msec, about 10 msec to about 400 msec, about 10 msec to about 500 msec, about 10 msec to about 600 msec, about 10 msec to about 700 msec, about 10 msec to about 800 msec, about 10 msec to about 900 msec, about 10 msec to about 1,000 msec, about 10 msec to about 1,100 msec, about 10 msec to about 1,200 msec, about 10 msec to about 1,300 msec, about 10 msec to about 1,400 msec, about 10 msec to about 1,500 msec, about 10 msec to about 1,600 msec, about 10 msec to about 1,700 msec, about 10 msec to about 1,800 msec, about 10 msec to about 1,900 msec, about 10 msec to about 2,000 msec, about 10 msec to about 3,000 msec, about 100 msec to about 200 msec, about 100 msec to about 300 msec, about 100 msec to about 400 msec, about 100 msec to about 500 msec, about 100 msec to about 600 msec, about 100 msec to about 700 msec, about 100 msec to about 800 msec, about 100 msec to about 900 msec, about 100 msec to about 1,000 msec, about 100 msec to about 1,100 msec, about 100 msec to about 1,200 msec, about 100 msec to about 1,300 msec, about 100 msec to about 1,400 msec, about 100 msec to about 1,500 msec, about 100 msec to about 1,600 msec, about 100 msec to about 1,700 msec, about 100 msec to about 1,800 msec, about 100 msec to about 1,900 msec, about 100 msec to about 2,000 msec, about 100 msec to about 3,000 msec, about 250 msec to about 300 msec, about 250 msec to about 400 msec, about 250 msec to about 500 msec, about 250 msec to about 600 msec, about 250 msec to about 700 msec, about 250 msec to about 800 msec, about 250 msec to about 900 msec, about 250 msec to about 1,000 msec, about 250 msec to about 1,100 msec, about 250 msec to about 1,200 msec, about 250 msec to about 1,300 msec, about 250 msec to about 1,400 msec, about 250 msec to about 1,500 msec, about 250 msec to about 1,600 msec, about 250 msec to about 1,700 msec, about 250 msec to about 1,800 msec, about 250 msec to about 1,900 msec, about 250 msec to about 2,000 msec, about 250 msec to about 3,000 msec, about 500 msec to about 600 msec, about 500 msec to about 700 msec, about 500 msec to about 800 msec, about 500 msec to about 900 msec, about 500 msec to about 1,000 msec, about 500 msec to about 1,100 msec, about 500 msec to about 1,200 msec, about 500 msec to about 1,300 msec, about 500 msec to about 1,400 msec, about 500 msec to about 1,500 msec, about 500 msec to about 1,600 msec, about 500 msec to about 1,700 msec, about 500 msec to about 1,800 msec, about 500 msec to about 1,900 msec, about 500 msec to about 2,000 msec, about 500 msec to about 3,000 msec, about 750 msec to about 800 msec, about 750 msec to about 900 msec, about 750 msec to about 1,000 msec, about 750 msec to about 1,100 msec, about 750 msec to about 1,200 msec, about 750 msec to about 1,300 msec, about 750 msec to about 1,400 msec, about 750 msec to about 1,500 msec, about 750 msec to about 1,600 msec, about 750 msec to about 1,700 msec, about 750 msec to about 1,800 msec, about 750 msec to about 1,900 msec, about 750 msec to about 2,000 msec, about 750 msec to about 3,000 msec, about 1,000 msec to about 1,100 msec, about 1,000 msec to about 1,200 msec, about 1,000 msec to about 1,300 msec, about 1,000 msec to about 1,400 msec, about 1,000 msec to about 1,500 msec, about 1,000 msec to about 1,600 msec, about 1,000 msec to about 1,700 msec, about 1,000 msec to about 1,800 msec, about 1,000 msec to about 1,900 msec, about 1,000 msec to about 2,000 msec, about 1,000 msec to about 3,000 msec, about 1,250 msec to about 1,300 msec, about 1,250 msec to about 1,400 msec, about 1,250 msec to about 1,500 msec, about 1,250 msec to about 1,600 msec, about 1,250 msec to about 1,700 msec, about 1,250 msec to about 1,800 msec, about 1,250 msec to about 1,900 msec, about 1,250 msec to about 2,000 msec, about 1,250 msec to about 3,000 msec, about 1,500 msec to about 1,600 msec, about 1,500 msec to about 1,700 msec, about 1,500 msec to about 1,800 msec, about 1,500 msec to about 1,900 msec, about 1,500 msec to about 2,000 msec, about 1,500 msec to about 3,000 msec, about 2,000 msec to about 3,000 msec, or about 2,500 msec to about 3,000 msec.

A first group of stimuli comprises a plurality of stimuli. In an aspect of this embodiment, a first group of stimuli disclosed herein comprises at least one preexposed stimulus, one or more neutral stimuli, or both at least one preexposed stimulus and one or more neutral stimuli. A preexposed stimulus is a stimulus presented during the pre-exposure phase and is intended to represent a familiar stimulus during the test phase. It is predictive of the occurrence of the target stimulus during the test phase. A neutral stimulus is a non-cued stimulus having infrequent association with a preexposed, a non-preexposed, or a target stimulus and as such cannot be accurately used by an individual to anticipate which stimulus will occur next.

A preexposure phase disclosed herein can optionally include measuring a response of an individual to each stimulus from the first group of stimuli. Measurement of these responses is an assessment of compliance with the first set of directions and helps assess the quality of an individual's participation. In an aspect of this embodiment, an individual is allowed to proceed to the test phase of a latent inhibition test program disclosed herein if the individual responses to, e.g., at least 50%, at least 55%, at least 60%, at least 65%, at least 70%, at least 75%, at least 80%, at least 85%, at least 90%, or at least 95% of a first group of stimuli according to the first set of directions.

Turning to the flow chart of FIG. 4, an example embodiment of the test phase or portion of the application 400 is illustrated in greater detail. The test instructions are displayed 402 on the patient computing device 26, step 402, which requires the patient P to enter a response input in relation to a target stimulus. The test dataset is retrieved from the database by the application, where the test dataset includes at least one target stimulus, a plurality of non-target stimuli comprising at least one cue stimuli, where non-target stimuli can further comprise at least one at least one pre-exposed stimuli, a non-pre-exposed stimulus, and one or more neutral stimuli.

A test phase disclosed herein includes presenting an individual with a second set of directions for how to respond to each stimulus of a second group of stimuli that will be presented to the individual while performing a latent inhibition test program disclosed herein. In an aspect of this embodiment, a second set of directions disclosed herein includes test phase instructions which inform the individual on how to respond to each stimulus of the second group of stimuli that will be presented to the individual during a test phase disclosed herein. In an aspect of this embodiment, a second set of directions include test phase instructions that inform the individual to anticipate the occurrence of a target stimulus disclosed herein and to respond accordingly in some manner. For example, an individual how anticipates that a target stimulus will be presented next can indicate so by verbally stating that the target stimulus will occur next, or by physically responding by inputting such anticipation into a computational device, such as by pressing a button on a keypad or clicking a control device like a mouse.

A test phase disclosed herein includes presenting the individual with a second group of stimuli. The purpose of presenting this second group of stimuli is to measure latent inhibition of an individual by measuring the learning rate of the association of the target stimulus to the preexposure and non-preexposure stimuli. In an aspect of this embodiment, stimuli belonging to a second group of stimuli disclosed herein are presented to an individual in a pseudo-random order. In another aspect of this embodiment, stimuli belonging to a second group of stimuli disclosed herein are presented to an individual in a predetermined order. In an aspect of this embodiment, a predetermined order of presenting stimuli belonging to a second group of stimuli disclosed herein to an individual involves presenting an equal number of presentations for a target stimulus occurring immediately after presentation of the preexposed stimulus and immediately after presentation of the non-preexposed stimulus. In other aspects of this embodiment, the presentation of a preexposed stimulus/target stimulus combination and a non-preexposed stimulus/target stimulus combination occurs two times more often, three times more often, four times more often, five times more often, six times more often, seven times more often or eight times more often relative to the presentation of the target stimulus occurring immediately after presentation of a particular neutral stimulus.

The application causes each of the test stimuli in the test stimulus dataset to be displayed sequentially in a predetermined order 406. Each $x_n$ test stimuli is displayed for a time period $\Delta t_{Tn}$ with an interval time period of $\Delta t_{In}$ where $\Delta t_{In}$ can be greater than or equal to 0 seconds. Although, $\Delta t_{Tn}$ and $\Delta t_{In}$ are generally constant throughout the test phase, the times can be varied in one or more example embodiments. In the present example embodiment, initially, a non-target test stimulus is caused to display on the patient computer 26, step 408. However, the test phase maybe varied in one or more example embodiments to display a target stimulus initially, although this is not generally preferred, as the test phase is designed to determine the patient's ability to predict the display of the target stimulus. In step 410, the application causes the "$x_n$" test stimulus (e.g., the next test stimulus in the sequence within the test stimulus dataset) to display on the patient computer 26. If the $x_n$ stimulus is a target stimulus, then, in step 414, the application calculates the time lapse $\Delta t_{Ln}$ from the introduction of the prior cue stimulus up to the introduction of the target stimulus, with no intervening prior target stimuli. Basically, once the cue stimulus is displayed, the time to timely respond ends as soon as the next target stimulus appears. In order for a patient P to have predicted the appearance of the target stimulus, a user response input must be detected during the time lapse $\Delta t_{Ln}$, step 420. If a patient response input is detected during the time lapse $\Delta t_{Ln}$, step 426, then the response time $\Delta t_{R_n}$ is calculated from the introduction of the cue stimulus to when the patient response input is detected. In step 424, if no patient response input is detected during the time lapse $\Delta t_{L_n}$, and is not detected until the target stimulus is displayed or is not detected even after the target stimulus display has ended, then an untimely response (step 428) or a nonresponse (step 430). Whether the response is determined to be timely, untimely, or a nonresponse, the user response input (or lack thereof) is recorded in the test results dataset, steps 428, 430, 432. If the $x_n$ stimulus is not a target stimulus, step 412, then it is determined by the application whether all test stimuli within the test stimulus dataset have been displayed in the sequence, step 416, much like the iterations of the P.E. phase above. If not all test stimuli within the test stimulus dataset have been displayed, the next test stimulus in the sequence called up, 418, for display in step 410, starting the next iteration. If all test stimuli within the test stimulus dataset have been displayed, then the application can proceed automatically to the determination of the latent inhibition score phase of the application, step 434.

In aspects of this embodiment, a test phase comprises 20 occurrences of a preexposed stimulus/target stimulus combination are presented, 20 occurrences of a non-preexposed stimulus/target stimulus combination are presented, and five occurrences of a particular neutral stimulus/target stimulus combination are presented, where four different neutral stimuli are presented for a total number of 20. In other aspects of this embodiment, a test phase comprises 30 occurrences of a preexposed stimulus/target stimulus combination are presented, 30 occurrences of a non-preexposed stimulus/target stimulus combination are presented, and 10 occurrences of a particular neutral stimulus/target stimulus combination are presented, where three different neutral stimuli are presented for a total number of 30. In other aspects of this embodiment, a test phase comprises 30 occurrences of a preexposed stimulus/target stimulus combination are presented, 30 occurrences of a non-preexposed stimulus/target stimulus combination are presented, seven or eight occurrences of a particular neutral stimulus/target stimulus combination are presented, where four different neutral stimuli are presented for a total number of 30 (i.e., two different neutral stimuli are presented seven times while the other two neutral stimuli are presented eight times immediately before the target stimulus. In still other aspects of this embodiment, a test phase comprises 40 occurrences of a preexposed stimulus/target stimulus combination are presented, 40 occurrences of a non-preexposed stimulus/target stimulus combination are presented, and 19 occurrences of a particular neutral stimulus/target stimulus combination are presented, where four different neutral stimuli are presented for a total number of 40.

Each stimulus from the first group of stimuli being presented to the individual is done so for a defined period of time. Generally, a defined period of time for presenting a stimulus from the first group of stimuli to an individual need to be of a long enough duration that the individual can perceive that the stimulus is being presented to the individual. In an aspect of this embodiment, a defined period of time for presenting a stimulus from the second group of stimuli can be between, e.g., about 10 msec to about 10,000 msec, about 100 msec to about 5,000 msec, about 250 msec to about 2,500 msec, about 500 msec to about 1,500 msec, about 750 msec to about 1,250 msec, or about 1,000 msec.

In other aspects of this embodiment, a defined period of time for presenting a stimulus from the second group of stimuli can be, e.g., about 10 msec, about 50 msec, about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1,000 msec, about 1,100 msec, about 1,200 msec, about 1,300 msec, about 1,400 msec, about 1,500 msec, about 1,600 msec, about 1,700 msec, about 1,800 msec, about 1,900 msec, about 2,000 msec, about 2,500 msec, or about 3,000 msec. In yet other aspects of this embodiment, a defined period of time for presenting a stimulus from the second group of stimuli can be, e.g., at least 10 msec, at least 50 msec, at least 100 msec, at least 150 msec, at least 200 msec, at least 250 msec, at least 300 msec, at least 350 msec, at least 400 msec, at least 450 msec, at least 500 msec, at least 550 msec, at least 600 msec, at least 650 msec, at least 700 msec, at least 750 msec, at least 800 msec, at least 850 msec, at least 900 msec, at least 950 msec, at least 1,000 msec, at least 1,100 msec, at least 1,200 msec, at least 1,300 msec, at least 1,400 msec, at least 1,500 msec, at least 1,600 msec, at least 1,700 msec, at least 1,800 msec, at least 1,900 msec, at least 2,000 msec, at least 2,500 msec, or at least 3,000 msec. In still other aspects of this embodiment, a defined period of time for presenting a stimulus from the second group of stimuli can be, e.g., at most 10 msec, at most 50 msec, at most 100 msec, at most 150 msec, at most 200 msec, at most 250 msec, at most 300 msec, at most 350 msec, at most 400 msec, at most 450 msec, at most 500 msec, at most 550 msec, at most 600 msec, at most 650 msec, at most 700 msec, at most 750 msec, at most 800 msec, at most 850 msec, at most 900 msec, at most 950 msec, at most 1,000 msec, at most 1,100 msec, at most 1,200 msec, at most 1,300 msec, at most 1,400 msec, at most 1,500 msec, at most 1,600 msec, at most 1,700 msec, at most 1,800 msec, at most 1,900 msec, at most 2,000 msec, at most 2,500 msec, or at most 3,000 msec.

In further other aspects of this embodiment, a defined period of time for presenting a stimulus from the second group of stimuli can be from, e.g., about 10 msec to about 100 msec, about 10 msec to about 200 msec, about 10 msec to about 300 msec, about 10 msec to about 400 msec, about 10 msec to about 500 msec, about 10 msec to about 600 msec, about 10 msec to about 700 msec, about 10 msec to about 800 msec, about 10 msec to about 900 msec, about 10 msec to about 1,000 msec, about 10 msec to about 1,100 msec, about 10 msec to about 1,200 msec, about 10 msec to about 1,300 msec, about 10 msec to about 1,400 msec, about 10 msec to about 1,500 msec, about 10 msec to about 1,600 msec, about 10 msec to about 1,700 msec, about 10 msec to about 1,800 msec, about 10 msec to about 1,900 msec, about 10 msec to about 2,000 msec, about 10 msec to about 3,000 msec, about 100 msec to about 200 msec, about 100 msec to about 300 msec, about 100 msec to about 400 msec, about 100 msec to about 500 msec, about 100 msec to about 600 msec, about 100 msec to about 700 msec, about 100 msec to about 800 msec, about 100 msec to about 900 msec, about 100 msec to about 1,000 msec, about 100 msec to about 1,100 msec, about 100 msec to about 1,200 msec, about 100 msec to about 1,300 msec, about 100 msec to about 1,400 msec, about 100 msec to about 1,500 msec, about 100 msec to about 1,600 msec, about 100 msec to about 1,700 msec, about 100 msec to about 1,800 msec, about 100 msec to about 1,900 msec, about 100 msec to about 2,000 msec, about 100 msec to about 3,000 msec, about 250 msec to about 300 msec, about 250 msec to about 400 msec, about 250 msec to about 500 msec, about 250 msec to about 600 msec, about 250 msec to about 700 msec, about 250 msec to about 800 msec, about 250 msec to about 900 msec, about 250 msec to about 1,000 msec, about 250 msec to about 1,100 msec, about 250 msec to about 1,200 msec, about 250 msec to about 1,300 msec, about 250 msec to about 1,400 msec, about 250 msec to about 1,500 msec, about 250 msec to about 1,600 msec, about 250 msec to about 1,700 msec, about 250 msec to about 1,800 msec, about 250 msec to about 1,900 msec, about 250 msec to about 2,000 msec, about 250 msec to about 3,000 msec, about 500 msec to about 600 msec, about 500 msec to about 700 msec, about 500 msec to about 800 msec, about 500 msec to about 900 msec, about 500 msec to about 1,000 msec, about 500 msec to about 1,100 msec, about 500 msec to about 1,200 msec, about 500 msec to about 1,300 msec, about 500 msec to about 1,400 msec, about 500 msec to about 1,500 msec, about 500 msec to about 1,600 msec, about 500 msec to about 1,700 msec, about 500 msec to about 1,800 msec, about 500 msec to about 1,900 msec, about 500 msec to about 2,000 msec, about 500 msec to about 3,000 msec, about 750 msec to about 800 msec, about 750 msec to about 900 msec, about 750 msec to about 1,000 msec, about 750 msec to about 1,100 msec, about 750 msec to about 1,200 msec, about 750 msec to about 1,300 msec, about 750 msec to about 1,400 msec, about 750 msec to about 1,500 msec, about 750 msec to about 1,600 msec, about 750 msec to about 1,700 msec, about 750 msec to about 1,800 msec, about 750 msec to about 1,900 msec, about 750 msec to about 2,000 msec, about 750 msec to about 3,000 msec, about 1,000 msec to about 1,100 msec, about 1,000 msec to about 1,200 msec, about 1,000 msec to about 1,300 msec, about 1,000 msec to about 1,400 msec, about 1,000 msec to about 1,500 msec, about 1,000 msec to about 1,600 msec, about 1,000 msec to about 1,700 msec, about 1,000 msec to about 1,800 msec, about 1,000 msec to about 1,900 msec, about 1,000 msec to about 2,000 msec, about 1,000 msec to about 3,000 msec, about 1,250 msec to about 1,300 msec, about 1,250 msec to about 1,400 msec, about 1,250 msec to about 1,500 msec, about 1,250 msec to about 1,600 msec, about 1,250 msec to about 1,700 msec, about 1,250 msec to about 1,800 msec, about 1,250 msec to about 1,900 msec, about 1,250 msec to about 2,000 msec, about 1,250 msec to about 3,000 msec, about 1,500 msec to about 1,600 msec, about 1,500 msec to about 1,700 msec, about 1,500 msec to about 1,800 msec, about 1,500 msec to about 1,900 msec, about 1,500 msec to about 2,000 msec, about 1,500 msec to about 3,000 msec, about 2,000 msec to about 3,000 msec, or about 2,500 msec to about 3,000 msec.

Presentation of a stimulus from the second group of stimuli include an interval of time where no stimulus is presented to an individual performing the test phase. Like the pre-exposure phase, these intervals are simply gaps between the presentation of each stimulus. An interval of time between the presentation of each stimulus from the first group of stimuli is done for a defined period of time. Thus, unlike the pre-exposure phase where these intervals are optional, in the test phase, the intervals of time between stimuli is mandatory. In an aspect of this embodiment, an interval period of time between the presentation of a stimulus from the second group of stimuli can be between, e.g., about 1 msec to about 10,000 msec, about 5 msec to about 1,000 msec, about 10 msec to about 500 msec, about 15 msec to about 250 msec, about 20 msec to about 100 msec, about 25 msec to about 75 msec, or about 50 msec. In an aspect of this embodiment, an interval period of time between the presentation of a stimulus from the second group of stimuli can be between, e.g., about 10 msec to about 10,000 msec, about 50 msec to about 1,000 msec, about 100 msec to about 500 msec, about 150 msec to about 250 msec, about 100 msec to about 200 msec, about 125 msec to about 175 msec, or about 150 msec.

In other aspects of this embodiment, an interval period of time between the presentation of a stimulus from the second group of stimuli can be, e.g., about 10 msec, about 50 msec, about 100 msec, about 150 msec, about 200 msec, about 250 msec, about 300 msec, about 350 msec, about 400 msec, about 450 msec, about 500 msec, about 550 msec, about 600 msec, about 650 msec, about 700 msec, about 750 msec, about 800 msec, about 850 msec, about 900 msec, about 950 msec, about 1,000 msec, about 1,100 msec, about 1,200 msec, about 1,300 msec, about 1,400 msec, about 1,500 msec, about 1,600 msec, about 1,700 msec, about 1,800 msec, about 1,900 msec, about 2,000 msec, about 2,500 msec, or about 3,000 msec. In yet other aspects of this embodiment, an interval period of time between the presentation of a stimulus from the second group of stimuli can be, e.g., at least 10 msec, at least 50 msec, at least 100 msec, at least 150 msec, at least 200 msec, at least 250 msec, at least 300 msec, at least 350 msec, at least 400 msec, at least 450 msec, at least 500 msec, at least 550 msec, at least 600 msec, at least 650 msec, at least 700 msec, at least 750 msec, at least 800 msec, at least 850 msec, at least 900 msec, at least 950 msec, at least 1,000 msec, at least 1,100 msec, at least 1,200 msec, at least 1,300 msec, at least 1,400 msec, at least 1,500 msec, at least 1,600 msec, at least 1,700 msec, at least 1,800 msec, at least 1,900 msec, at least 2,000 msec, at least 2,500 msec, or at least 3,000 msec. In still other aspects of this embodiment, an interval period of time between the presentation of a stimulus from the second group of stimuli can be, e.g., at most 10 msec, at most 50 msec, at most 100 msec, at most 150 msec, at most 200 msec, at most 250 msec, at most 300 msec, at most 350 msec, at most 400 msec, at most 450 msec, at most 500 msec, at most 550 msec, at most 600 msec, at most 650 msec, at most 700 msec, at most 750 msec, at most 800 msec, at most 850 msec, at most 900 msec, at most 950 msec, at most 1,000 msec, at most 1,100 msec, at most 1,200 msec, at most 1,300 msec, at most 1,400 msec, at most 1,500 msec, at most 1,600 msec, at most 1,700 msec, at most 1,800 msec, at most 1,900 msec, at most 2,000 msec, at most 2,500 msec, or at most 3,000 msec.

In further other aspects of this embodiment, an interval period of time between the presentation of a stimulus from the second group of stimuli can be, e.g., about 10 msec to about 100 msec, about 10 msec to about 200 msec, about 10 msec to about 300 msec, about 10 msec to about 400 msec, about 10 msec to about 500 msec, about 10 msec to about 600 msec, about 10 msec to about 700 msec, about 10 msec to about 800 msec, about 10 msec to about 900 msec, about 10 msec to about 1,000 msec, about 10 msec to about 1,100 msec, about 10 msec to about 1,200 msec, about 10 msec to about 1,300 msec, about 10 msec to about 1,400 msec, about 10 msec to about 1,500 msec, about 10 msec to about 1,600 msec, about 10 msec to about 1,700 msec, about 10 msec to about 1,800 msec, about 10 msec to about 1,900 msec, about 10 msec to about 2,000 msec, about 10 msec to about 3,000 msec, about 100 msec to about 200 msec, about 100 msec to about 300 msec, about 100 msec to about 400 msec, about 100 msec to about 500 msec, about 100 msec to about 600 msec, about 100 msec to about 700 msec, about 100 msec to about 800 msec, about 100 msec to about 900 msec, about 100 msec to about 1,000 msec, about 100 msec to about 1,100 msec, about 100 msec to about 1,200 msec, about 100 msec to about 1,300 msec, about 100 msec to about 1,400 msec, about 100 msec to about 1,500 msec, about 100 msec to about 1,600 msec, about 100 msec to about 1,700 msec, about 100 msec to about 1,800 msec, about 100 msec to about 1,900 msec, about 100 msec to about 2,000 msec, about 100 msec to about 3,000 msec, about 250 msec to about 300 msec, about 250 msec to about 400 msec, about 250 msec to about 500 msec, about 250 msec to about 600 msec, about 250 msec to about 700 msec, about 250 msec to about 800 msec, about 250 msec to about 900 msec, about 250 msec to about 1,000 msec, about 250 msec to about 1,100 msec, about 250 msec to about 1,200 msec, about 250 msec to about 1,300 msec, about 250 msec to about 1,400 msec, about 250 msec to about 1,500 msec, about 250 msec to about 1,600 msec, about 250 msec to about 1,700 msec, about 250 msec to about 1,800 msec, about 250 msec to about 1,900 msec, about 250 msec to about 2,000 msec, about 250 msec to about 3,000 msec, about 500 msec to about 600 msec, about 500 msec to about 700 msec, about 500 msec to about 800 msec, about 500 msec to about 900 msec, about 500 msec to about 1,000 msec, about 500 msec to about 1,100 msec, about 500 msec to about 1,200 msec, about 500 msec to about 1,300 msec, about 500 msec to about 1,400 msec, about 500 msec to about 1,500 msec, about 500 msec to about 1,600 msec, about 500 msec to about 1,700 msec, about 500 msec to about 1,800 msec, about 500 msec to about 1,900 msec, about 500 msec to about 2,000 msec, about 500 msec to about 3,000 msec, about 750 msec to about 800 msec, about 750 msec to about 900 msec, about 750 msec to about 1,000 msec, about 750 msec to about 1,100 msec, about 750 msec to about 1,200 msec, about 750 msec to about 1,300 msec, about 750 msec to about 1,400 msec, about 750 msec to about 1,500 msec, about 750 msec to about 1,600 msec, about 750 msec to about 1,700 msec, about 750 msec to about 1,800 msec, about 750 msec to about 1,900 msec, about 750 msec to about 2,000 msec, about 750 msec to about 3,000 msec, about 1,000 msec to about 1,100 msec, about 1,000 msec to about 1,200 msec, about 1,000 msec to about 1,300 msec, about 1,000 msec to about 1,400 msec, about 1,000 msec to about 1,500 msec, about 1,000 msec to about 1,600 msec, about 1,000 msec to about 1,700 msec, about 1,000 msec to about 1,800 msec, about 1,000 msec to about 1,900 msec, about 1,000 msec to about 2,000 msec, about 1,000 msec to about 3,000 msec, about 1,250 msec to about 1,300 msec, about 1,250 msec to about 1,400 msec, about 1,250 msec to about 1,500 msec, about 1,250 msec to about 1,600 msec, about 1,250 msec to about 1,700 msec, about 1,250 msec to about 1,800 msec, about 1,250 msec to about 1,900 msec, about 1,250 msec to about 2,000 msec, about 1,250 msec to about 3,000 msec, about 1,500 msec to about 1,600 msec, about 1,500 msec to about 1,700 msec, about 1,500 msec to about 1,800 msec, about 1,500 msec to about 1,900 msec, about 1,500 msec to about 2,000 msec, about 1,500 msec to about 3,000 msec, about 2,000 msec to about 3,000 msec, or about 2,500 msec to about 3,000 msec.

A second group of stimuli comprises a plurality of stimuli. In an aspect of this embodiment, a second group of stimuli disclosed herein comprises at least one preexposed stimuli, a non-preexposed stimulus, a target stimulus, and the one or more neutral stimuli. A non-preexposed stimulus is a stimulus which is not presented during the pre-exposure phase and represents a novel stimulus that occurs only during the test phase. It is predictive of the occurrence of the target stimulus. A target stimulus is a stimulus which is not presented during the pre-exposure phase and represents a novel stimulus occurring only during the test phase. It is the stimulus that an individual is trying to anticipate the occurrence of during the test phase. The target stimulus can only be correctly anticipated by an individual following a preexposed or a non-preexposed stimulus and not a neutral stimulus. A preexposed stimulus and neutral stimulus are the same as those in presented in the preexposure phase proceure.

A group assignment method, a psychotic disorder determination method, and a therapy recommendation method disclosed herein measures a time associated with a target anticipated response of the individual to each stimulus from a second group of stimuli disclosed herein. A response to a target stimulus disclosed herein of less than the sum of the presentation time and interval time according to a second set of directions disclosed is indicative that the individual anticipated the occurrence of the target stimulus. In aspects of this embodiment, an individual is scored as anticipating the occurrence of a target stimulus if the sum of the presentation time and interval time is, e.g., less than 550 msec, less than 750 msec, less than 950 msec, less than 1,050 msec, less than 1,150 msec, less than 1,350 msec, less than 1,550 msec, less than 1,750 msec, less than 1,950 msec, less than 2,150 msec, less than 2,350 msec, or less than 2,550 msec, then the individual anticipated the occurrence of the target stimulus.

A response to a target stimulus disclosed herein of equal to or more than the sum of the presentation time and interval time according to a second set of directions disclosed herein is indicative that the individual failed to anticipate the occurrence of the target stimulus. In aspects of this embodiment, an individual is scored as failing to anticipate the occurrence of a target stimulus if the sum of the presentation time and interval time is, e.g., 550 msec or more, 750 msec or more, 950 msec or more, 1,050 msec or more, 1,150 msec or more, 1,350 msec or more, 1,550 msec or more, 1,750 msec or more, 1,950 msec or more, 2,150 msec or more, 2,350 msec or more, 2,550 msec or more, then the individual failed to anticipate the occurrence of the target stimulus.

A group assignment method, a psychotic disorder determination method, and a therapy recommendation method disclosed herein comprises a step of measuring a latent inhibition response of the individual to calculate a latent inhibition score to determine whether the individual exhibits an attenuated latent inhibition response, a normal latent inhibition response or an enhanced latent inhibition response. The latent inhibition score phase of the application 500 is illustrated in greater detail in FIG. 5. The patient's P test data from the test results dataset is retrieved from the database, step 502. The latent inhibition score $LIS_P$ for the patient P is determined using the latent inhibition algorithm to at least a portion of the test results dataset, such as the response time $t_{Rn}$, and optionally, the nonresponses or untimely responses, step 504. Outliers in the dataset may be manually or automatically removed to improve the assessment accuracy. The latent inhibition score $LIS_P$ calculated is compared to a reference latent inhibition score $LIS_R$ to determine an outcome assessment for the patient P, step 505. In step 506, the application determines whether $LIS_P=LIS_R$, that is, equal exactly or within a predetermined range of one another. If $LIS_P=LIS_R$, then the patient P is classified as having a normal latent inhibition response, step 508. In step 510, the application determines whether $LIS_P>LIS_R$. If $LIS_P>LIS_R$, then the patient P is classified as having an enhanced latent inhibition response, step 512. In step 514, the application determines whether $LIS_P<LIS_R$. If $LIS_P<LIS_R$, then the patient P is classified as having an attenuated latent inhibition response, step 516. The outcome assessment data for the patient P is recorded in the patient dataset, step 518.

Figure 5:
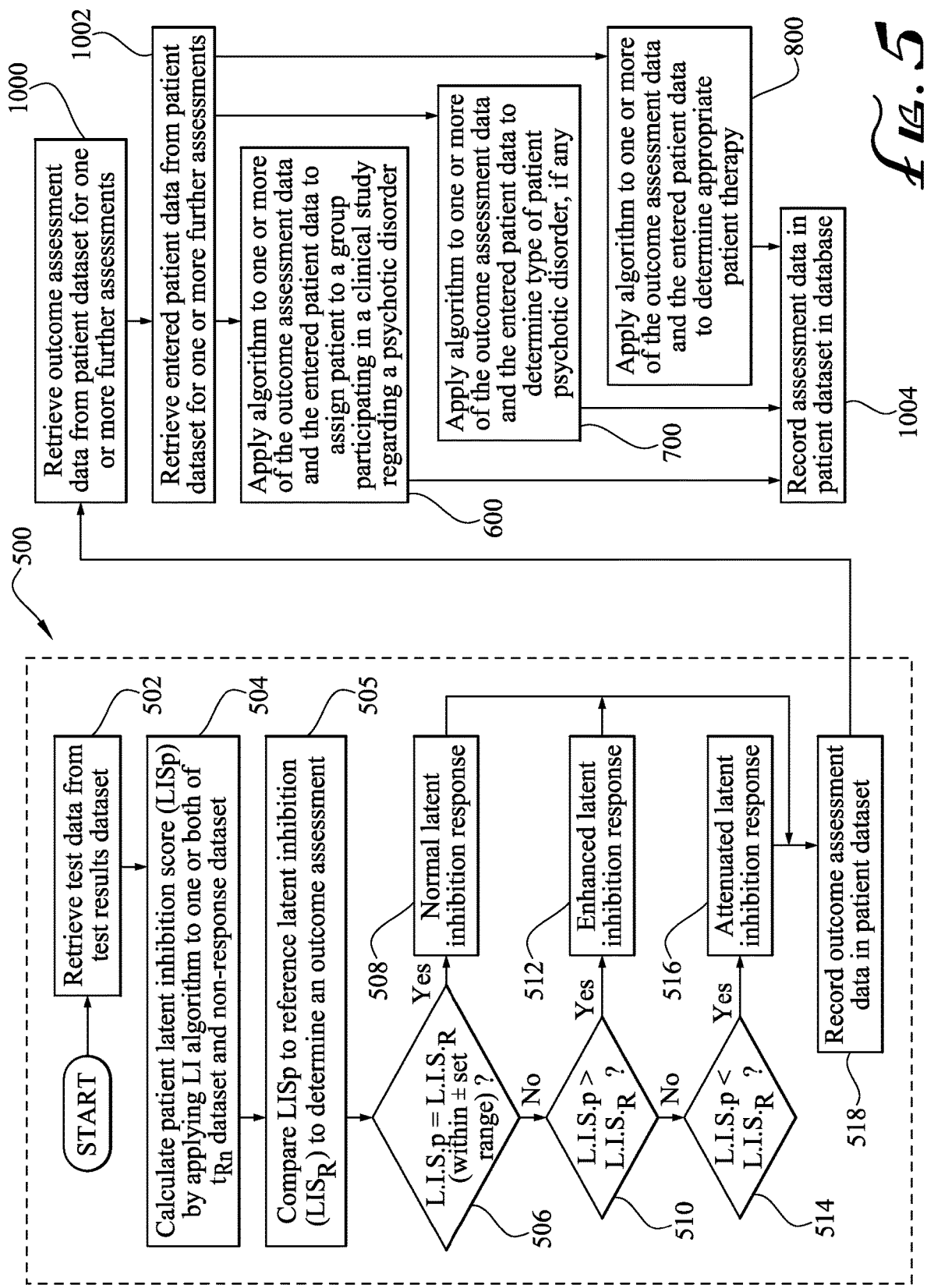
FIG. 5 is a flow chart of the latent inhibition score portion of the present computer implemented assessment method of FIG. 2.

As seen in FIG. 2, the present invention is, in one aspect thereof, a method 200 that broadly invokes an algorithm for performing a latent inhibition task. The algorithm is embodied in one or more data processing functions that are executed by a plurality of software elements. The latent inhibition task is performed in a pre-exposure phase (referred to herein as the pre-exposure portion 300), a test phase (referred to herein as the text portion 400), and a measurement and application phase (referred to herein as the latent inhibition scoring portion 500) in which a latent inhibition score is calculated to model a patient's response to presentations of stimulus, and used to determine a clinical study group assignment for a patient, a patient's psychotic disorder, and an appropriate therapeutic treatment for the patient. It is to be understood that the measurement and application phase may also include calculating a working memory score, and that either or both of a latent inhibition score or a working memory score may be calculated by the algorithm. FIG. 3 is a flow chart of steps in the pre-exposure phase, while FIG. 4 is a flow chart of steps in the test phase. FIG. 5 is a flow chart of steps in determining a clinical study group assignment for a patient, and FIG. 6 and FIG. 7 are matrices of diagnosis and treatment recommendations according to latent inhibition scores.

The algorithm may be executed by hardware components, such as one or more servers, that are configured to execute a plurality of data processing modules. The hardware components and software elements are components within a computing environment that may also include one or more processors as well as the plurality of additional software elements and hardware components. The one or more processors, and the various software and hardware, are configured to execute program instructions routines, sub-routines, and other software elements stored within at least one computer-readable non-transitory storage medium to at least perform the analytical functions described herein that are part of the algorithm performing the latent inhibition task, and embodied within the plurality of data processing modules.

The algorithm performs a number of specific functions while executing the pre-exposure phase and the test phase of the latent inhibition task, which as a general overview assesses the degree to which patients detect that a newly-introduced target stimulus is associated with a novel non-target stimulus, versus detecting that it is associated with a familiar non-target stimulus. The latent inhibition task begins with a familiarization or pre-exposure block that allows the patient to become familiar with several non-target stimuli. Next, the main or test block sees a novel non-target stimulus added, in addition to the introduction of the target stimulus.

The pre-exposure and text blocks are presented via a graphical user interface having touch-responsive capability. In terms of its screen layout, presentation and button operation, the latent inhibition task is similar to a rapid visual processing test (RVP) of sustained visual attention, during non-training phases.

In the pre-exposure and testing blocks of the latent inhibition task algorithm, stimuli are restricted to text values; in typical task variants, each stimulus is a single capital letter. Quotations may be used herein to indicate variants, the selection of which is used to indicate a configurable facet of the implementation. These are equivalent to 'variables' in software code and represent different portions of the algorithm performed in the present invention that may or may not be called, depending at least in part on the objectives of the administrator of the test. Regardless, the values taken on are specified by the task variant in force, or where not overridden therein, by values given in Tables 1, 2 and 3.

TABLE 1

Values for Variables utilized within Algorithm for Assessing Latent Inhibition

| Variable Name | Default | 5 (PE) | 6 (NPE) |
|---|---|---|---|
| preMethod | 2back | | |
| preOccurrences | 15 | 20 | 0 |
| mainOccurrencesNoTarget | 64 | 0 | 0 |
| MainOccurrencesThenTarget | 5 | 20 | 20 |
| avoidRepeats | true | | |
| stimulusDisplay | 1000 | | |
| postStimulusBlank | 150 | | |
| preemptDelay | 100 | | |
| stimulusTextHeight | 23 | | |

TABLE 2

Values for Variables utilized within Algorithm for Assessing Latent Inhibition

| Variable Name | Standard | 5 (PE) | 6 (NPE) |
|---|---|---|---|
| preMethod | 0back | | |
| preOccurrences | 0 | 20 | 0 |
| mainOccurrencesNoTarget | 64 | 0 | 0 |
| MainOccurrencesThenTarget | 5 | 20 | 20 |
| avoidRepeats | true | | |
| stimulusDisplay | 1000 | | |
| postStimulusBlank | 150 | | |
| preemptDelay | 100 | | |
| stimulusTextHeight | 23 | | |

TABLE 3

Values for Variables utilized within Algorithm for Assessing Latent Inhibition

| Variable Name | One-Back | 5 (PE) | 6 (NPE) |
|---|---|---|---|
| preMethod | 1back | | |
| preOccurrences | 15 | 20 | 0 |
| mainOccurrencesNoTarget | 64 | 0 | 0 |
| MainOccurrencesThenTarget | 5 | 20 | 20 |
| avoidRepeats | true | | |
| stimulusDisplay | 1000 | | |
| postStimulusBlank | 150 | | |
| preemptDelay | 100 | | |
| stimulusTextHeight | 23 | | |

The pre-exposure blocks may operate in one of 3 modes as indicated in Tables 1, 2 and 3. The modes may be a default mode, a standard mode, and a one-back mode. The values presented for each of these modes dictate the presentation of the pre-exposure by the latent inhibition algorithm, as follows below. Variable names in Tables 1, 2 and 3 refer to different portions of the tasks, such as "preInstructions" etc.

Referring to Tables 1, 2 and 3 where there are multiple (i) values for a variable, a separate column is used for each (i) against which the variable's values differs. For clarity, the legends 'PE' and 'NPE' point out, respectively, the pre-exposure and non-pre-exposure stimulus (i.e. respectively the familiar and the non-familiar stimulus configured to precede the target stimulus most frequently).

During the pre-exposure phase, button operation on the graphical user interface includes a button that is drawn at a bottom center of the touchable screen. To make a button press, the patient touches inside the button (which initially appears untouched), which is then re-drawn to indicate that it has been touched. When the patient stops touching the button, or drags it outside of its bounds, the algorithm redraws the button so that it returns to its untouched state. There is no other effect on the latent inhibition task. At the next step of this pre-exposure phase, the button is surrounded by an invisible border of approximately 5 mm thickness (relative to a typical tablet screen). It is to be understood that any size of such a border may be displayed, however. Regardless, touches within this border are counted as touches to the button.

Prior to each block, instructions are displayed on the touch screen interface. An arrow button is displayed at the bottom of the touch screen, typically appearing below the instructions. When the patient taps it, the algorithm removes the instructions and the block of pre-exposure stimuli presentations begin.

Depending on the selected variable for displaying text on the screen in a particular font, a button may or may not be displayed at the outset to the patient signaling the beginning of pre-exposure stimuli. For example, if "preMethod" has been selected with a variable of "1back" or "2back", then a button is displayed; otherwise, no button is displayed. Regardless, consecutive stimulus presentations are initiated. The stimuli presented are drawn in turn from a randomly shuffled list, comprised of "preOccurrences(i)" which represent occurrences of stimulus(i) for each defined stimulus(i) (i>0). If "avoidRepeats" has been selected, the list is further amended such that the same stimulus is never presented twice in a row. This is achieved by inspecting each stimulus in turn and, where it causes a repeat of the preceding stimulus, moving it to a random new position in the sequence where it no longer causes a repeat (i.e. where it neither follows nor precedes the same stimulus).

Each stimulus is presented for display for a preset period of time depending on the variable, typically expressed in milliseconds. For example, where "stimulusDisplay" is the variable, the preset time period is 1000 msec. The stimulus is then offset, and no stimulus is displayed for another preset period of time, such as the time period specific by "postStimulusBlank." The stimulus size is a preset height, for example that specified by the variable "stimulusTextHeight."

When button presses are made by the patient, they are associated with a perceived presentation. A given presentation is the perceived presentation from "preemptDelay" ms after it is displayed on the screen, until "preemptDelay" ms after the next stimulus is displayed on the screen. Before "preemptDelay" ms from the first stimulus in the block, and from "preemptDelay" ms after the last stimulus in the block, there is no perceived presentation and any presses made by the patient on the touch screen are ignored. The pre-exposure block ends "preemptDelay" ms after the last stimulus of the block is offset.

The main or testing block, or phase, of the latent inhibition task algorithm is executed in the same manner as the pre-exposure block, except for the differences described as follows. In this phase, the button is always displayed to the patient.

The stimuli to be presented in this test phase of the algorithm are drawn in turn from a randomly shuffled list, comprised of "mainOccurrencesNoTarget(i)" occurrences of stimulus(i) for each defined stimulus(i) (i>0), and "mainOccurrencesThenTarget(i)" occurrences of stimulus(i) for each defined stimulus(i) (i>0), with each occurrence being immediately followed by a single occurrence of "targetStimulus". Note that during the shuffling, whenever a stimulus that is followed by a "targetStimulus" is moved, the target is moved along with that stimulus, such that it still succeeds the moved stimulus in the shuffled sequence.

As during the pre-exposure phase, if "avoidRepeats" is the default, the list of stimuli is further amended such that the same stimulus is never presented twice in a row; however, where the moved stimulus was followed by a target in the original sequence, the target is moved along with that stimulus, such that it still succeeds the moved stimulus in the amended sequence.

Returning to the discussion of variables and defaults for the pre-exposure and test blocks, during the presentation of stimuli in "preInstructions" in the pre-exposure block, the patient is presented with text that may be, in one example, In this task you will see a sequence of letters appearing on the screen.
Your task is to press the response button at the bottom of the screen
each time the current letter is the same as the one that was presented before last,
which is 2 positions back in the sequence.
Otherwise, do not respond.
When this task ends, you will be given a new set of instructions.
Press the arrow below when you are ready to begin.

During the main or test block, different text appears on the touch screen during "preInstructions". The patient is presented with text that reads, for example, as In this task you will see a sequence of letters appearing on the screen.
Your task is to try and predict when a letter X is going to appear.
If you think you know when the X will appear then you can press the response button early in the sequence, which is before the X appears on screen.
Alternatively, if you are unable to do this please press the response button as quickly as possible when you see the letter X. There may be more than one rule that predicts the X.
Please try to be as accurate as you can, but do not worry about making the occasional error.
If you understand the task, please press the arrow below when you are ready to begin.

For the above text, symbols are used when delineating text to be shown for various ones of the variables, and where the symbol d appears in software code, this indicates that a new line should be started on the screen (note that the symbol is not displayed on the screen to the patient). These are the only points at which text will be wrapped on-screen, regardless of how the text is wrapped in this specification.

During the testing phase, the latent inhibition task algorithm measures a response of the patient to stimuli presented. Protocols for measuring a response time available for task variants in the algorithm are defined below. Variables in quotation marks indicate a configurable option of the measurement protocols. This is equivalent to a 'variable' in software code; where surrounded by angle brackets, substitute the actual value of the variable when reading the text. The values taken on by these variables are specified in the measure definitions of the task variant in force. Note that measures are always incalculable when the task is aborted.

Perceived presentations' refers to the presentation displayed to the subject except where the relevant subject interaction occurred during the pre-empt period, in which case it refers to the prior presentation. Any interactions during the pre-empt period of the first presentation are ignored. This is consistent with the approach taken in the rapid visual processing test (RVP) of sustained visual attention.

The algorithm has several analytical functions available for modeling the response time measured as a stimulus response latency. These analytical functions apply statistical analyses for such a model that include count, mean, median and standard deviation, and the algorithm may utilize one or more of these analytical functions when modeling a patient's response time. Together these statistical analyses are used to evaluate ranges of behavior in the patient's response that are indicative of normal, attenuated, or enhanced latent inhibition, either in the amount of the patient's responses, or in relation to a central tendency of the responses and the distance from such a central tendency.

Stimulus response latency during the main (not pre-exposure) block on perceived presentations of the selected type is measured from the presentation of the stimulus to the first button tap by the subject. Where the present invention applies a counting function, the algorithm counts the number of presentations on which such a response occurred, regardless of the exact reaction time within the presentation. Where the present invention applies a mean, median, or standard deviation function, the model performs these calculations on the total number of responses.

Presentation type for a latency response stimulus may occur in a number of different forms. This may include filler, a pre-exposure (P.E.) stimulus where the pre-target stimulus that was shown during pre-exposure), a non pre-exposure (N.P.E.) where the pre-target stimulus that was not shown during pre-exposure, target, target-after-P.E., target-after-N.P.E., and target-after-filler.

Target response latency during the main (not pre-exposure) block is measured from the first button tap made during each P.E./N.P.E. target period. The P.E./N.P.E. target period runs from the start of the P.E./N.P.E. stimulus' perceived presentation to the end of the subsequent target stimulus' perceived presentation, measured from the onset of the P.E./N.P.E. stimulus. Again, the algorithm has several analytical functions available for modeling the response time measured as a target response latency. These analytical functions apply statstical analyses that include count, mean, median and standard deviation, and the algorithm may utilize one or more of these analytical functions when modeling a patient's response time for target stimuli.

Presentation type for a target stimulus is as noted above either a pre-exposure (P.E.) or non pre-exposure (N.P.E.) stimulus. For a P.E. stimulus, the pre-target stimulus is that which was shown during pre-exposure, any presses of a button during the subsequent target are also included. For a N.P.E. stimulus, the pre-target stimulus is that which was not shown during pre-exposure, and as with P.E., any presses during the subsequent target are also included.

An assessment of working memory requires evaluating pre-exposure hits and pre-exposure false alarms. Note from FIG. 3 that n-back responses relate to responses to stimuli presented n positions prior, and that instructions may or may not require n-back responses, such that a response input may be required for each P.E. stimulus displayed, or an n-back response is required for a P.E. stimulus that matches a prior P.E. stimulus presented n positions prior. Pre-exposure hits are evaluated by counting the number of n-back 'go' perceived presentations during the pre-exposure block, on which the patient tapped the button. Note that this would be zero in the case of pre-exposure blocks with no n-backs. Pre-exposure false alarms are evaluated by counting the number of n-back 'stop' perceived presentations during the pre-exposure block on which the patient tapped the button. Note that this would also be zero in the case of pre-exposure blocks with no n-backs.

Regardless of the presentation type or the analytical function used to evaluate response time, the algorithm uses the information obtained from these analytical functions to calculate a latent inhibition score and a working memory score. Each of these may be used in the present invention to arrive at determinations of a clinical study group assignment for a patient, a patient's psychotic disorder, and an appropriate therapeutic treatment for the patient, as noted above.

A patient's latent inhibition score may be calculated by measuring the target response latency for the PE stimulus, measuring the target response latency for the NPE stimulus, and computing a difference between the two—in other words, P.E. minus N.P.E. This may be performed regardless of the analytical function applied to measure latent inhibition.

A patient's working memory score may be calculated by compiling a total number of hits, and total number of false alarms, and computing a difference between the two—in other words, hits minus false alarms. As with the latent inhibition score, this may be performed regardless of the analytical function applied to measure latent inhibition.

The present invention may incorporate one or more techniques of machine learning, and apply proprietary rules identifying such techniques of machine learning to analyze the stimulus latency response and target latency response developed from modeling a patient's reactions to stimuli presented. Machine learning is an application of artificial intelligence in which algorithms are deployed to evaluate data, learn from that data, and make informed decisions based on what was learned. Specific machine learning models can be developed to focus on particular issues to be solved by such informed decisions. In the present invention, the algorithm may be configured to apply such techniques to improve upon the outcomes determined by the latent inhibition score and the working memory score, by inferring distinctions based on past responses to displays of text. The present invention may therefore apply the one or more techniques of machine learning to improve upon the resulting determinations of a clinical study group assignment for a patient, a patient's psychotic disorder, and an appropriate therapeutic treatment for the patient.

In step 1000, the application retrieves the outcome assessment data for the patient P from the patient dataset for further assessment. Patient personal data (such as medical history, personal data, etc.) is entered and/or retrieved from the patient dataset in step 1002, for use with the outcome assessment data for further assessment. In step 600, the application algorithm is applied to one or both of the outcome assessment data and the patient personal data to determine an assignment of the patient P to a group participating in a clinical study regarding a psychotic disorder. In step 700, the application algorithm is applied to one or both of the outcome assessment data and the patient personal data to determine the type of patient psychotic disorder, if any. In step 800, the application algorithm is applied to one or both of the outcome assessment data and the patient personal data to determine an appropriate patient therapy. The assessment data from one or more of steps 600, 700, and 800 are recorded in the patient dataset in the database.

In one embodiment, a latent inhibition score is calculated using one or more reaction times. In an aspect of this embodiment, a latent inhibition score is calculated by i) calculating a first average time based on each target anticipated response measured when a target stimulus was presented after presentation of the non-preexposed stimulus; ii) calculating a second average time based on each target anticipated response measured when the target stimulus was presented after presentation of the preexposed stimulus; and iii) calculating the latent inhibition score by subtracting the second average time by the first average time.

In an aspect of this embodiment, a latent inhibition score is calculated using one or more reaction times by i) calculating a first average time based on each target anticipated response measured when the target stimulus was presented after presentation of the non-preexposed stimulus; ii) calculating a second average time based on each target anticipated response measured when the target stimulus was presented after presentation of the preexposed stimulus; and iii) calculating the latent inhibition score by subtracting the first average time by the second average time.

In an aspect of this embodiment, a latent inhibition score is calculated using one or more reaction times by i) calculating a first average time based on each target anticipated response measured when the target stimulus was presented after presentation of the non-preexposed stimulus; ii) calculating a second average time based on each target prediction response measured when the target stimulus was presented after presentation of the preexposed stimulus; and iii) calculating the latent inhibition score by determining whether the first average time is slower or faster than the second average time.

In an aspect of this embodiment, a latent inhibition score is calculated using one or more reaction times by i) pairing each target anticipatory response time based on the non-preexposed stimulus with a target anticipatory response time based on the preexposed stimulus; ii) calculating whether a paired target anticipatory response time based on the non-preexposed stimulus was faster relative to its paired target anticipatory response time based on the preexposed stimulus; and iii) calculating the latent inhibition score by determining (a) the total number of paired target anticipatory response times based on the non-preexposed stimulus that were higher relative to their paired target anticipatory response time based on the preexposed stimulus, (b) the total number of paired target anticipatory response times based on the non-preexposed stimulus that were lower relative to their paired target anticipatory response time based on the preexposed stimulus, or (c) both (a) and (b).

In one embodiment, a latent inhibition score is calculated using the number of anticipatory responses. In an aspect of this embodiment, a latent inhibition score is calculated by i) calculating a first average number of anticipatory responses based on each target anticipated response measured when the target stimulus was presented after presentation of the non-preexposed stimulus; ii) calculating a second average number of anticipatory responses based on each target anticipated response measured when the target stimulus was presented after presentation of the preexposed stimulus; and iii) calculating the latent inhibition score by subtracting the second average number of anticipatory responses by the first average number of anticipatory responses.

In an aspect of this embodiment, a latent inhibition score is calculated using the number of anticipatory responses by i) calculating a first average number of anticipatory responses based on each target anticipated response measured when the target stimulus was presented after presentation of the non-preexposed stimulus; ii) calculating a second average number of anticipatory responses based on each target anticipated response measured when the target stimulus was presented after presentation of the preexposed stimulus; and iii) calculating the latent inhibition score by subtracting the first average number of anticipatory responses by the second average number of anticipatory responses.

In an aspect of this embodiment, a latent inhibition score is calculated using the number of anticipatory responses by i) calculating a first average number of anticipatory responses based on each target anticipated response measured when the target stimulus was presented after presentation of the non-preexposed stimulus; ii) calculating a second average number of anticipatory responses based on each target anticipated response measured when the target stimulus was presented after presentation of the preexposed stimulus; and iii) calculating the latent inhibition score by determining whether the first average number of anticipatory responses is lower or higher than the second average number of anticipatory responses.

In an aspect of this embodiment, a latent inhibition score is calculated using the number of anticipatory responses by i) pairing each target anticipatory response based on the non-preexposed stimulus with a target anticipatory response based on the preexposed stimulus; ii) calculating whether a paired target anticipatory response time based on the non-preexposed stimulus was faster relative to its paired target anticipatory response time based on the preexposed stimulus; and iii) calculating the latent inhibition score by determining (a) the total number of paired target anticipatory response times based on the non-preexposed stimulus that were higher relative to their paired target anticipatory response time based on the preexposed stimulus, (b) the total number of paired target anticipatory response times based on the non-preexposed stimulus that were lower relative to their paired target anticipatory response time based on the preexposed stimulus, or (c) both (a) and (b).

In one embodiment, a latent inhibition score is calculated using the percent of anticipatory responses. In an aspect of this embodiment, a latent inhibition score is calculated using the percent of anticipatory responses by i) calculating a first percent of anticipatory responses based on each target anticipated response measured when the target stimulus was presented after presentation of the non-preexposed stimulus; ii) calculating a second percent of anticipatory responses based on each target anticipated response measured when the target stimulus was presented after presentation of the preexposed stimulus; and iii) calculating the latent inhibition score by subtracting the second percent of anticipatory responses by the first percent of anticipatory responses.

In an aspect of this embodiment, a latent inhibition score is calculated using the percent of anticipatory responses by i) calculating a first percent of anticipatory responses based on each target anticipated response measured when the target stimulus was presented after presentation of the non-preexposed stimulus; ii) calculating a second percent of anticipatory responses based on each target anticipated response measured when the target stimulus was presented after presentation of the preexposed stimulus; and iii) calculating the latent inhibition score by subtracting the first percent of anticipatory responses by the second percent of anticipatory responses.

In an aspect of this embodiment, a latent inhibition score is calculated using the percent of anticipatory responses by i) calculating a first percent of anticipatory responses based on each target anticipated response measured when the target stimulus was presented after presentation of the non-preexposed stimulus; ii) calculating a second percent of anticipatory responses based on each target anticipated response measured when the target stimulus was presented after presentation of the preexposed stimulus; and iii) calculating the latent inhibition score by determining whether the first percent of anticipatory responses is lower or higher than the second percent of anticipatory responses.

In one embodiment, a latent inhibition score is calculated by comparing the latent inhibition score to a reference score comprising a standard range of latent inhibition scores. A reference score can be based on values obtained from normal individuals, values obtained from different types of patients, and/or values obtained from the same individual on one or more prior testings. A standard range latent inhibition scores can be based on a plurality of healthy individuals. In aspects of this embodiment, a plurality of healthy individuals can be, e.g., about 20 or more individuals, about 30 or more individuals, about 40 or more individuals, about 50 or more individuals, about 60 or more individuals, about 70 or more individuals, about 80 or more individuals, about 90 or more individuals, or about 100 or more individuals. A latent inhibition score calculated above a reference score is indicative of an enhanced latent inhibition response. a latent inhibition score calculated within a standard range latent inhibition scores of a reference score is indicative a normal latent inhibition response. A latent inhibition score calculated below A reference score is indicative of an attenuated latent inhibition response.

In one embodiment, a latent inhibition score is calculated using an accuracy-sensitivity d' score. In an aspect of this embodiment, a latent inhibition score is calculated using an accuracy-sensitivity d' score by i) calculating a first d' score of anticipatory responses based on each target anticipated response measured when the target stimulus was presented after presentation of the non-preexposed stimulus; ii) calculating a second d' score of anticipatory responses based on each target anticipated response measured when the target stimulus was presented after presentation of the preexposed stimulus; and iii) calculating the latent inhibition score by subtracting the second d' score of anticipatory responses by the first d' score of anticipatory responses. A first d' score and a second d' score are calculated by: i) calculating a hit rate by dividing the totaling the number of correctly identified back targets by the total number of back targets; ii) calculating a false alarm rate, by dividing the number of responses for stimuli erroneously identified as back targets by the total number of back targets; and iii) applying a z-transformation to the hit rate and the false alarm rate and subtracting the resulting transformed false alarm rate from the resulting transformed hit rate to obtain the d' score.

A group assignment method, a psychotic disorder determination method, and a therapy recommendation method disclosed herein may further include evaluating working memory of the individual. In one embodiment, working memory can be evaluated in a pre-exposure phase disclosed herein by providing instructions which require an individual to respond to a current stimulus of the first group of stimuli only if the current stimulus is the same as a stimulus shown one position back in a sequence of the first group of stimuli. In one embodiment, working memory can be evaluated in a pre-exposure phase disclosed herein by providing instructions which require the individual to respond to a current stimulus of the first group of stimuli only if the current stimulus is the same as a stimulus shown two positions back in a sequence of the first group of stimuli.

In one embodiment, working memory is evaluated by: i) counting the number of pre-exposure responses presented based on the presentation back stimulus; ii) counting the number of pre-exposure responses selected correctly by the individual based on the presentation back stimulus; and iii) calculating the percent of pre-exposure responses selected correctly by the individual, wherein 50% or more is indicative of a working memory.

In one embodiment, working memory is evaluated by: i) counting the number of pre-exposure responses selected incorrectly by the individual based on the presentation back stimulus; and ii) calculating the percent of pre-exposure responses selected incorrectly by the individual, wherein 50% or more is indicative of impaired working memory.

In one embodiment, working memory is evaluated by calculating the average reaction time of pre-exposure responses selected incorrectly by the individual.

In one embodiment, working memory is evaluated by calculating a d' score of pre-exposure responses presented based on the presentation of back stimulus.

Once a latent inhibition score is calculated by a group assignment method, a psychotic disorder determination method, or a therapy recommendation method disclosed herein, this calculation is used as a basis to make an outcome assessment. Although each method generates an outcome assessment the details of that assessment are method specific.

With respect to a group assignment method disclosed herein an outcome assessment comprises a step of assigning the individual to a group designated by the clinical study. In one embodiment, an individual is assigned to a group based on whether a latent inhibition score of the individual is indicative of an attenuated latent inhibition response, a normal latent inhibition response, or an enhanced latent inhibition response. In one embodiment, when working memory is also measured, an individual is assigned to a group based on whether the latent inhibition score of the individual is indicative of an attenuated latent inhibition response, a normal latent inhibition response, or an enhanced latent inhibition response and whether the individual exhibits a deficit in working memory or not.

With respect to a psychotic disorder determination method disclosed herein an outcome assessment comprise calculating a psychotic disorder of the individual (FIG. 6).

In one embodiment, an outcome assessment of psychotic disorder determination method disclosed herein pertains to whether an individual is at an ultra-high risk for a psychotic disorder. In aspects of this embodiment, an outcome assessment indicates that an individual is currently at an ultra-high risk for the psychotic disorder when an attenuated latent inhibition response is calculated by the method and information inputted into the method indicates that this is an initial assessment, the individual is not currently experiencing psychotic symptoms, the individual has no history of a psychotic disorder, and the individual has no history of resistant to anti-psychotic drug treatment. In other aspects of this embodiment, an outcome assessment indicates that an individual is not currently at an ultra-high risk for the psychotic disorder when a normal latent inhibition response is calculated by the method and information inputted into the method indicates that this is an initial assessment, the individual is not currently experiencing psychotic symptoms, the individual has no history of a psychotic disorder, and the individual has no history of resistant to anti-psychotic drug treatment. In yet other aspects of this embodiment, an outcome assessment indicates that an individual is currently at an ultra-high risk for the psychotic disorder when an enhanced latent inhibition response is calculated by the method and information inputted into the method indicates that this is an initial assessment, the individual is not currently experiencing psychotic symptoms, the individual has no history of a psychotic disorder, and the individual has no history of resistant to anti-psychotic drug treatment.

In other aspects of this embodiment, when working memory is also measured, an outcome assessment indicates that an individual is currently at an ultra-high risk for the psychotic disorder when an attenuated latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment. In other aspects of this embodiment, when working memory is also measured, an outcome assessment indicates that an individual is not currently at an ultra-high risk for the psychotic disorder when an attenuated latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment, and there is not a deficit in working memory. In yet other aspects of this embodiment, when working memory is also measured, an outcome assessment indicates that an individual is currently at an ultra-high risk for the psychotic disorder when a normal latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment, and there is a deficit in working memory. In yet other aspects of this embodiment, when working memory is also measured, an outcome assessment indicates that an individual is not currently at an ultra-high risk for the psychotic disorder when a normal latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment, and there is not a deficit in working memory. In still other aspects of this embodiment, when working memory is also measured, an outcome assessment indicates that an individual is currently at an ultra-high risk for the psychotic disorder when an enhanced latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment, and there is a deficit in working memory. In still other aspects of this embodiment, when working memory is also measured, an outcome assessment indicates that an individual is not currently at an ultra-high risk for the psychotic disorder when an enhanced latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment, and there is not a deficit in working memory.

In one embodiment, an outcome assessment of psychotic disorder determination method disclosed herein pertains to whether an individual is suffering a first episode of the psychotic disorder. In aspects of this embodiment, an outcome assessment indicates that an individual is suffering a first episode of the psychotic disorder when an attenuated latent inhibition response is calculated by the method and information inputted into the method indicates that this is an initial assessment, the individual is currently experiencing psychotic symptoms, the individual has no history of a psychotic disorder, and the individual has no history of resistant to anti-psychotic drug treatment. In other aspects of this embodiment, an outcome assessment indicates that an individual is not suffering a first episode of the psychotic disorder when a normal latent inhibition response is calculated by the method and information inputted into the method indicates that this is an initial assessment, the individual is currently experiencing psychotic symptoms, the individual has no history of a psychotic disorder, and the individual has no history of resistant to anti-psychotic drug treatment. In yet other aspects of this embodiment, an outcome assessment indicates that an individual is suffering a first episode of the psychotic disorder when an enhanced latent inhibition response is calculated by the method and information inputted into the method indicates that this is an initial assessment, the individual is currently experiencing psychotic symptoms, the individual has no history of a psychotic disorder, and the individual has no history of resistant to anti-psychotic drug treatment.

In other aspects of this embodiment, when working memory is also measured, an outcome assessment indicates that an individual is suffering a first episode of the psychotic disorder when an attenuated latent inhibition response is calculated by the method, information inputted into the method indicates that this is an initial assessment, the individual is currently experiencing psychotic symptoms, the individual has no history of a psychotic disorder, and the individual has no history of resistant to anti-psychotic drug treatment, and there is a deficit in working memory. In other aspects of this embodiment, when working memory is also measured, an outcome assessment indicates that an individual is suffering a first episode of the psychotic disorder when an attenuated latent inhibition response is calculated by the method, information inputted indicates that this is an initial assessment, the individual is currently experiencing psychotic symptoms, the individual has no history of a psychotic disorder, and the individual has no history of resistant to anti-psychotic drug treatment, and there is not a deficit in working memory. In yet other aspects of this embodiment, when working memory is also measured, an outcome assessment indicates that an individual is not suffering a first episode of the psychotic disorder when a normal latent inhibition response is calculated by the method, information inputted into the method indicates that this is an initial assessment, the individual is currently experiencing psychotic symptoms, the individual has no history of a psychotic disorder, and the individual has no history of resistant to anti-psychotic drug treatment, and there is a deficit in working memory. In yet other aspects of this embodiment, when working memory is also measured, an outcome assessment indicates that an individual is not suffering a first episode of the psychotic disorder when a normal latent inhibition response is calculated by the method, information inputted into the method indicates that this is an initial assessment, the individual is currently experiencing psychotic symptoms, the individual has no history of a psychotic disorder, and the individual has no history of resistant to anti-psychotic drug treatment, and there is not a deficit in working memory. In still other aspects of this embodiment, when working memory is also measured, an outcome assessment indicates that an individual is suffering a first episode of the psychotic disorder when an enhanced latent inhibition response is calculated by the method, information inputted into the method indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder. In still other aspects of this embodiment, when working memory is also measured, an outcome assessment indicates that an individual is suffering a first episode of the psychotic disorder when an enhanced latent inhibition response is calculated by the method, information inputted into the method indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted to be suffering a first episode of the psychotic disorder.

In one embodiment, an outcome assessment of psychotic disorder determination method disclosed herein pertains to whether an individual is suffering from the psychotic disorder. In aspects of this embodiment, an outcome assessment indicates that an individual is suffering from a psychotic disorder when an attenuated latent inhibition response is calculated by the method and information inputted into the method indicates that the individual has a history of a psychotic disorder, and the individual has no history of resistant to anti-psychotic drug treatment. In other aspects of this embodiment, an outcome assessment indicates that an individual is not suffering from a psychotic disorder when a normal latent inhibition response is calculated by the method and information inputted into the method indicates that the individual has a history of a psychotic disorder, and the individual has no history of resistant to anti-psychotic drug treatment. In yet other aspects of this embodiment, an outcome assessment indicates that an individual is suffering from a psychotic disorder when an enhanced latent inhibition response is calculated by the method and information inputted into the method indicates that the individual has a history of a psychotic disorder, and the individual has no history of resistant to anti-psychotic drug treatment.

In other aspects of this embodiment, when working memory is also measured, an outcome assessment indicates that an individual is suffering from a psychotic disorder when an attenuated latent inhibition response is calculated by the method, information inputted into the method indicates that the individual has a history of a psychotic disorder, and the individual has no history of resistant to anti-psychotic drug treatment, and there is a deficit in working memory. In other aspects of this embodiment, when working memory is also measured, an outcome assessment indicates that an individual is suffering from a psychotic disorder when an attenuated latent inhibition response is calculated by the method, information inputted into the method indicates that the individual has a history of a psychotic disorder, and the individual has no history of resistant to anti-psychotic drug treatment, and there is not a deficit in working memory. In yet other aspects of this embodiment, when working memory is also measured, an outcome assessment indicates that an individual is not suffering from a psychotic disorder when a normal latent inhibition response is calculated by the method, information inputted into the method indicates that the individual has a history of a psychotic disorder, and the individual has no history of resistant to anti-psychotic drug treatment, and there is a deficit in working memory. In yet other aspects of this embodiment, when working memory is also measured, an outcome assessment indicates that an individual is not suffering from a psychotic disorder when a normal latent inhibition response is calculated by the method, information inputted into the method indicates that the individual has a history of a psychotic disorder, and the individual has no history of resistant to anti-psychotic drug treatment, and there is not a deficit in working memory. In still other aspects of this embodiment, when working memory is also measured, an outcome assessment indicates that an individual is suffering from a psychotic disorder when an enhanced latent inhibition response is calculated by the method, information inputted into the method indicates that the individual has a history of a psychotic disorder, and the individual has no history of resistant to anti-psychotic drug treatment, and there is a deficit in working memory. In still other aspects of this embodiment, when working memory is also measured, an outcome assessment indicates that an individual is suffering from a psychotic disorder when an enhanced latent inhibition response is calculated by the method, information inputted into the method indicates that the individual has a history of a psychotic disorder, and the individual has no history of resistant to anti-psychotic drug treatment, and there is not a deficit in working memory.

In one embodiment, an outcome assessment of psychotic disorder determination method disclosed herein pertains to whether an individual is suffering from a treatment-resistant form of a psychotic disorder. In aspects of this embodiment, an outcome assessment indicates that an individual is not suffering from a treatment-resistant form of the psychotic disorder when an attenuated latent inhibition response is calculated by the method and the information inputted into the method indicates that the individual is currently experiencing psychotic symptoms, the individual has a history of a psychotic disorder, and the individual has a history of resistant to an anti-psychotic drug treatment. In aspects of this embodiment, an outcome assessment indicates that an individual is suffering from a treatment-resistant form of the psychotic disorder when a normal latent inhibition response is calculated by the method and the information inputted into the method indicates that the individual is currently experiencing psychotic symptoms, the individual has a history of a psychotic disorder, and the individual has a history of resistant to an anti-psychotic drug treatment. In aspects of this embodiment, an outcome assessment indicates that an individual is suffering from a treatment-resistant form of the psychotic disorder when an enhanced latent inhibition response is calculated by the method and the information inputted into the method indicates that the individual is currently experiencing psychotic symptoms, the individual has a history of a psychotic disorder, and the individual has a history of resistant to an anti-psychotic drug treatment, the individual is predicted to be suffering from a treatment-resistant form of the psychotic disorder.

In other aspects of this embodiment, when working memory is also measured, an outcome assessment indicates that an individual is suffering from a treatment-resistant form of the psychotic disorder when an attenuated latent inhibition response is calculated by the method, information inputted into the method indicates that the individual is currently experiencing psychotic symptoms, the individual has a history of a psychotic disorder, and the individual has a history of resistant to an anti-psychotic drug treatment, and there is a deficit in working memory. In other aspects of this embodiment, when working memory is also measured, an outcome assessment indicates that an individual is suffering from a treatment-resistant form of the psychotic disorder when an attenuated latent inhibition response is calculated by the method, information inputted into the method indicates that the individual is currently experiencing psychotic symptoms, the individual has a history of a psychotic disorder, and the individual has a history of resistant to an anti-psychotic drug treatment, and there is not a deficit in working memory. In yet other aspects of this embodiment, when working memory is also measured, an outcome assessment indicates that an individual is suffering from a treatment-resistant form of the psychotic disorder when a normal latent inhibition response is calculated by the method, information inputted into the method indicates that the individual is currently experiencing psychotic symptoms, the individual has a history of a psychotic disorder, and the individual has a history of resistant to an anti-psychotic drug treatment, and there is a deficit in working memory. In yet other aspects of this embodiment, when working memory is also measured, an outcome assessment indicates that an individual is suffering from a treatment-resistant form of the psychotic disorder when a normal latent inhibition response is calculated by the method, information inputted into the method indicates that the individual is currently experiencing psychotic symptoms, the individual has a history of a psychotic disorder, and the individual has a history of resistant to an anti-psychotic drug treatment, and there is not a deficit in working memory. In still other aspects of this embodiment, when working memory is also measured, an outcome assessment indicates that an individual is suffering from a treatment-resistant form of the psychotic disorder when an enhanced latent inhibition response is calculated by the method, information inputted into the method indicates that the individual is currently experiencing psychotic symptoms, the individual has a history of a psychotic disorder, and the individual has a history of resistant to an anti-psychotic drug treatment, and there is a deficit in working memory. In still other aspects of this embodiment, when working memory is also measured, an outcome assessment indicates that an individual is suffering from a treatment-resistant form of the psychotic disorder when an enhanced latent inhibition response is calculated by the method, information inputted into the method indicates that the individual is currently experiencing psychotic symptoms, the individual has a history of a psychotic disorder, and the individual has a history of resistant to an anti-psychotic drug treatment, and there is not a deficit in working memory.

With respect to a therapy recommendation method disclosed herein an outcome assessment comprise a recommend therapy to treat an individual (FIG. 7). In aspects of this embodiment, a recommended therapy includes i) no therapy recommendation; or ii) treating with a pro-cognitive drug, treating with an anti-psychotic drug, treating with clozapine or an alternative drug for treatment-resistant psychotic symptoms, or any combination thereof.

In aspects of this embodiment, an outcome assessment indicates that an individual is currently at an ultra-high risk for the psychotic disorder and a therapy recommendation includes treating with a pro-cognitive drug when an attenuated latent inhibition response is calculated by the method and information inputted into the method indicates that this is an initial assessment, the individual is not currently experiencing psychotic symptoms, the individual has no history of a psychotic disorder, and the individual has no history of resistant to anti-psychotic drug treatment. In other aspects of this embodiment, an outcome assessment indicates that an individual is not currently at an ultra-high risk for the psychotic disorder and no therapy recommendation is provided when a normal latent inhibition response is calculated by the method and information inputted into the method indicates that this is an initial assessment, the individual is not currently experiencing psychotic symptoms, the individual has no history of a psychotic disorder, and the individual has no history of resistant to anti-psychotic drug treatment. In yet other aspects of this embodiment, an outcome assessment indicates that an individual is currently at an ultra-high risk for the psychotic disorder and a therapy recommendation includes treating with a pro-cognitive drug when an enhanced latent inhibition response is calculated by the method and information inputted into the method indicates that this is an initial assessment, the individual is not currently experiencing psychotic symptoms, the individual has no history of a psychotic disorder, and the individual has no history of resistant to anti-psychotic drug treatment.

In aspects of this embodiment, when working memory is also measured, an outcome assessment indicates that an individual is currently at an ultra-high risk for the psychotic disorder and a therapy recommendation includes treating with a pro-cognitive drug when an attenuated latent inhibition response is calculated by the method. information inputted into the method indicates that this is an initial assessment, the individual is not currently experiencing psychotic symptoms, the individual has no history of a psychotic disorder, and the individual has no history of resistant to anti-psychotic drug treatment, and there is a deficit in working memory. In aspects of this embodiment, when working memory is also measured, an outcome assessment indicates that an individual is not currently at an ultra-high risk for the psychotic disorder and no therapy recommendation is provided when an attenuated latent inhibition response is calculated by the method, information inputted into the method indicates that this is an initial assessment, the individual is not currently experiencing psychotic symptoms, the individual has no history of a psychotic disorder, and the individual has no history of resistant to anti-psychotic drug treatment, and there is not a deficit in working memory. In other aspects of this embodiment, when working memory is also measured, an outcome assessment indicates that an individual is currently at an ultra-high risk for the psychotic disorder and a therapy recommendation includes treating with a pro-cognitive drug when a normal latent inhibition response is calculated by the method. information inputted into the method indicates that this is an initial assessment, the individual is not currently experiencing psychotic symptoms, the individual has no history of a psychotic disorder, and the individual has no history of resistant to anti-psychotic drug treatment, and there is a deficit in working memory. In other aspects of this embodiment, when working memory is also measured, an outcome assessment indicates that an individual is not currently at an ultra-high risk for the psychotic disorder and no therapy recommendation is provided when a normal latent inhibition response is calculated by the method. information inputted into the method indicates that this is an initial assessment, the individual is not currently experiencing psychotic symptoms, the individual has no history of a psychotic disorder, and the individual has no history of resistant to anti-psychotic drug treatment, and there is not a deficit in working memory. In yet other aspects of this embodiment, when working memory is also measured, an outcome assessment indicates that an individual is currently at an ultra-high risk for the psychotic disorder and a therapy recommendation includes treating with a pro-cognitive drug when an enhanced latent inhibition response is calculated by the method. information inputted into the method indicates that this is an initial assessment, the individual is not currently experiencing psychotic symptoms, the individual has no history of a psychotic disorder, and the individual has no history of resistant to anti-psychotic drug treatment, and there is a deficit in working memory. In yet other aspects of this embodiment, when working memory is also measured, an outcome assessment indicates that an individual is not currently at an ultra-high risk for the psychotic disorder and no therapy recommendation is provided when an enhanced latent inhibition response is calculated by the method. information inputted into the method indicates that this is an initial assessment, the individual is not currently experiencing psychotic symptoms, the individual has no history of a psychotic disorder, and the individual has no history of resistant to anti-psychotic drug treatment, and there is not a deficit in working memory.

In aspects of this embodiment, an outcome assessment indicates that an individual is suffering a first episode of the psychotic disorder and a therapy recommendation includes treating with an anti-psychotic drug when an attenuated latent inhibition response is calculated by the method and information inputted into the method indicates that this is an initial assessment, the individual is currently experiencing psychotic symptoms, the individual has no history of a psychotic disorder, and the individual has no history of resistant to anti-psychotic drug treatment. In other aspects of this embodiment, an outcome assessment indicates that an individual is not suffering a first episode of the psychotic disorder and a therapy recommendation includes maintaining a current treatment when a normal latent inhibition response is calculated by the method and information inputted into the method indicates that this is an initial assessment, the individual is currently experiencing psychotic symptoms, the individual has no history of a psychotic disorder, and the individual has no history of resistant to anti-psychotic drug treatment. In yet other aspects of this embodiment, an outcome assessment indicates that an individual is suffering a first episode of the psychotic disorder and a therapy recommendation includes treating with a pro-cognitive drug when an enhanced latent inhibition response is calculated by the method and information inputted into the method indicates that this is an initial assessment, the individual is currently experiencing psychotic symptoms, the individual has no history of a psychotic disorder, and the individual has no history of resistant to anti-psychotic drug treatment.

In other aspects of this embodiment, when working memory is also measured, an outcome assessment indicates that an individual is suffering a first episode of the psychotic disorder and a therapy recommendation includes treating with an anti-psychotic drug and a pro-cognitive drug when an attenuated latent inhibition response is calculated by the method. information inputted into the method indicates that this is an initial assessment, the individual is currently experiencing psychotic symptoms, the individual has no history of a psychotic disorder, and the individual has no history of resistant to anti-psychotic drug treatment, and there is a deficit in working memory. In other aspects of this embodiment, when working memory is also measured, an outcome assessment indicates that an individual is suffering a first episode of the psychotic disorder and a therapy recommendation includes treating with an anti-psychotic drug when an attenuated latent inhibition response is calculated by the method. information inputted into the method indicates that this is an initial assessment, the individual is currently experiencing psychotic symptoms, the individual has no history of a psychotic disorder, and the individual has no history of resistant to anti-psychotic drug treatment, and there is not a deficit in working memory. In other aspects of this embodiment, when working memory is also measured, an outcome assessment indicates that an individual is not suffering a first episode of the psychotic disorder and a therapy recommendation includes treating with an anti-psychotic drug and a pro-cognitive drug when a normal latent inhibition response is calculated by the method. information inputted into the method indicates that this is an initial assessment, the individual is currently experiencing psychotic symptoms, the individual has no history of a psychotic disorder, and the individual has no history of resistant to anti-psychotic drug treatment, and there is a deficit in working memory. In other aspects of this embodiment, when working memory is also measured, an outcome assessment indicates that an individual is not suffering a first episode of the psychotic disorder and a therapy recommendation includes maintaining a current treatment when a normal latent inhibition response is calculated by the method. information inputted into the method indicates that this is an initial assessment, the individual is currently experiencing psychotic symptoms, the individual has no history of a psychotic disorder, and the individual has no history of resistant to anti-psychotic drug treatment, and there is not a deficit in working memory. In other aspects of this embodiment, when working memory is also measured, an outcome assessment indicates that an individual is suffering a first episode of the psychotic disorder and a therapy recommendation includes treating with a pro-cognitive drug when an enhanced latent inhibition response is calculated by the method. information inputted into the method indicates that this is an initial assessment, the individual is currently experiencing psychotic symptoms, the individual has no history of a psychotic disorder, and the individual has no history of resistant to anti-psychotic drug treatment, and there is a deficit in working memory. In other aspects of this embodiment, when working memory is also measured, an outcome assessment indicates that an individual is suffering a first episode of the psychotic disorder and a therapy recommendation includes treating with a pro-cognitive drug when an enhanced latent inhibition response is calculated by the method. information inputted into the method indicates that this is an initial assessment, the individual is currently experiencing psychotic symptoms, the individual has no history of a psychotic disorder, and the individual has no history of resistant to anti-psychotic drug treatment, and there is not a deficit in working memory.

In aspects of this embodiment, an outcome assessment indicates that an individual is suffering from the psychotic disorder and a therapy recommendation includes treating with an anti-psychotic drug and a pro-cognitive drug when an attenuated latent inhibition response is calculated by the method and information inputted into the method indicates that the individual has a history of a psychotic disorder, and the individual has no history of resistant to anti-psychotic drug treatment. In other aspects of this embodiment, an outcome assessment indicates that an individual is not suffering from the psychotic disorder and a therapy recommendation includes maintaining a current treatment when a normal latent inhibition response is calculated by the method and information inputted into the method indicates that the individual has a history of a psychotic disorder, and the individual has no history of resistant to anti-psychotic drug treatment. In yet other aspects of this embodiment, an outcome assessment indicates that an individual is suffering from the psychotic disorder and a therapy recommendation includes treating with a pro-cognitive drug when an enhanced latent inhibition response is calculated by the method and information inputted into the method indicates that the individual has a history of a psychotic disorder, and the individual has no history of resistant to anti-psychotic drug treatment.

In other aspects of this embodiment, when working memory is also measured, an outcome assessment indicates that an individual is suffering from the psychotic disorder and a therapy recommendation includes treating with an anti-psychotic drug and a pro-cognitive drug when an attenuated latent inhibition response is calculated by the method. information inputted into the method indicates that the individual has a history of a psychotic disorder, and the individual has no history of resistant to anti-psychotic drug treatment, and there is a deficit in working memory. In other aspects of this embodiment, when working memory is also measured, an outcome assessment indicates that an individual is suffering from the psychotic disorder and a therapy recommendation includes treating with an anti-psychotic drug when an attenuated latent inhibition response is calculated by the method. information inputted into the method indicates that the individual has a history of a psychotic disorder, and the individual has no history of resistant to anti-psychotic drug treatment, and there is not a deficit in working memory. In yet other aspects of this embodiment, when working memory is also measured, an outcome assessment indicates that an individual is not suffering from the psychotic disorder and a therapy recommendation includes treating with a pro-cognitive drug in addition to maintaining a current treatment when a normal latent inhibition response is calculated by the method. information inputted into the method indicates that the individual has a history of a psychotic disorder, and the individual has no history of resistant to anti-psychotic drug treatment, and there is a deficit in working memory. In yet other aspects of this embodiment, when working memory is also measured, an outcome assessment indicates that an individual is not suffering from the psychotic disorder and a therapy recommendation includes maintaining a current treatment when a normal latent inhibition response is calculated by the method. information inputted into the method indicates that the individual has a history of a psychotic disorder, and the individual has no history of resistant to anti-psychotic drug treatment, and there is not a deficit in working memory. In still other aspects of this embodiment, when working memory is also measured, an outcome assessment indicates that an individual is suffering from the psychotic disorder and a therapy recommendation includes treating with an anti-psychotic drug and a pro-cognitive drug when an enhanced latent inhibition response is calculated by the method. information inputted into the method indicates that the individual has a history of a psychotic disorder, and the individual has no history of resistant to anti-psychotic drug treatment, and there is a deficit in working memory. In still other aspects of this embodiment, when working memory is also measured, an outcome assessment indicates that an individual is suffering from the psychotic disorder and a therapy recommendation includes treating with an anti-psychotic drug and a pro-cognitive drug when an enhanced latent inhibition response is calculated by the method, information inputted into the method indicates that the individual has a history of a psychotic disorder, and the individual has no history of resistant to anti-psychotic drug treatment, and there is not a deficit in working memory.

In aspects of this embodiment, an outcome assessment indicates that an individual is suffering from a treatment-resistant form of a psychotic disorder and a therapy recommendation includes treating with an anti-psychotic drug and a pro-cognitive drug when an attenuated latent inhibition response is calculated by the method and information inputted into the method indicates that the individual is currently experiencing psychotic symptoms, the individual has a history of a psychotic disorder, and the individual has a history of resistant to an anti-psychotic drug treatment. In other aspects of this embodiment, an outcome assessment indicates that an individual is suffering from a treatment-resistant form of a psychotic disorder and a therapy recommendation includes treating with clozapine or an alternative drug for treatment-resistant psychotic symptoms and a pro-cognitive drug when a normal latent inhibition response is calculated by the method and information inputted into the method indicates that the individual is currently experiencing psychotic symptoms, the individual has a history of a psychotic disorder, and the individual has a history of resistant to an anti-psychotic drug treatment. In yet other aspects of this embodiment, an outcome assessment indicates that an individual is suffering from a treatment-resistant form of a psychotic disorder and a therapy recommendation includes treating with clozapine or an alternative drug for treatment-resistant psychotic symptoms and a pro-cognitive drug when an enhanced latent inhibition response is calculated by the method and information inputted into the method indicates that the individual is currently experiencing psychotic symptoms, the individual has a history of a psychotic disorder, and the individual has a history of resistant to an anti-psychotic drug treatment.

In aspects of this embodiment, when working memory is also measured, an outcome assessment indicates that an individual is suffering from a treatment-resistant form of a psychotic disorder and a therapy recommendation includes treating with an anti-psychotic drug and a pro-cognitive drug when an attenuated latent inhibition response is calculated by the method. information inputted into the method indicates that the individual is currently experiencing psychotic symptoms, the individual has a history of a psychotic disorder, and the individual has a history of resistant to an anti-psychotic drug treatment, and there is a deficit in working memory. In aspects of this embodiment, when working memory is also measured, an outcome assessment indicates that an individual is suffering from a treatment-resistant form of a psychotic disorder and a therapy recommendation includes treating with an anti-psychotic drug and a pro-cognitive drug when an attenuated latent inhibition response is calculated by the method. information inputted into the method indicates that the individual is currently experiencing psychotic symptoms, the individual has a history of a psychotic disorder, and the individual has a history of resistant to an anti-psychotic drug treatment, and there is not a deficit in working memory. In aspects of this embodiment, when working memory is also measured, an outcome assessment indicates that an individual is suffering from a treatment-resistant form of a psychotic disorder and a therapy recommendation includes treating with clozapine or an alternative drug for treatment-resistant psychotic symptoms and a pro-cognitive drug when a normal latent inhibition response is calculated by the method. information inputted into the method indicates that the individual is currently experiencing psychotic symptoms, the individual has a history of a psychotic disorder, and the individual has a history of resistant to an anti-psychotic drug treatment, and there is a deficit in working memory. In aspects of this embodiment, when working memory is also measured, an outcome assessment indicates that an individual is suffering from a treatment-resistant form of a psychotic disorder and a therapy recommendation includes treating with clozapine or an alternative drug for treatment-resistant psychotic symptoms and a pro-cognitive drug when a normal latent inhibition response is calculated by the method. information inputted into the method indicates that the individual is currently experiencing psychotic symptoms, the individual has a history of a psychotic disorder, and the individual has a history of resistant to an anti-psychotic drug treatment, and there is not a deficit in working memory. In aspects of this embodiment, when working memory is also measured, an outcome assessment indicates that an individual is suffering from a treatment-resistant form of a psychotic disorder and a therapy recommendation includes treating with clozapine or an alternative drug for treatment-resistant psychotic symptoms and a pro-cognitive drug when an enhanced latent inhibition response is calculated by the method. information inputted into the method indicates that the individual is currently experiencing psychotic symptoms, the individual has a history of a psychotic disorder, and the individual has a history of resistant to an anti-psychotic drug treatment, and there is a deficit in working memory. In aspects of this embodiment, when working memory is also measured, an outcome assessment indicates that an individual is suffering from a treatment-resistant form of a psychotic disorder and a therapy recommendation includes treating with clozapine or an alternative drug for treatment-resistant psychotic symptoms and a pro-cognitive drug when an enhanced latent inhibition response is calculated by the method. information inputted into the method indicates that the individual is currently experiencing psychotic symptoms, the individual has a history of a psychotic disorder, and the individual has a history of resistant to an anti-psychotic drug treatment, and there is not a deficit in working memory.

In aspects of this embodiment, an outcome assessment indicates that the calculated latent inhibition score was an improvement over the one or more previous latent inhibition scores and therapy recommendation includes increasing the drug dose of a current treatment when an attenuated latent inhibition response is calculated by the method and information inputted into the method indicates that this was a subsequent assessment. In other aspects of this embodiment, an outcome assessment indicates that the calculated latent inhibition score was an improvement over the one or more previous latent inhibition score and a therapy recommendation includes maintaining a current treatment when a normal latent inhibition response is calculated by the method and information inputted into the method indicates that this was a subsequent assessment. In yet other aspects of this embodiment, an outcome assessment indicates that the calculated latent inhibition score was similar or worse than the one or more previous latent inhibition score and a therapy recommendation includes decreasing the drug dose of a current treatment when an enhanced latent inhibition response calculated by the method and information inputted into the method indicates that this was a subsequent assessment.

In aspects of this embodiment, an outcome assessment indicates that the calculated latent inhibition score was similar or worse than the one or more previous latent inhibition scores and a therapy recommendation includes a different treatment when an attenuated latent inhibition response is calculated by the method and information inputted into the method indicates that this was a subsequent assessment. In other aspects of this embodiment, an outcome assessment indicates that the calculated latent inhibition score was similar to the one or more previous latent inhibition scores and a therapy recommendation includes maintaining a current treatment when a normal latent inhibition response is calculated by the method and information inputted into the method indicates that this was a subsequent assessment. In yet other aspects of this embodiment, an outcome assessment indicates that the calculated latent inhibition score was similar or worse than the one or more previous latent inhibition scores and a therapy recommendation includes a different treatment when an enhanced latent inhibition response is calculated by the method and information inputted into the method indicates that this was a subsequent assessment, when the calculated latent inhibition score.

Aspects of the present specification disclose a pro-cognitive drug. In one embodiment, a pro-cognitive drug disclosed herein includes an agonist, an antagonist, a partial agonist, a positive allosteric modulator, a negative allosteric modulator, a silent allosteric modulator, or an inverse agonist of an ionotropic receptor. Exemplary examples of an ionotropic receptor include, without limitation, a Nicotinic Acetylcholine (nAch) receptor, an ionotropic Gamma-Aminobutyric Acid (GABA) receptor, an ionotropic Glutamine (Glu) receptor, or an ionotropic Serotonin (5-HT) receptor. Non-limiting examples of an nAch receptor include an $\alpha 4\beta 2$ nAch receptor, an $\alpha 3\beta 4$ nAch receptor, and an $\alpha 7$ nAch receptor. Non-limiting examples of an ionotropic GABA receptor include a $GABA_A$ receptor and a $GABA_{A-\rho}$ receptor. Non-limiting examples of an ionotropic Glutamine receptor includes an N-methyl-D-aspartate receptor, a Kainate receptor, and an $\alpha$-amino-3-hydroxy-5-methyl-4-isoxazolepropionic acid receptor. Non-limiting examples of an onotropphic 5-HT receptor include a $5-HT_3$ receptor.

In one embodiment, a pro-cognitive drug disclosed herein includes an agonist, an antagonist, a partial agonist, a positive allosteric modulator, a negative allosteric modulator, a silent allosteric modulator, or an inverse agonist of a metabotropic receptor. Exemplary examples of a metabotropic receptor include, without limitation, a Muscarinic Acetylcholine (mAch) receptor, a Cannabinoid (CB) receptor, a Dopamine (DA) receptor, an Endorphin receptor, a metabotropic Gamma-Aminobutyric Acid (GABA) receptor, a metabotropic Glutamine (Glu) receptor, a Norepinephrine (NE) receptor, an Oxytocin receptor, and a metabotropic Serotonin (5-HT) receptor. Non-limiting examples of a mAch receptor include a $M_1$ mAch receptor, $M_2$ mAch receptor, $M_3$ mAch receptor, $M_4$ mAch receptor, and $M_5$ mAch receptor. Non-limiting examples of a CB receptor include a CB1 receptor and CB2 receptor. Non-limiting examples of a DA receptor include a $DA_1$ receptor, a $DA_2$ receptor, a $DA_3$ receptor, a $DA_4$ receptor, or a $DA_5$ receptor and heterodimers thereof. Non-limiting examples of an Endorphin receptor is a $\mu_1$ Opioid receptor, a $\mu_2$ Opioid receptor, and a $\mu_3$ Opioid receptor. Non-limiting examples of a metabotropic GABA receptor include a $GABA_B$ receptor. Non-limiting examples of a metabotropic Glu receptor include a Glu $receptor_1$, a Glu $receptor_2$, a Glu $receptor_3$, a Glu $receptor_4$, a Glu $receptor_5$, a Glu $receptor_6$, a Glu $receptor_7$, and a Glu $receptor_8$. Non-limiting examples of a NE receptor include an $\alpha_1$ Adrenergic receptor, an $\alpha_2$ Adrenergic receptor, a $\beta_1$ Adrenergic receptor, a $\beta_2$ Adrenergic receptor, and a $\beta_3$ Adrenergic receptor. Non-limiting examples of a metabotropic 5-HT receptor include a $5-HT_1$ receptor, a $5-HT_2$ receptor, a $5-HT_4$ receptor, a $5-HT_5$ receptor, a $5-HT_6$ receptor, and a $5-HT_7$ receptor.

In one embodiment, a pro-cognitive drug disclosed herein includes an agonist, an antagonist, a partial agonist, a positive allosteric modulator, a negative allosteric modulator, a silent allosteric modulator, or an inverse agonist of a phosphodiesterase (PDE). Exemplary examples of a PDE include, without limitation, a $PDE_1$, a $PDE_2$, a $PDE_3$, a $PDE_4$, a $PDE_5$, a $PDE_6$, a $PDE_7$, a $PDE_8$, a $PDE_9$, and a $PDE_{10}$.

Aspects of the present specification disclose an anti-psychotic drug. In one embodiment, an anti-psychotic drug includes a dopamine antagonist. Exemplary examples of a dopamine antagonist include, without limitation, Chlorpromazine, Haloperidol, Loxapine, Perphenazine, Prochlorperazine, Thiothixene, Thioridazine, and Trifluoperazine.

In one embodiment, an anti-psychotic drug includes a serotonin-dopamine antagonist. Exemplary examples of a serotonin-dopamine antagonist include, without limitation, Olanzapine, Paliperidone, Quetiapine, and Risperidone.

In one embodiment, an anti-psychotic drug includes a partial dopamine agonist. Exemplary examples of a partial dopamine agonist include, without limitation, Aripiprazole.

A group assignment method, a psychotic disorder determination method, and a therapy recommendation method disclosed herein can be useful to assign an individual suffering from a wide variety of psychotic disorders. Exemplary psychotic disorders include, without limitation, a schizophrenia spectrum disorder, an obsessive-compulsive disorder, an anxiety disorder, a bipolar disorder, or a dementia disease.

In other embodiments, a group assignment method can be described as follows:

1. A method of assigning an individual to a group for a clinical study on a psychotic disorder using a non-invasive computational device-based test, the method comprising:
    a. having the individual perform a latent inhibition assessment using the computational device and a graphical user interface coupled thereto, the latent inhibition assessment comprising a pre-exposure phase and a test phase,
        i. wherein the pre-exposure phase includes,
            presenting the individual with a first set of directions for how to respond to each stimulus of a first group of stimuli, wherein the first set of directions include pre-exposure phase instructions which require the individual to respond to each stimulus of the first group of stimuli in a defined manner;
            presenting the individual with a random order of the first group of stimuli, each stimulus being presented for 10 msec to 10,000 msec, wherein the first group of stimuli comprises a plurality of stimuli including at least one preexposed stimulus and one or more neutral stimuli;
        ii. wherein the test phase includes,
            presenting the individual with a second set of directions for how to respond to each stimulus of a second group of stimuli, wherein the second set of directions include test phase instructions which require the individual to anticipate the occurrence of a target stimulus;
            presenting the individual with the second group of stimuli, each stimulus being presented for 10 msec to 10,000 msec with a 0 msec to 10,000 msec interval between each stimulus, wherein the second group of stimuli comprises a plurality of stimuli including the at least one preexposed stimuli, a non-preexposed stimulus, the target stimulus, and the one or more neutral stimuli; recording and analyzing the individual's interaction with the graphical user interface following presentation of the second group of stimuli, by
            measuring a time associated with a target anticipated response of the individual to each stimulus from the plurality of stimuli, wherein a response to the target stimulus of less than the sum of the presentation time and interval time according to the second set of directions is indicative that the individual anticipated the occurrence of the target stimulus, and wherein a response to the target stimulus of equal to or more than the sum of the presentation time and interval time according to the second set of directions is indicative that the individual failed to anticipate the occurrence of the target stimulus;
    b. measuring a latent inhibition response of the individual to calculate a latent inhibition score, by modeling the time associated with a target anticipated response in one or more statistical analyses that analyze one or more of a count of a number of presentations on which the response to the targeted stimulus occurred, a central tendency of the number of responses to the target stimulus, or a distance from a central tendency of the number of the responses to the target stimulus, and determining whether the individual exhibited an attenuated latent inhibition response, a normal latent inhibition response or an enhanced latent inhibition response from the latent inhibition score; and
    c. assigning the individual to a group designated for the clinical study.
2. The method of embodiment 1, wherein the pre-exposure phase instructions require the individual to respond to a stimulus of the first group of stimuli as it appears on the screen.
3. The method of embodiment 1, wherein the pre-exposure phase instructions require the individual to respond to a current stimulus of the first group of stimuli only if the current stimulus is the same as a stimulus shown one position back in a sequence of the first group of stimuli.
4. The method of embodiment 1, wherein the pre-exposure phase instructions require the individual to respond to a current stimulus of the first group of stimuli only if the current stimulus is the same as a stimulus shown two positions back in a sequence of the first group of stimuli.
5. The method of any one of embodiments 1-4, wherein each stimulus is presented for is 100 msec to 5,000 msec, 250 msec to 2,500 msec, 500 msec to 1,500 msec, 750 msec to 1,250 msec, or 1,000 msec
6. The method of any one of embodiments 1-5, wherein step (b)(i) further comprising an interval between each stimulus.
7. The method of embodiment 6, wherein interval between each stimulus is 1 msec to 10,000 msec, 5 msec to 1,000 msec, 10 msec to 500 msec, 15 msec to 250 msec, 20 msec to 100 msec, 25 msec to 75 msec, or 50 msec
8. The method of any one of embodiments 1-7, wherein step (a)(i) further comprises measuring a response of the individual to each stimulus from the first group of stimuli.
9. The method of any one of embodiments 1-8, wherein if the individual responses to at least 50%, at least 55%, at least 60%, at least 65%, at least 70%, at least 75%, at least 80%, at least 85%, at least 90%, or at least 95% of the first group of stimuli according to the first set of directions, the program proceeds to the test phase of step (b)(ii).
10. The method of any one of embodiments 1-9, wherein in step (a)(ii) if the sum of the presentation time and interval time is less than 550 msec, less than 750 msec, less than 950 msec, less than 1,050 msec, less than 1,150 msec, less than 1,350 msec, less than 1,550 msec, less than 1,750 msec, less than 1,950 msec, less than 2,150 msec, less than 2,350 msec, or less than 2,550 msec, then the individual anticipated the occurrence of the target stimulus.
11. The method of any one of embodiments 1-10, wherein in step (a)(ii) if the sum of the presentation time and interval time is 550 msec or more, 750 msec or more, 950 msec or more, 1,050 msec or more, 1,150 msec or more, 1,350 msec or more, 1,550 msec or more, 1,750 msec or more, 1,950 msec or more, 2,150 msec or more, 2,350 msec or more, 2,550 msec or more, then the individual failed to anticipate the occurrence of the target stimulus.
12. The method of any one of embodiments 1-11, wherein in step (b)(ii) an equal number of presentations for the target stimulus occurs after presentation of the preexposed stimulus and after presentation of the non-preexposed stimulus
13. The method of any one of embodiments 1-11, wherein in step (b)(ii) an unequal number of presentations for the target stimulus occurs after presentation of the preexposed stimulus relative to after presentation of the non-preexposed stimulus
14. The method of embodiment 13, wherein the unequal number of presentations for the target stimulus occurring after presentation of the preexposed stimulus is ±10%, 20%, 30%, 40%, 50% the number of presentations for the target stimulus occurring after presentation of the non-preexposed stimulus.
15. The method of any one of embodiments 1-14, wherein in step (b) the latent inhibition score is calculated by determining one or more reaction times.
16. The method of embodiment 15, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target anticipated response measured when the target stimulus was presented after presentation of the preexposed stimulus; and calculating the latent inhibition score by subtracting the second average time by the first average time.
17. The method of embodiment 15, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target anticipated response measured when the target stimulus was presented after presentation of the preexposed stimulus; and calculating the latent inhibition score by subtracting the first average time by the second average time.
18. The method of embodiment 15, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target prediction response measured when the target stimulus was presented after presentation of the preexposed stimulus; and calculating the latent inhibition score by determining whether the first average time is slower or faster than the second average time.
19. The method of embodiment 15, wherein the measuring a latent inhibition response of the individual to calculate a latent inhibition score further comprises: pairing each target anticipatory response time based on the non-preexposed stimulus with a target anticipatory response time based on the preexposed stimulus; calculating whether a paired target anticipatory response time based on the non-preexposed stimulus was faster relative to its paired target anticipatory response time based on the preexposed stimulus; calculating the latent inhibition score by determining (i) the total number of paired target anticipatory response times based on the non-preexposed stimulus that were higher relative to their paired target anticipatory response time based on the preexposed stimulus, (ii) the total number of paired target anticipatory response times based on the non-preexposed stimulus that were lower relative to their paired target anticipatory response time based on the preexposed stimulus, or (iii) both (i) and (ii).
20. The method of any one of embodiments 1-14, wherein in step (b) the latent inhibition score is calculated by determining a number of anticipatory responses.
21. The method of embodiment 20, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by subtracting the second average number of anticipatory responses by the first average number of anticipatory responses.
22. The method of embodiment 20, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by subtracting the first average number of anticipatory responses by the second average number of anticipatory responses.
23. The method of embodiment 20, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by determining whether the first average number of anticipatory responses is lower or higher than the second average number of anticipatory responses.

24. The method of embodiment 20, wherein the measuring a latent inhibition response of the individual to calculate a latent inhibition score further comprises: pairing each target anticipatory response based on the non-preexposed stimulus with a target anticipatory response based on the preexposed stimulus; calculating whether a paired target anticipatory response time based on the non-preexposed stimulus was faster relative to its paired target anticipatory response time based on the preexposed stimulus; calculating the latent inhibition score by determining (i) the total number of paired target anticipatory response times based on the non-preexposed stimulus that were higher relative to their paired target anticipatory response time based on the preexposed stimulus, (ii) the total number of paired target anticipatory response times based on the non-preexposed stimulus that were lower relative to their paired target anticipatory response time based on the preexposed stimulus, or (iii) both (i) and (ii).

25. The method of any one of embodiments 1-14, wherein in step (b) the latent inhibition score is calculated by determining a percentage of anticipatory responses.

26. The method of embodiment 25, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by subtracting the second percent of anticipatory responses by the first percent of anticipatory responses.

27. The method of embodiment 25, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by subtracting the first percent of anticipatory responses by the second percent of anticipatory responses.

28. The method of embodiment 25, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by determining whether the first percent of anticipatory responses is lower or higher than the second percent of anticipatory responses.

29. The method of any one of embodiments 1-14, wherein in step (b) the latent inhibition score is calculated by determining an accuracy-sensitivity d' score.

30. The method of embodiment 29, wherein the first d' score and the second d' score are calculated by: calculating a first d' score of anticipatory responses based on each target anticipated response measured when the target stimulus was presented after presentation of the non-preexposed stimulus; calculating a second d' score of anticipatory responses based on each target anticipated response measured when the target stimulus was presented after presentation of the preexposed stimulus; and calculating the latent inhibition score by subtracting the second d' score of anticipatory responses by the first d' score of anticipatory responses.

31. The method of embodiment 29, wherein the first d' score and the second d' score are calculated by: calculating a hit rate by dividing the totaling the number of correctly identified back targets by the total number of back targets; calculating a false alarm rate, by dividing the number of responses for stimuli erroneously identified as back targets by the total number of back targets; and applying a z-transformation to the hit rate and the false alarm rate and subtracting the resulting transformed false alarm rate from the resulting transformed hit rate to obtain the d' score.

32. The method of any one of embodiments 1-31, wherein in step (b) the measuring a latent inhibition response of the individual to calculate a latent inhibition score further comprises comparing the latent inhibition score to a reference score comprising a standard range of latent inhibition scores.

33. The method of embodiment 32, wherein the reference score is based on values obtained from normal individuals, values obtained from different types of patients, and/or values obtained from the same individual on one or more prior testings.

34. The method of embodiment 32 or 33, wherein the standard range latent inhibition scores is based on 20 or more, 30 or more, 40 or more, 50 or more, 60 or more, 70 or more, 80 or more, 90 or more, or 100 or more healthy individuals.

35. The method of any one of embodiments 32-34, wherein a latent inhibition score is calculated above the reference score, the latent inhibition score is indicative of an enhanced latent inhibition response; a latent inhibition score is calculated within the standard range latent inhibition scores of the reference score, the latent inhibition score is indicative of a normal latent inhibition response; and a latent inhibition score is calculated below the reference score, the latent inhibition score is indicative of an attenuated latent inhibition response.

36. The method of any one of embodiments 1-35, wherein assignment is based on whether the latent inhibition score of the individual is indicative of an attenuated latent inhibition response, a normal latent inhibition response, or an enhanced latent inhibition response 37. The method of any one of embodiments 1-36, further comprising evaluating working memory.

38. The method of embodiment 37, wherein working memory is evaluated in the pre-exposure phase by providing instructions which require the individual to respond to a current stimulus of the first group of stimuli only if the current stimulus is the same as a stimulus shown one position back in a sequence of the first group of stimuli.
39. The method of embodiment 37, wherein working memory is evaluated in the pre-exposure phase by providing instructions which require the individual to respond to a current stimulus of the first group of stimuli only if the current stimulus is the same as a stimulus shown two positions back in a sequence of the first group of stimuli.
40. The method of any one of embodiments 37-39, wherein assignment is based on whether the latent inhibition score of the individual is indicative of an attenuated latent inhibition response, a normal latent inhibition response, or an enhanced latent inhibition response and whether the individual exhibits a deficit in working memory or not.
41. The method of embodiment 37, wherein working memory is calculate by: counting the number of pre-exposure responses presented based on the presentation back stimulus; counting the number of pre-exposure responses selected correctly by the individual based on the presentation back stimulus; and calculating the percent of pre-exposure responses selected correctly by the individual, wherein 50% or more is indicative of a working memory.
42. The method of embodiment 37, wherein working memory is calculate by: counting the number of pre-exposure responses selected incorrectly by the individual based on the presentation back stimulus; and calculating the percent of pre-exposure responses selected incorrectly by the individual, wherein 50% or more is indicative of impaired working memory.
43. The method of embodiment 37, wherein working memory is calculate by: calculating the average reaction time of pre-exposure responses selected incorrectly by the individual.
44. The method of embodiment 37, wherein working memory is calculate by: calculating a d' score of pre-exposure responses presented based on the presentation of back stimulus.
45. The method of any one of embodiments 1-44, wherein the psychotic disorder includes a schizophrenia spectrum disorder, an obsessive-compulsive disorder, an anxiety disorder, a bipolar disorder, or a dementia disease.

In other embodiments, a psychotic disorder determination method can be described as follows:
1. A method of determining a psychotic disorder of an individual using a non-invasive computational device-based test, the method comprising:
   a. optionally entering information about the individual into a latent inhibition test program running on a computational device, the information including:
      i. whether this is an initial assessment or a subsequent assessment;
      ii. whether or not the individual is currently experiencing psychotic symptoms;
      iii. whether or not the individual has a history of a psychotic disorder; and/or
      iv. whether or not the individual has a history of resistance to anti-psychotic drug treatment
   b. having the individual perform a latent inhibition assessment using the latent inhibition test program running on the computational device and a graphical user interface coupled thereto with which the user interacts, the latent inhibition assessment comprising a pre-exposure phase and a test phase,
      i. wherein the pre-exposure phase includes,
         presenting the individual with a first set of directions for how to respond to each stimulus of a first group of stimuli, wherein the first set of directions include pre-exposure phase instructions which require the individual to respond to each stimulus of the first group of stimuli in a defined manner;
         presenting the individual with a random order of the first group of stimuli, each stimulus being presented for 10 msec to 10,000 msec, wherein the first group of stimuli comprises a plurality of stimuli including at least one preexposed stimulus and one or more neutral stimuli;
      ii. wherein the test phase includes,
         presenting the individual with a second set of directions for how to respond to each stimulus of a second group of stimuli, wherein the second set of directions include test phase instructions which require the individual to anticipate the occurrence of a target stimulus;
         presenting the individual with the second group of stimuli, each stimulus being presented for 10 msec to 10,000 msec with a 0 msec to 10,000 msec interval between each stimulus, wherein the second group of stimuli comprises a plurality of stimuli including the at least one preexposed stimuli, a non-preexposed stimulus, the target stimulus, and the one or more neutral stimuli; recording and analyzing the individual's interaction with the graphical user interface following presentation of the second group of stimuli, by
         measuring a time associated with a target anticipated response of the individual to each stimulus from the plurality of stimuli, wherein a response to the target stimulus of less than the sum of the presentation time and interval time according to the second set of directions is indicative that the individual anticipated the occurrence of the target stimulus, and wherein a response to the target stimulus of equal to or more than the sum of the presentation time and interval time according to the second set of directions is indicative that the individual failed to anticipate the occurrence of the target stimulus;
   c. measuring a latent inhibition response of the individual to calculate a latent inhibition score by modeling the time associated with a target anticipated response in one or more statistical analyses that analyze one or more of a count of a number of presentations on which the response to the targeted stimulus occurred, a central tendency of the number of responses to the target stimulus, or a distance from a central tendency of the number of the responses to the target stimulus, and, determining whether the individual exhibited an attenuated latent inhibition response, a normal latent inhibition response or an enhanced latent inhibition response from the latent inhibition score; and
   d. calculating the psychotic disorder of the individual.

2. The method of embodiment 1, wherein the information entered for (a)(iv) includes whether or not the individual is resistant to an anti-psychotic drug.
3. The method of embodiment 1 or 2, wherein the pre-exposure phase instructions require the individual to respond to a stimulus of the first group of stimuli as it appears on the screen.
4. The method of embodiment 1 or 2, wherein the pre-exposure phase instructions require the individual to respond to a current stimulus of the first group of stimuli only if the current stimulus is the same as a stimulus shown one position back in a sequence of the first group of stimuli.
5. The method of embodiment 1 or 2, wherein the pre-exposure phase instructions require the individual to respond to a current stimulus of the first group of stimuli only if the current stimulus is the same as a stimulus shown two positions back in a sequence of the first group of stimuli.
6. The method of any one of embodiments 1-5, wherein each stimulus is presented for is 100 msec to 5,000 msec, 250 msec to 2,500 msec, 500 msec to 1,500 msec, 750 msec to 1,250 msec, or 1,000 msec
7. The method of any one of embodiments 1-6, wherein step (b)(i) further comprising an interval between each stimulus.
8. The method of embodiment 7, wherein interval between each stimulus is 1 msec to 10,000 msec, 5 msec to 1,000 msec, 10 msec to 500 msec, 15 msec to 250 msec, 20 msec to 100 msec, 25 msec to 75 msec, or 50 msec.
9. The method of any one of embodiments 1-8, wherein step (b)(i) further comprises measuring a response of the individual to each stimulus from the first group of stimuli.
10. The method of any one of embodiments 1-9, wherein if the individual responses to at least 50%, at least 55%, at least 60%, at least 65%, at least 70%, at least 75%, at least 80%, at least 85%, at least 90%, or at least 95% of the first group of stimuli according to the first set of directions, the program proceeds to the test phase of step (b)(ii).
11. The method of any one of embodiments 1-10, wherein in step (b)(ii) if the sum of the presentation time and interval time is less than 550 msec, less than 750 msec, less than 950 msec, less than 1,050 msec, less than 1,150 msec, less than 1,350 msec, less than 1,550 msec, less than 1,750 msec, less than 1,950 msec, less than 2,150 msec, less than 2,350 msec, or less than 2,550 msec, then the individual anticipated the occurrence of the target stimulus.
12. The method of any one of embodiments 1-11, wherein in step (b)(ii) if the sum of the presentation time and interval time is 550 msec or more, 750 msec or more, 950 msec or more, 1,050 msec or more, 1,150 msec or more, 1,350 msec or more, 1,550 msec or more, 1,750 msec or more, 1,950 msec or more, 2,150 msec or more, 2,350 msec or more, 2,550 msec or more, then the individual failed to anticipate the occurrence of the target stimulus.
13. The method of any one of embodiments 1-12, wherein in step (b)(ii) an equal number of presentations for the target stimulus occurs after presentation of the preexposed stimulus and after presentation of the non-preexposed stimulus
14. The method of any one of embodiments 1-12, wherein in step (b)(ii) an unequal number of presentations for the target stimulus occurs after presentation of the preexposed stimulus relative to after presentation of the non-preexposed stimulus
15. The method of embodiment 14, wherein the unequal number of presentations for the target stimulus occurring after presentation of the preexposed stimulus is ±10%, 20%, 30%, 40%, 50% the number of presentations for the target stimulus occurring after presentation of the non-preexposed stimulus.
16. The method of any one of embodiments 1-15, wherein in step (c) the latent inhibition score is calculated by determining one or more reaction times.
17. The method of embodiment 16, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target anticipated response measured when the target stimulus was presented after presentation of the preexposed stimulus; and calculating the latent inhibition score by subtracting the second average time by the first average time.
18. The method of embodiment 16, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target anticipated response measured when the target stimulus was presented after presentation of the preexposed stimulus; and calculating the latent inhibition score by subtracting the first average time by the second average time.
19. The method of embodiment 16, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target prediction response measured when the target stimulus was presented after presentation of the preexposed stimulus; and calculating the latent inhibition score by determining whether the first average time is slower or faster than the second average time.
20. The method of embodiment 16, wherein the measuring a latent inhibition response of the individual to calculate a latent inhibition score further comprises: pairing each target anticipatory response time based on the non-preexposed stimulus with a target anticipatory response time based on the preexposed stimulus; calculating whether a paired target anticipatory response time based on the non-preexposed stimulus was faster relative to its paired target anticipatory response time based on the preexposed stimulus; calculating the latent inhibition score by determining (i) the total number of paired target anticipatory response times based on the non-preexposed stimulus that were higher relative to their paired target anticipatory response time based on the preexposed stimulus, (ii) the total number of paired target anticipatory response times based on the non-preexposed stimulus that were lower relative to their paired target anticipatory response time based on the preexposed stimulus, or (iii) both (i) and (ii).

21. The method of any one of embodiments 1-15, wherein in step (c) the latent inhibition score is calculated by determining a number of anticipatory responses.
22. The method of embodiment 21, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by subtracting the second average number of anticipatory responses by the first average number of anticipatory responses.
23. The method of embodiment 21, wherein measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by subtracting the first average number of anticipatory responses by the second average number of anticipatory responses.
24. The method of embodiment 21, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by determining whether the first average number of anticipatory responses is lower or higher than the second average number of anticipatory responses.
25. The method of embodiment 21, wherein the measuring a latent inhibition response of the individual to calculate a latent inhibition score further comprises: pairing each target anticipatory response based on the non-preexposed stimulus with a target anticipatory response based on the preexposed stimulus; calculating whether a paired target anticipatory response time based on the non-preexposed stimulus was faster relative to its paired target anticipatory response time based on the preexposed stimulus; calculating the latent inhibition score by determining (i) the total number of paired target anticipatory response times based on the non-preexposed stimulus that were higher relative to their paired target anticipatory response time based on the preexposed stimulus, (ii) the total number of paired target anticipatory response times based on the non-preexposed stimulus that were lower relative to their paired target anticipatory response time based on the preexposed stimulus, or (iii) both (i) and (ii).
26. The method of any one of embodiments 1-15, wherein in step (c) the latent inhibition score is calculated by determining a percentage of anticipatory responses.
27. The method of embodiment 26, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by subtracting the second percent of anticipatory responses by the first percent of anticipatory responses.
28. The method of embodiment 26, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by subtracting the first percent of anticipatory responses by the second percent of anticipatory responses.
29. The method of embodiment 26, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by determining whether the first percent of anticipatory responses is lower or higher than the second percent of anticipatory responses.
30. The method of any one of embodiments 1-15, wherein in step (c) the latent inhibition score is calculated by determining an accuracy-sensitivity d' score.
31. The method of embodiment 30, wherein the first d' score and the second d' score are calculated by: calculating a first d' score of anticipatory responses based on each target anticipated response measured when the target stimulus was presented after presentation of the non-preexposed stimulus; calculating a second d' score of anticipatory responses based on each target anticipated response measured when the target stimulus was presented after presentation of the preexposed stimulus; and calculating the latent inhibition score by subtracting the second d' score of anticipatory responses by the first d' score of anticipatory responses.
32. The method of embodiment 30, wherein the first d' score and the second d' score are calculated by: calculating a hit rate by dividing the totaling the number of correctly identified back targets by the total number of back targets; calculating a false alarm rate, by dividing the number of responses for stimuli erroneously identified as back targets by the total number of back targets; and applying a z-transformation to the hit rate and the false alarm rate and subtracting the resulting transformed false alarm rate from the resulting transformed hit rate to obtain the d' score.

33. The method of any one of embodiments 1-32, wherein in step (c) the measuring a latent inhibition response of the individual to calculate a latent inhibition score further comprises comparing the latent inhibition score to a reference score comprising a standard range of latent inhibition scores.

34. The method of embodiment 33, wherein the reference score is based on values obtained from normal individuals, values obtained from different types of patients, and/or values obtained from the same individual on one or more prior testings.

35. The method of embodiment 33 or 34, wherein the standard range latent inhibition scores is based on 20 or more, 30 or more, 40 or more, 50 or more, 60 or more, 70 or more, 80 or more, 90 or more, or 100 or more healthy individuals.

36. The method of any one of embodiments 33-35, wherein when a latent inhibition score is above the reference score, the latent inhibition score is indicative of an enhanced latent inhibition response; when a latent inhibition score is within the standard range latent inhibition scores of the reference score, the latent inhibition score is indicative of a normal latent inhibition response; and when a latent inhibition score is below the reference score, the latent inhibition score is indicative of an attenuated latent inhibition response.

37. The method of any one of embodiments 1-36, wherein in step (d):
   a. when an attenuated latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, the individual is predicted to be currently at an ultra-high risk for the psychotic disorder;
   b. when a normal latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, the individual is predicted not to be currently at an ultra-high risk for the psychotic disorder; or
   c. when an enhanced latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, the individual is predicted to be currently at an ultra-high risk for the psychotic disorder and is likely to have a treatment resistant form of the disorder.

38. The method of any one of embodiments 1-36, wherein in step (d):
   a. when an attenuated latent inhibition response is calculated in step (c) and the information in step (a) indicates that this is an initial assessment, the individual is currently experiencing psychotic symptoms, the individual has no history of a psychotic disorder, and the individual has no history of resistant to anti-psychotic drug treatment, the individual is predicted to be suffering a first episode of the psychotic disorder;
   b. when a normal latent inhibition response is calculated in step (c) and the information in step (a) indicates that this is an initial assessment, the individual is currently experiencing psychotic symptoms, the individual has no history of a psychotic disorder, and the individual has no history of resistant to anti-psychotic drug treatment, the individual is predicted not to be suffering a first episode of the psychotic disorder; or
   c. when an enhanced latent inhibition response is calculated in step (c) and the information in step (a) indicates that this is an initial assessment, the individual is currently experiencing psychotic symptoms, the individual has no history of a psychotic disorder, and the individual has no history of resistant to anti-psychotic drug treatment, the individual is predicted to be suffering a first episode of the psychotic disorder and is likely to have a treatment resistant form of the disorder.

39. The method of any one of embodiments 1-36, wherein in step (d):
   a. when an attenuated latent inhibition response is calculated in step (c) and the information in step (a) indicates that the individual has a history of a psychotic disorder, and the individual has no history of resistant to anti-psychotic drug treatment, the individual is predicted to be suffering from the psychotic disorder;
   b. when a normal latent inhibition response is calculated in step (c) and the information in step (a) indicates that the individual has a history of a psychotic disorder, and the individual has no history of resistant to anti-psychotic drug treatment, the individual is predicted not to be suffering from the psychotic disorder; or
   c. when an enhanced latent inhibition response is calculated in step (c) and the information in step (a) indicates that the individual has a history of a psychotic disorder, and the individual has no history of resistant to anti-psychotic drug treatment, the individual is predicted to be suffering from the psychotic disorder.

40. The method of any one of embodiments 1-36, wherein in step (d):
   a. when an attenuated latent inhibition response is calculated in step (c) and the information in step (a) indicates that the individual is currently experiencing psychotic symptoms, the individual has a history of a psychotic disorder, and the individual has a history of resistant to an anti-psychotic drug treatment, the individual is predicted to be suffering from a treatment-resistant form of the psychotic disorder;
   b. when a normal latent inhibition response is calculated in step (c) and the information in step (a) indicates that the individual is currently experiencing psychotic symptoms, the individual has a history of a psychotic disorder, and the individual has a history of resistant to an anti-psychotic drug treatment, the individual is predicted to be suffering from a treatment-resistant form of the psychotic disorder; or
   c. when an enhanced latent inhibition response is calculated in step (c) and the information in step (a) indicates that the individual is currently experiencing psychotic symptoms, the individual has a history of a psychotic disorder, and the individual has a history of resistant to an anti-psychotic drug treatment, the individual is predicted to not be suffering from a treatment-resistant form of the psychotic disorder.

41. The method of any one of embodiments 1-36, further comprising evaluating working memory.

42. The method of embodiment 41, wherein working memory is evaluated in the pre-exposure phase by providing instructions which require the individual to respond to a current stimulus of the first group of stimuli only if the current stimulus is the same as a stimulus shown one position back in a sequence of the first group of stimuli.

43. The method of embodiment 41, wherein working memory is evaluated in the pre-exposure phase by providing instructions which require the individual to respond to a current stimulus of the first group of stimuli only if the current stimulus is the same as a stimulus shown two positions back in a sequence of the first group of stimuli.

44. The method of any one of embodiments 41-43, wherein assignment is based on whether the latent inhibition score of the individual is indicative of an attenuated latent inhibition response, a normal latent inhibition response, or an enhanced latent inhibition response and whether the individual exhibits a deficit in working memory or not.

45. The method of any one of embodiments 41-44, wherein working memory is calculated by: counting the number of pre-exposure responses presented based on the presentation back stimulus; counting the number of pre-exposure responses selected correctly by the individual based on the presentation back stimulus; and calculating the percent of pre-exposure responses selected correctly by the individual, wherein 50% or more is indicative of a working memory.

46. The method of any one of embodiments 41-44, wherein working memory is calculated by: counting the number of pre-exposure responses selected incorrectly by the individual based on the presentation back stimulus; and calculating the percent of pre-exposure responses selected incorrectly by the individual, wherein 50% or more is indicative of impaired working memory.

47. The method of any one of embodiments 41-44, wherein working memory is calculated by: calculating the average reaction time of pre-exposure responses selected incorrectly by the individual;

48. The method of any one of embodiments 41-44, wherein working memory is calculated by: calculating a d' score of pre-exposure responses presented based on the presentation of back stimulus.

49. The method of any one of embodiments 41-48, wherein in step (d):
   a. when an attenuated latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is a deficit in working memory, the individual is predicted to be currently at an ultra-high risk for the psychotic disorder;
   b. when an attenuated latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, and there is not a deficit in working memory, the individual is predicted not to be currently at an ultra-high risk for the psychotic disorder;
   c. when a normal latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is a deficit in working memory, the individual is predicted to be currently at an ultra-high risk for the psychotic disorder;
   d. when a normal latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is not a deficit in working memory, the individual is predicted to not be currently at an ultra-high risk for the psychotic disorder;
   e. when an enhanced latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is a deficit in working memory, the individual is predicted to be currently at an ultra-high risk for the psychotic disorder; or
   f. when an enhanced latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is not a deficit in working memory, the individual is predicted to not be currently at an ultra-high risk for the psychotic disorder.

50. The method of any one of embodiments 41-48, wherein in step (d):
   a. when an attenuated latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder;
   b. when an attenuated latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted to be suffering a first episode of the psychotic disorder;

c. when a normal latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder;

d. when a normal latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted not to be suffering a first episode of the psychotic disorder;

e. when an enhanced latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder; or f. when an enhanced latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted to be suffering a first episode of the psychotic disorder.

51. The method of any one of embodiments 41-48, wherein in step (d):

a. when an attenuated latent inhibition response is calculated in step (c), the information in step (a) indicates that the individual has a history of a psychotic disorder, and the individual has no history of resistant to anti-psychotic drug treatment, and there is a deficit in working memory, the individual is predicted to be suffering from the psychotic disorder;

b. when an attenuated latent inhibition response is calculated in step (c), the information in step (a) indicates that the individual has a history of a psychotic disorder, and the individual has no history of resistant to anti-psychotic drug treatment, and there is not a deficit in working memory, the individual is predicted to be suffering from the psychotic disorder;

c. when a normal latent inhibition response is calculated in step (c), the information in step (a) indicates that the individual has a history of a psychotic disorder, and the individual has no history of resistant to anti-psychotic drug treatment, and there is a deficit in working memory, the individual is predicted to be suffering from the psychotic disorder;

d. when a normal latent inhibition response is calculated in step (c), the information in step (a) indicates that the individual has a history of a psychotic disorder, and the individual has no history of resistant to anti-psychotic drug treatment, and there is not a deficit in working memory, the individual is predicted not to be suffering from the psychotic disorder;

e. when an enhanced latent inhibition response is calculated in step (c), the information in step (a) indicates that the individual has a history of a psychotic disorder, and the individual has no history of resistant to anti-psychotic drug treatment, and there is a deficit in working memory, the individual is predicted to be suffering from the psychotic disorder; or f. when an enhanced latent inhibition response is calculated in step (c), the information in step (a) indicates that the individual has a history of a psychotic disorder, and the individual has no history of resistant to anti-psychotic drug treatment, and there is not a deficit in working memory, the individual is predicted to be suffering from the psychotic disorder.

52. The method of any one of embodiments 41-48, wherein in step (d):

a. when an attenuated latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is a deficit in working memory, the individual is predicted to be suffering from a treatment-resistant form of the psychotic disorder;

b. when an attenuated latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is not a deficit in working memory, the individual is predicted to be suffering from a treatment-resistant form of the psychotic disorder;

c. when a normal latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is a deficit in working memory, the individual is predicted not to be suffering from a treatment-resistant form of the psychotic disorder;

d. when a normal latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is not a deficit in working memory, the individual is predicted not to be suffering from a treatment-resistant form of the psychotic disorder; or e. when an enhanced latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is a deficit in working memory, the individual is predicted to be suffering from a treatment-resistant form of the psychotic disorder; or f. when an enhanced latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is not a deficit in working memory, the individual is predicted to be suffering from a treatment-resistant form of the psychotic disorder.

53. The method of any one of embodiments 1-52, wherein the psychotic disorder includes a schizophrenia spectrum disorder, an obsessive-compulsive disorder, an anxiety disorder, a bipolar disorder, or a dementia disease.

54. A computer programmed to carry out the method of any of embodiments 1-53.

55. A computer operating the method of any of embodiments 1-53.

56. A system adapted to carry out the method of any of embodiments 1-53.

57. A storage medium on which is stored or otherwise recorded a computer programme for carrying the method of any of embodiments 1-53.

In other embodiments, a therapy recommendation method can be described as follows:

1. A method of recommending a therapy to treat an individual with a psychotic disorder using a non-invasive computational device-based test, the method comprising:
   a. optionally entering information about the individual into a latent inhibition test program running on a computational device, the information including:
      i. whether this is an initial assessment or a subsequent assessment;
      ii. whether or not the individual is currently experiencing psychotic symptoms;
      iii. whether or not the individual has a history of a psychotic disorder; and/or
      iv. whether or not the individual has a history of resistance to anti-psychotic drug treatment
   b. having the individual perform a latent inhibition assessment using the latent inhibition test program running on the computational device and a graphical user interface coupled thereto with which the individual interacts, the latent inhibition assessment comprising a pre-exposure phase and a test phase,
      i. wherein the pre-exposure phase includes,
         presenting the individual with a first set of directions for how to respond to each stimulus of a first group of stimuli, wherein the first set of directions include pre-exposure phase instructions which require the individual to respond to each stimulus of the first group of stimuli in a defined manner;
         presenting the individual with a random order of the first group of stimuli, each stimulus being presented for 10 msec to 10,000 msec, wherein the first group of stimuli comprises a plurality of stimuli including at least one preexposed stimulus and one or more neutral stimuli;
      ii. wherein the test phase includes,
         presenting the individual with a second set of directions for how to respond to each stimulus of a second group of stimuli, wherein the second set of directions include test phase instructions which require the individual to anticipate the occurrence of a target stimulus;
         presenting the individual with the second group of stimuli, each stimulus being presented for 10 msec to 10,000 msec with a 0 msec to 10,000 msec interval between each stimulus, wherein the second group of stimuli comprises a plurality of stimuli including the at least one preexposed stimuli, a non-preexposed stimulus, the target stimulus, and the one or more neutral stimuli;
         recording and analyzing the individual's interaction with the graphical user interface following presentation of the second group of stimuli, by
         measuring a time associated with a target anticipated response of the individual to each stimulus from the plurality of stimuli, wherein a response to the target stimulus of less than the sum of the presentation time and interval time according to the second set of directions is indicative that the individual anticipated the occurrence of the target stimulus, and wherein a response to the target stimulus of equal to or more than the sum of the presentation time and interval time according to the second set of directions is indicative that the individual failed to anticipate the occurrence of the target stimulus;
   c. measuring a latent inhibition response of the individual to calculate a latent inhibition score, by modeling the time associated with a target anticipated response in one or more statistical analyses that analyze one or more of a count of a number of presentations on which the response to the targeted stimulus occurred, a central tendency of the number of responses to the target stimulus, or a distance from a central tendency of the number of the responses to the target stimulus, and determining whether the individual exhibited an attenuated latent inhibition response, a normal latent inhibition response or an enhanced latent inhibition response from the latent inhibition score; and
   d. calculating the recommend therapy to treat an individual, the recommend therapy including either i) no therapy recommendation; or ii) treating with a pro-cognitive drug, treating with an anti-psychotic drug, treating with clozapine or an alternative drug for treatment-resistant psychotic symptoms, or any combination thereof.

2. The method of embodiment 1, wherein the information entered for (a)(iv) includes whether or not the individual is resistant to an anti-psychotic drug.

3. The method of embodiment 1 or 2, wherein the pre-exposure phase instructions require the individual to respond to a stimulus of the first group of stimuli as it appears on the screen.

4. The method of embodiment 1, or 2 wherein the pre-exposure phase instructions require the individual to respond to a current stimulus of the first group of stimuli only if the current stimulus is the same as a stimulus shown one position back in a sequence of the first group of stimuli.

5. The method of embodiment 1 or 2, wherein the pre-exposure phase instructions require the individual to respond to a current stimulus of the first group of stimuli only if the current stimulus is the same as a stimulus shown two positions back in a sequence of the first group of stimuli.

6. The method of any one of embodiments 1-5, wherein each stimulus is presented for is 100 msec to 5,000 msec, 250 msec to 2,500 msec, 500 msec to 1,500 msec, 750 msec to 1,250 msec, or 1,000 msec
7. The method of any one of embodiments 1-6, wherein step (b)(i) further comprising an interval between each stimulus.
8. The method of embodiment 7, wherein interval between each stimulus is 1 msec to 10,000 msec, 5 msec to 1,000 msec, 10 msec to 500 msec, 15 msec to 250 msec, 20 msec to 100 msec, 25 msec to 75 msec, or 50 msec
9. The method of any one of embodiments 1-8, wherein step (b)(i) further comprises measuring a response of the individual to each stimulus from the first group of stimuli.
10. The method of any one of embodiments 1-9, wherein if the individual responses to at least 50%, at least 55%, at least 60%, at least 65%, at least 70%, at least 75%, at least 80%, at least 85%, at least 90%, or at least 95% of the first group of stimuli according to the first set of directions, the program proceeds to the test phase of step (b)(ii).
11. The method of any one of embodiments 1-10, wherein in step (b)(ii) if the sum of the presentation time and interval time is less than 550 msec, less than 750 msec, less than 950 msec, less than 1,050 msec, less than 1,150 msec, less than 1,350 msec, less than 1,550 msec, less than 1,750 msec, less than 1,950 msec, less than 2,150 msec, less than 2,350 msec, or less than 2,550 msec, then the individual anticipated the occurrence of the target stimulus.
12. The method of any one of embodiments 1-11, wherein in step (b)(ii) if the sum of the presentation time and interval time is 550 msec or more, 750 msec or more, 950 msec or more, 1,050 msec or more, 1,150 msec or more, 1,350 msec or more, 1,550 msec or more, 1,750 msec or more, 1,950 msec or more, 2,150 msec or more, 2,350 msec or more, 2,550 msec or more, then the individual failed to anticipate the occurrence of the target stimulus.
13. The method of any one of embodiments 1-12, wherein in step (b)(ii) an equal number of presentations for the target stimulus occurs after presentation of the preexposed stimulus and after presentation of the non-preexposed stimulus
14. The method of any one of embodiments 1-13, wherein in step (b)(ii) an unequal number of presentations for the target stimulus occurs after presentation of the preexposed stimulus relative to after presentation of the non-preexposed stimulus
15. The method of embodiment 14, wherein the unequal number of presentations for the target stimulus occurring after presentation of the preexposed stimulus is ±10%, 20%, 30%, 40%, 50% the number of presentations for the target stimulus occurring after presentation of the non-preexposed stimulus.
16. The method of any one of embodiments 1-15, wherein in step (c) the latent inhibition score is calculated by determining one or more reaction times.
17. The method of embodiment 16, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target anticipated response measured when the target stimulus was presented after presentation of the preexposed stimulus; and calculating the latent inhibition score by subtracting the second average time by the first average time.
18. The method of embodiment 16, wherein measuring a latent inhibition response of the individual to calculate a latent inhibition score further comprises: calculating a first average time based on each target anticipated response measured when the target stimulus was presented after presentation of the non-preexposed stimulus; calculating a second average time based on each target anticipated response measured when the target stimulus was presented after presentation of the preexposed stimulus; and calculating the latent inhibition score by subtracting the first average time by the second average time.
19. The method of embodiment 16, wherein the measuring a latent inhibition response of the individual to calculate a latent inhibition score further comprises: calculating a first average time based on each target anticipated response measured when the target stimulus was presented after presentation of the non-preexposed stimulus; calculating a second average time based on each target prediction response measured when the target stimulus was presented after presentation of the preexposed stimulus; and calculating the latent inhibition score by determining whether the first average time is slower or faster than the second average time.
20. The method of embodiment 16, wherein the measuring a latent inhibition response of the individual to calculate a latent inhibition score further comprises: pairing each target anticipatory response time based on the non-preexposed stimulus with a target anticipatory response time based on the preexposed stimulus; calculating whether a paired target anticipatory response time based on the non-preexposed stimulus was faster relative to its paired target anticipatory response time based on the preexposed stimulus; calculating the latent inhibition score by determining (i) the total number of paired target anticipatory response times based on the non-preexposed stimulus that were higher relative to their paired target anticipatory response time based on the preexposed stimulus, (ii) the total number of paired target anticipatory response times based on the non-preexposed stimulus that were lower relative to their paired target anticipatory response time based on the preexposed stimulus, or (iii) both (i) and (ii).
21. The method of any one of embodiments 1-15, wherein in step (c) the latent inhibition score is calculated by determining a number of anticipatory responses.
22. The method of embodiment 21, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by subtracting the second average number of anticipatory responses by the first average number of anticipatory responses.
23. The method of embodiment 21, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by subtracting the first average number of anticipatory responses by the second average number of anticipatory responses.
24. The method of embodiment 21, wherein the measuring a latent inhibition response of the individual to calculate a latent inhibition score further comprises: calculating a first average number of anticipatory responses based on each target anticipated response measured when the target stimulus was presented after presentation of the non-preexposed stimulus; calculating a second average number of anticipatory responses based on each target anticipated response measured when the target stimulus was presented after presentation of the preexposed stimulus; and calculating the latent inhibition score by determining whether the first average number of anticipatory responses is lower or higher than the second average number of anticipatory responses.
25. The method of embodiment 21, wherein the measuring a latent inhibition response of the individual to calculate a latent inhibition score further comprises: pairing each target anticipatory response based on the non-preexposed stimulus with a target anticipatory response based on the preexposed stimulus; calculating whether a paired target anticipatory response time based on the non-preexposed stimulus was faster relative to its paired target anticipatory response time based on the preexposed stimulus; calculating the latent inhibition score by determining (i) the total number of paired target anticipatory response times based on the non-preexposed stimulus that were higher relative to their paired target anticipatory response time based on the preexposed stimulus, (ii) the total number of paired target anticipatory response times based on the non-preexposed stimulus that were lower relative to their paired target anticipatory response time based on the preexposed stimulus, or (iii) both (i) and (ii).
26. The method of any one of embodiments 1-15, wherein in step (c) the latent inhibition score is calculated by determining a percentage of anticipatory responses.
27. The method of embodiment 26, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by subtracting the second percent of anticipatory responses by the first percent of anticipatory responses.
28. The method of embodiment 26, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by subtracting the first percent of anticipatory responses by the second percent of anticipatory responses.
29. The method of embodiment 26, wherein the measuring a latent inhibition response of the individual to calculate a latent inhibition score further comprises: calculating a first percent of anticipatory responses based on each target anticipated response measured when the target stimulus was presented after presentation of the non-preexposed stimulus; calculating a second percent of anticipatory responses based on each target anticipated response measured when the target stimulus was presented after presentation of the preexposed stimulus; and calculating the latent inhibition score by determining whether the first percent of anticipatory responses is lower or higher than the second percent of anticipatory responses.
30. The method of any one of embodiments 1-15, wherein in step (c) the latent inhibition score is calculated by determining an accuracy-sensitivity d' score.
31. The method of embodiment 30, wherein the first d' score and the second d' score are calculated by: calculating a first d' score of anticipatory responses based on each target anticipated response measured when the target stimulus was presented after presentation of the non-preexposed stimulus; calculating a second d' score of anticipatory responses based on each target anticipated response measured when the target stimulus was presented after presentation of the preexposed stimulus; and calculating the latent inhibition score by subtracting the second d' score of anticipatory responses by the first d' score of anticipatory responses.
32. The method of embodiment 30, wherein the first d' score and the second d' score are calculated by: calculating a hit rate by dividing the totaling the number of correctly identified back targets by the total number of back targets; calculating a false alarm rate, by dividing the number of responses for stimuli erroneously identified as back targets by the total number of back targets; and applying a z-transformation to the hit rate and the false alarm rate and subtracting the resulting transformed false alarm rate from the resulting transformed hit rate to obtain the d' score.
33. The method of any one of embodiments 1-32, wherein in step (c) the measuring a latent inhibition response of the individual to calculate a latent inhibition score further comprises comparing the latent inhibition score to a reference score comprising a standard range of latent inhibition scores.
34. The method of embodiment 33, wherein the reference score is based on values obtained from normal individuals, values obtained from different types of patients, and/or values obtained from the same individual on one or more prior testings.
35. The method of embodiment 33 or 34, wherein the standard range latent inhibition scores is based on 20 or more, 30 or more, 40 or more, 50 or more, 60 or more, 70 or more, 80 or more, 90 or more, or 100 or more healthy individuals.
36. The method of any one of embodiments 33-35, wherein when a latent inhibition score is above the reference score, the latent inhibition score is indicative of an enhanced latent inhibition response; when a latent inhibition score is within the standard range latent inhibition scores of the reference score, the latent inhibition score is indicative of a normal latent inhibition response; and when a latent inhibition score is below the reference score, the latent inhibition score is indicative of an attenuated latent inhibition response.

37. The method of any one of embodiments 1-36, wherein in step (d):
    a. when an attenuated latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, the individual is predicted to be currently at an ultra-high risk for the psychotic disorder and a therapy recommendation includes treating with an anti-psychotic drug;
    b. when a normal latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, the individual is predicted not to be currently at an ultra-high risk for the psychotic disorder and no therapy recommendation is provided; or
    c. when an enhanced latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, the individual is predicted to be currently at an ultra-high risk for the psychotic disorder and a therapy recommendation includes treating with a pro-cognitive drug.

38. The method of any one of embodiments 1-36, wherein in step (d):
    a. when an attenuated latent inhibition response is calculated in step (c) and the information in step (a) indicates that this is an initial assessment, the individual is currently experiencing psychotic symptoms, the individual has no history of a psychotic disorder, and the individual has no history of resistant to anti-psychotic drug treatment, the individual is predicted to be suffering a first episode of the psychotic disorder and a therapy recommendation includes treating with an anti-psychotic drug;
    b. when a normal latent inhibition response is calculated in step (c) and the information in step (a) indicates that this is an initial assessment, the individual is currently experiencing psychotic symptoms, the individual has no history of a psychotic disorder, and the individual has no history of resistant to anti-psychotic drug treatment, the individual is predicted not to be suffering a first episode of the psychotic disorder and a therapy recommendation includes maintaining a current treatment; or
    c. when an enhanced latent inhibition response is calculated in step (c) and the information in step (a) indicates that this is an initial assessment, the individual is currently experiencing psychotic symptoms, the individual has no history of a psychotic disorder, and the individual has no history of resistant to anti-psychotic drug treatment, the individual is predicted to be suffering a first episode of the psychotic disorder and a therapy recommendation includes treating with clozapine or an alternative drug for treatment-resistant psychotic symptoms and a pro-cognitive drug.

39. The method of any one of embodiments 1-36, wherein in step (d):
    a. when an attenuated latent inhibition response is calculated in step (c) and the information in step (a) indicates that the individual has a history of a psychotic disorder, and the individual has no history of resistant to anti-psychotic drug treatment, the individual is predicted to be suffering from the psychotic disorder and a therapy recommendation includes treating with an anti-psychotic drug and a pro-cognitive drug;
    b. when a normal latent inhibition response is calculated in step (c) and the information in step (a) indicates that the individual has a history of a psychotic disorder, and the individual has no history of resistant to anti-psychotic drug treatment, the individual is predicted not to be suffering from the psychotic disorder and a therapy recommendation includes maintaining a current treatment; or
    c. when an enhanced latent inhibition response is calculated in step (c) and the information in step (a) indicates that the individual has a history of a psychotic disorder, and the individual has no history of resistant to anti-psychotic drug treatment, the individual is predicted to be suffering from the psychotic disorder and a therapy recommendation includes treating with a pro-cognitive drug as an add on therapy to current treatment.

40. The method of any one of embodiments 1-36, wherein in step (d):
    a. when an attenuated latent inhibition response is calculated in step (c) and the information in step (a) indicates that the individual is currently experiencing psychotic symptoms, the individual has a history of a psychotic disorder, and the individual has a history of resistant to an anti-psychotic drug treatment, the individual is predicted to be suffering from a treatment-resistant form of the psychotic disorder and a therapy recommendation includes treating with an anti-psychotic drug and a pro-cognitive drug;
    b. when a normal latent inhibition response is calculated in step (c) and the information in step (a) indicates that the individual is currently experiencing psychotic symptoms, the individual has a history of a psychotic disorder, and the individual has a history of resistant to an anti-psychotic drug treatment, the individual is predicted not to be suffering from a treatment-resistant form of the psychotic disorder and a therapy recommendation includes maintaining a current treatment; or
    c. when an enhanced latent inhibition response is calculated in step (c) and the information in step (a) indicates that the individual is currently experiencing psychotic symptoms, the individual has a history of a psychotic disorder, and the individual has a history of resistant to an anti-psychotic drug treatment, the individual is predicted to be suffering from a treatment-resistant form of the psychotic disorder and a therapy recommendation includes treating with clozapine or an alternative drug for treatment-resistant psychotic symptoms and a pro-cognitive drug.
41. The method of any one of embodiments 1-36, wherein in step (d):
   a. when an attenuated latent inhibition response calculated in step (c) and the information in step (a) indicates that this was a subsequent assessment, a therapy recommendation includes increasing the drug dose of a current treatment;
   b. when a normal latent inhibition response calculated in step (c) and the information in step (a) indicates that this was a subsequent assessment, a therapy recommendation includes maintaining a current treatment and dose; or
   c. when an enhanced latent inhibition response calculated in step (c) and the information in step (a) indicates that this was a subsequent assessment, a therapy recommendation includes decreasing the drug dose of a current treatment.
42. The method of any one of embodiments 1-36, further comprising evaluating working memory.
43. The method of embodiment 42, wherein working memory is evaluated in the pre-exposure phase by providing instructions which require the individual to respond to a current stimulus of the first group of stimuli only if the current stimulus is the same as a back stimulus shown one position back in a sequence of the first group of stimuli.
44. The method of embodiment 42, wherein working memory is evaluated in the pre-exposure phase by providing instructions which require the individual to respond to a current stimulus of the first group of stimuli only if the current stimulus is the same as a back stimulus shown two positions back in a sequence of the first group of stimuli.
45. The method of any one of embodiments 42-44, wherein assignment is based on whether the latent inhibition score of the individual is indicative of an attenuated latent inhibition response, a normal latent inhibition response, or an enhanced latent inhibition response and whether the individual exhibits a deficit in working memory or not.
46. The method of any one of embodiments 42-45, wherein working memory is calculated by: counting the number of pre-exposure responses presented based on the presentation back stimulus; counting the number of pre-exposure responses selected correctly by the individual based on the presentation back stimulus; and calculating the percent of pre-exposure responses selected correctly by the individual, wherein 50% or more is indicative of a working memory.
47. The method of any one of embodiments 42-45, wherein working memory is calculated by: counting the number of pre-exposure responses selected incorrectly by the individual based on the presentation back stimulus; and calculating the percent of pre-exposure responses selected incorrectly by the individual, wherein 50% or more is indicative of impaired working memory.
48. The method of any one of embodiments 42-45, wherein working memory is calculated by: calculating the average reaction time of pre-exposure responses selected incorrectly by the individual.
49. The method of any one of embodiments 42-45, wherein working memory is calculated by: calculating a d' score of pre-exposure responses presented based on the presentation of back stimulus.
50. The method of any one of embodiments 42-49, wherein in step (d):
   a. when an attenuated latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is a deficit in working memory, the individual is predicted to be currently at an ultra-high risk for the psychotic disorder and a therapy recommendation includes treating with an anti-psychotic and a pro-cognitive drug;
   b. when an attenuated latent inhibition response is calculated in step (c) and the information in step (a) indicates that this is an initial assessment, the individual is not currently experiencing psychotic symptoms, the individual has no history of a psychotic disorder, and the individual has no history of resistant to anti-psychotic drug treatment, and there is not a deficit in working memory, the individual is predicted not to be currently at an ultra-high risk for the psychotic disorder and no therapy recommendation is provided;
   c. when a normal latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is a deficit in working memory, the individual is predicted to be currently at an ultra-high risk for the psychotic disorder and a therapy recommendation includes treating with a pro-cognitive drug;
   d. when a normal latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is not a deficit in working memory, the individual is predicted to not be currently at an ultra-high risk for the psychotic disorder and no therapy recommendation is provided;
   e. when an enhanced latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is a deficit in working memory, the individual is predicted to be currently at an ultra-high risk for the psychotic disorder and a therapy recommendation includes treating with a pro-cognitive drug; or
   f. when an enhanced latent inhibition response is calculated in step (c), the information in step (a) indicates that this is an initial assessment, the individual is not currently experiencing psychotic symptoms, the individual has no history of a psychotic disorder, and the individual has no history of resistant to anti-psychotic drug treatment, and there is not a deficit in working memory, the individual is predicted to not be currently at an ultra-high risk for the psychotic disorder and no therapy recommendation is provided;

51. The method of any one of embodiments 42-49, wherein in step (d):
    a. when an attenuated latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder and a therapy recommendation includes treating with an anti-psychotic drug and a pro-cognitive drug;
    b. when an attenuated latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted to be suffering a first episode of the psychotic disorder and a therapy recommendation includes treating with an anti-psychotic drug;
    c. when a normal latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder and a therapy recommendation includes maintaining a current treatment and a further treating with a pro-cognitive drug;
    d. when a normal latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted not to be suffering a first episode of the psychotic disorder and a therapy recommendation includes maintaining a current treatment;
    e. when an enhanced latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is a deficit in working memory, the individual is predicted to be suffering a first episode of the psychotic disorder and a therapy recommendation includes treating with clozapine or an alternative drug for treatment-resistant psychotic symptoms and a pro-cognitive drug; or
    f. when an enhanced latent inhibition response is calculated in step (c), the information in step (a) indicates that this is an initial assessment, the individual is currently experiencing psychotic symptoms, the individual has no history of a psychotic disorder, and the individual has no history of resistant to anti-psychotic drug treatment, and there is not a deficit in working memory, the individual is predicted to be suffering a first episode of the psychotic disorder and a therapy recommendation includes treating with a pro-cognitive drug.

52. The method of any one of embodiments 42-49, wherein in step (d):
    a. when an attenuated latent inhibition response is calculated in step (c), the information in step (a) indicates that the individual has a history of a psychotic disorder, and the individual has no history of resistant to anti-psychotic drug treatment, and there is a deficit in working memory, the individual is predicted to be suffering from the psychotic disorder and a therapy recommendation includes treating with an anti-psychotic drug and a pro-cognitive drug;
    b. when an attenuated latent inhibition response is calculated in step (c), the information in step (a) indicates that the individual has a history of a psychotic disorder, and the individual has no history of resistant to anti-psychotic drug treatment, and there is not a deficit in working memory, the individual is predicted to be suffering from the psychotic disorder and a therapy recommendation includes treating with an anti-psychotic drug;
    c. when a normal latent inhibition response is calculated in step (c), the information in step (a) indicates that the individual has a history of a psychotic disorder, and the individual has no history of resistant to anti-psychotic drug treatment, and there is a deficit in working memory, the individual is predicted to be suffering from the psychotic disorder and a therapy recommendation includes treating with a pro-cognitive drug in addition to maintaining a current treatment;
    d. when a normal latent inhibition response is calculated in step (c), the information in step (a) indicates that the individual has a history of a psychotic disorder, and the individual has no history of resistant to anti-psychotic drug treatment, and there is not a deficit in working memory, the individual is predicted not to be suffering from the psychotic disorder and a therapy recommendation includes maintaining a current treatment;
    e. when an enhanced latent inhibition response is calculated in step (c), the information in step (a) indicates that the individual has a history of a psychotic disorder, and the individual has no history of resistant to anti-psychotic drug treatment, and there is a deficit in working memory, the individual is predicted to be suffering from the psychotic disorder and a therapy recommendation includes treating with an anti-psychotic drug and a pro-cognitive drug; or
    f. when an enhanced latent inhibition response is calculated in step (c), the information in step (a) indicates that the individual has a history of a psychotic disorder, and the individual has no history of resistant to anti-psychotic drug treatment, and there is not a deficit in working memory, the individual is predicted to be suffering from the psychotic disorder and a therapy recommendation includes treating with a pro-cognitive drug.

53. The method of any one of embodiments 42-49, wherein in step (d):
   a. when an attenuated latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is a deficit in working memory, the individual is predicted to be suffering from a treatment-resistant form of the psychotic disorder and a therapy recommendation includes treating with an anti-psychotic drug and a pro-cognitive drug;
   b. when an attenuated latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is not a deficit in working memory, the individual is predicted to be suffering from a treatment-resistant form of the psychotic disorder and a therapy recommendation includes treating with an anti-psychotic drug;
   c. when a normal latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is a deficit in working memory, the individual is predicted not to be suffering from a treatment-resistant form of the psychotic disorder and a therapy recommendation includes maintaining a current treatment and further treating with a pro-cognitive drug;
   d. when a normal latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is not a deficit in working memory, the individual is predicted not to be suffering from a treatment-resistant form of the psychotic disorder and a therapy recommendation includes maintaining a current treatment;
   e. when an enhanced latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is a deficit in working memory, the individual is predicted to be suffering from a treatment-resistant form of the psychotic disorder and a therapy recommendation includes treating with clozapine or an alternative drug for treatment-resistant psychotic symptoms and a pro-cognitive drug; or
   f. when an enhanced latent inhibition response is calculated in step (c), the information in step (a) indicates that the individual is currently experiencing psychotic symptoms, the individual has a history of a psychotic disorder, and the individual has a history of resistant to an anti-psychotic drug treatment, and there is not a deficit in working memory, the individual is predicted to be suffering from a treatment-resistant form of the psychotic disorder and a therapy recommendation includes treating with clozapine or an alternative drug for treatment-resistant psychotic symptoms and a pro-cognitive drug.

54. The method of any one of embodiments 1-53, wherein the psychotic disorder includes a schizophrenia spectrum disorder, an obsessive-compulsive disorder, an anxiety disorder, a bipolar disorder, or a dementia disease.

55. The method of any one of embodiments 1-54, wherein the pro-cognitive drug is an agonist, antagonist, partial agonist, positive allosteric modulator, negative allosteric modulator, silent allosteric modulator, or inverse agonist of an ionotropic receptor.

56. The method of embodiment 55, wherein the ionotropic receptor is a Nicotinic Acetylcholine (nAch) receptor, an ionotropic Gamma-Aminobutyric Acid (GABA) receptor, an ionotropic Glutamine (Glu) receptor, or an ionotropic Serotonin (5-HT) receptor.

57. The method of embodiment 56, wherein the nAch receptor is $\alpha 4\beta 2$ nAch receptor, $\alpha 3\beta 4$ nAch receptor, $\alpha 7$ nAch receptor.

58. The method of embodiment 56, wherein the ionotropic GABA receptor is a $GABA_A$ receptor or a $GABA_{A\text{-}\rho}$ receptor.

59. The method of embodiment 56, wherein the ionotropic Glutamine receptor is an N-methyl-D-aspartate receptor, a Kainate receptor, or an α-amino-3-hydroxy-5-methyl-4-isoxazolepropionic acid receptor.

60. The method of embodiment 56, wherein the ionotropic 5-HT receptor is a $5\text{-}HT_3$ receptor.

61. The method of any one of embodiments 1-54, wherein the pro-cognitive drug is an agonist, antagonist, partial agonist, positive allosteric modulator, negative allosteric modulator, silent allosteric modulator, or inverse agonist of an metabotropic receptor.

62. The method of embodiment 61, wherein the metabotropic receptor is a Muscarinic Acetylcholine (mAch) receptor, a Cannabinoid (CB) receptor, a Dopamine (DA) receptor, an Endorphin receptor, a metabotropic Gamma-Aminobutyric Acid (GABA) receptor, a metabotropic Glutamine (Glu) receptor, a Norepinephrine (NE) receptor, an Oxytocin receptor, a metabotropic Serotonin (5-HT) receptor.

63. The method of embodiment 62, wherein the mAch receptor is a $M_1$ mAch receptor, $M_2$ mAch receptor, $M_3$ mAch receptor, $M_4$ mAch receptor, or $M_5$ mAch receptor.

64. The method of embodiment 62, wherein the CB receptor is a CB1 receptor or CB2 receptor.

65. The method of embodiment 62, wherein the DA receptor is a $DA_1$ receptor, a $DA_2$ receptor, a $DA_3$ receptor, a $DA_4$ receptor, or a $DA_5$ receptor and heterodimers thereof.

66. The method of embodiment 62, wherein the Endorphin receptor is a $\mu_1$ Opioid receptor, a $\mu_2$ Opioid receptor, or a $\mu_3$ Opioid receptor.

67. The method of embodiment 62, wherein the metabotropic GABA receptor is a $GABA_B$ receptor.

68. The method of embodiment 62, wherein the metabotropic Glu receptor is a Glu $receptor_1$, Glu $receptor_2$, Glu $receptor_3$, Glu $receptor_4$, Glu $receptor_5$, Glu $receptor_6$, Glu $receptor_7$, or Glu $receptor_8$.

69. The method of embodiment 62, wherein the NE receptor is an $\alpha_1$ Adrenergic receptor, an $\alpha_2$ Adrenergic receptor, a $\beta_1$ Adrenergic receptor, a $\beta_2$ Adrenergic receptor, or a $\beta_3$ Adrenergic receptor.

70. The method of embodiment 62, wherein the metabotropic 5-HT receptor is a $5-HT_1$ receptor, a $5-HT_2$ receptor, a $5-HT_4$ receptor, a $5-HT_5$ receptor, a $5-HT_6$ receptor, or a $5-HT_7$ receptor.
71. The method of any one of embodiments 1-54, wherein the pro-cognitive drug is an agonist, antagonist, partial agonist, positive allosteric modulator, negative allosteric modulator, silent allosteric modulator, or inverse agonist of a phosphodiesterase (PDE).
72. The method of embodiment 71, wherein the PDE is a $PDE_1$, a $PDE_2$, a $PDE_3$, a $PDE_4$, a $PDE_5$, a $PDE_6$, a $PDE_7$, a $PDE_3$, a $PDE_9$, or a $PDE_{10}$.
73. The method of any one of embodiments 1-72, wherein the anti-psychotic drug is a dopamine antagonist, a serotonin-dopamine antagonist or a partial dopamine agonist.
74. The method of embodiment 73, wherein the dopamine antagonist includes Chlorpromazine, Haloperidol, Loxapine, Perphenazine, Prochlorperazine, Thiothixene, Thioridazine, and Trifluoperazine.
75. The method of embodiment 74, wherein the serotonin-dopamine antagonist includes Olanzapine, Paliperidone, Quetiapine, and Risperidone.
76. The method of embodiment 74, wherein the partial dopamine agonist includes Aripiprazole.
77. A computer programmed to carry out the method of any of embodiments 1-76.
78. A computer operating the method of any of embodiments 1-76.
79. A system adapted to carry out the method of any of embodiments 1-76.
80. A storage medium on which is stored or otherwise recorded a computer programme for carrying the method of any of embodiments 1-76.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods and uses disclosed herein.

Example 1

Pre-Exposure Phase Instructions

This example provides exemplary pre-exposure phase instructions given to an individual during a first set of directions for how to respond to each stimulus of a first group of stimuli during a pre-exposure phase disclosed herein.

0-back pre-exposure phase instructions. In this task you will see a sequence of letters appearing on the screen. Your task is to say each of the letters out loud as you see them appear. When this task ends, you will be given a new set of instructions. Press the button on screen when you are ready to begin.

1-back pre-exposure phase instructions. In this task you will see a sequence of letters appearing on the screen. Your task is to press the response button at the bottom of the screen each time the current letter is the same as the one presented just before. Otherwise, do not respond. When this task ends, you will be given a new set of instructions. Press the button on screen when you are ready to begin.

2-back pre-exposure phase instructions. In this task you will see a sequence of letters appearing on the screen. Your task is to press the response button at the bottom of the screen each time the current letter is the same as the one that was presented before last, that is 2 positions back in the sequence. Otherwise, do not respond. When this task ends, you will be given a new set of instructions. Press the button on screen when you are ready to begin.

Example 2

Test Phase Instructions

This example provides exemplary test phase instructions given to an individual during a second set of directions for how to respond to each stimulus of a second group of stimuli during a pre-exposure phase disclosed herein.

Test Phase instructions. In this task you will see a sequence of letters appearing on the screen. Your task is to try and predict when a letter 'X' is going to appear. If you think you know when the 'X' will appear then you can press the response button early in the sequence, that is before the 'X' appears on screen. Alternatively, if you are unable to do this please press the response button as quickly as possible when you see the letter 'X.' There may be more than one rule that predicts the 'X.' Please try to be as accurate as you can, but do not worry about making the occasional error. If you understand your task and are ready to begin, please press the button on screen.

Example 3

Latent Inhibition Task Assay as a Participant Selection/Screening Tool for Individuals Classified as Ultra-High Risk (UHR)/At Risk Mental State (ARMS) for Psychosis Approximately 30% of individuals classified as ultra-high risk (UHR) for psychosis develop the illness within two years and whilst there are a range of pharmacological and psychosocial interventions available for psychosis, there is great individual variation in clinical response for UHR individuals and no way to determine who may convert to a full-blown psychotic episode. There is need for a biomarker that can better identify individuals at high risk for conversion to psychosis. Latent inhibition has been extensively examined as a model for the different symptoms of psychotic disorders and demonstrates that an attenuation on the test is associated with higher levels of dopamine and psychotic states, whereas an enhancement on the test is associated with low levels of glutamate/acetylcholine and negative and cognitive states. Latent inhibition is used as a cognitive biomarker to prospectively stratify patients and identify those at an increased risk for transition to psychosis and as such will be most likely to respond to particular treatments aimed at improving symptoms or delaying/preventing psychosis onset.

(i) Latent inhibition attenuation: Indicative of high-transition risk with potentially increased likelihood in responsiveness to dopaminergic-based anti-psychotic drug treatments, e.g., dopamine antagonists as latent inhibition score indicates there is a convergence/emergence of psychosis and a hyper-dopaminergic dysfunction underlay the symptoms of psychosis. Recommend treating with a dopaminergic-based anti-psychotic drug.

(ii) Latent inhibition enhancement: Indicative of high-transition risk with potentially increased likelihood of being non-responsive to dopaminergic-based anti-psychotic drug treatments because latent inhibition score indicates cognitive/negative symptoms and a non-dopaminergic dysfunction underlay symptoms of psychosis. Recommend treating with a pro-cognitive drug therapy due to increased likelihood of treatment resistance to dopaminergic-based anti-psychotic drug treatments if individual converts to psychosis, but likely to respond to non-dopaminergic-based drug treatments.

(iii) Latent inhibition within normal range: Indicative of low-transition risk to psychosis and diagnosis as UHR appears to be unwarranted. No drug treatment is recommended.

Example 4

Working Memory Latent Inhibition Assay as a Participant Selection/Screening Tool for Individuals Classified as Ultra-High Risk (UHR)/At Risk Mental State (ARMS) for Psychosis Same use case as above with the addition of working memory assessment during the pre-exposure phase of the latent inhibition task. An assessment of working memory has the additional benefit of being able to determine whether an individual is experiencing a deficit to their working memory in addition to demonstrating a dysfunction of attentional gating though latent inhibition. Individuals that flag up as having a deficit in both latent inhibition and working memory will increase confidence and provide additional information regarding the optimal diagnosis and/or treatment for a patient to receive.

(i) Attenuated latent inhibition and working memory deficit: Indicative of high-transition risk with potentially increased likelihood in responsiveness to dopaminergic-based anti-psychotic drug treatments, e.g., dopamine antagonists, latent inhibition score indicates there is a convergence/emergence of psychosis, a hyper-dopaminergic dysfunction underlay the symptoms of psychosis. Additional finding of working memory deficit confirms cognitive deficit that could start to affect functional outcome if untreated. Recommend treating with a dopaminergic-based anti-psychotic drug and a pro-cognitive drug.

(ii) Enhanced latent inhibition and working memory deficit: Indicative of high-transition risk with potentially increased likelihood of being non-responsive to dopaminergic-based anti-psychotic drug treatments because latent inhibition score indicates cognitive/negative symptoms and a non-dopaminergic dysfunction underlay symptoms of psychosis and cognitive impairment. Additional finding of working memory deficit confirms cognitive deficit that could start to affect functional outcome if untreated. Recommend treating with a pro-cognitive drug therapy due to a working memory deficit and likely responesivness to non-dopaminergic-based drug treatments and increased likelihood of resistance to dopaminergic-based anti-psychotic drug treatments in order to as prevent further cognitive decline and emergence of psychosis.

(iii) In cases where latent inhibition is either attenuated, enhanced or normal but working memory shows no deficit, individuals should be monitored instead of immediately treated with a drug therapy. A treatment recommendation can be made based on the range of normality on the non-deficit task.

Example 5

Latent Inhibition Assay for First-Episode Psychosis (FEP) and Prediction of Antipsychotic Treatment-Response These patients have experienced their first psychotic episode and are antipsychotic-naïve or have minimum exposure to antipsychotic treatment (or alternative therapy). These patients are generally classified as FEP within the first three years from illness onset and up to a third of patients do not respond effectively to currently available anti-psychotic drug treatments or other psychosocial therapies which may be because they have an alternative, non-dopaminergic, neurobiology underlying their psychotic state. Similar to the UHR population, latent inhibition will be used as a cognitive biomarker to prospectively stratify patients and identify those most likely to respond to anti-psychotic medication (or alternative therapy) aimed at ameliorating or improving currently experienced clinical symptoms.

(i) Attenuated latent inhibition: Indicative of an individual with increased likelihood of being responsive to dopaminergic-based anti-psychotic drug treatments, e.g., dopamine antagonists, because latent inhibition score indicates there is a hyper-dopaminergic dysfunction underlay the symptoms of psychosis. Recommend treating with a dopaminergic-based anti-psychotic drug.

(ii) Enhanced latent inhibition: Indicative of an individual with increased likelihood of being non-responsive to dopaminergic-based anti-psychotic drug treatments because latent inhibition score indicates cognitive/negative symptoms, a non-dopaminergic dysfunction underlay symptoms of psychosis and cognitive impairment. Recommend fast-track implementation of clozapine treatment or an alternative drug for treatment-resistant psychotic symptoms with a pro-cognitive drug therapy due to increased likelihood of resistance to dopaminergic-based anti-psychotic drug treatments.

(iii) Normal latent inhibition: Indicative of management of positive symptoms of psychosis in individual and cognitive/negative symptoms that are minimal. Recommend maintenance of current treatment regime with monitoring.

Example 6

Working Memory Latent Inhibition Assay for First-Episode Psychosis (FEP) and Prediction of Antipsychotic Treatment-Response Same use case as above with the addition of working memory assessment during the pre-exposure phase of the latent inhibition task (Working Memory Latent Inhibition; WMLI). An assessment of working memory has the additional benefit of being able to determine whether an individual is experiencing a deficit to their working memory in addition to demonstrating a dysfunction of attentional gating though latent inhibition. Individuals that flag up as having a deficit in both latent inhibition and working memory will increase confidence and provide additional information regarding the optimal diagnosis and/or treatment for a patient to receive.

(i) Attenuated latent inhibition and working memory deficit: Indicative of an individual with increased likelihood of being responsive to dopaminergic-based antipsychotic drug treatments, e.g., dopamine antagonists, because latent inhibition score indicates there is a hyper-dopaminergic dysfunction underlay of the symptoms of psychosis. Additional finding of working memory deficit confirms cognitive deficit that could start to affect functional outcome if untreated. Recommend treating with a dopaminergic-based anti-psychotic drug and a pro-cognitive drug.

(ii) Enhanced latent inhibition and working memory deficit: Indicative of an individual with increased likelihood of being non-responsive to dopaminergic-based anti-psychotic drug treatments because latent inhibition score indicates cognitive/negative symptoms, a non-dopaminergic dysfunction underlay symptoms of psychosis and cognitive impairment. Additional finding of working memory deficit confirms cognitive deficit that could start to affect functional outcome if untreated. Recommend fast-track implementation of clozapine treatment or an alternative drug for treatment-resistant psychotic symptoms with a pro-cognitive drug therapy due to a working memory deficit and likely responsiveness to non-dopaminergic-based drug treatments and increased likelihood of resistance to dopaminergic-based anti-psychotic drug treatments.

(iii) Normal latent inhibition and working memory deficit: Indicative of management of positive symptoms of psychosis in individual but working memory deficit indicates cognitive impairment. Recommend maintenance of current treatment regime for psychosis with additional pro-cognitive drug therapy due to a working memory deficit to minimize impairment to functional outcome and day-to-day life.

(iv) In other cases where only latent inhibition or working memory are abnormal treatment recommendation for an individual is made based on the range of normality on the non-deficit task.

Example 7

Latent Inhibition Assay to Direct Treatment of Chronic Treatment Responsive Schizophrenia These are patients that show good response to antipsychotic treatment, with illness duration approximately over 3 years. Patients with good response have mild or no psychotic symptoms. However, they can exhibit high negative symptoms and severe cognitive dysfunction, that, if sustained over long periods of time, increases their risk of relapse and impairs functional outcome and day-to-day life. These cognitive and negative symptoms can be very heterogeneous amongst patients. Latent inhibition will be used as a cognitive biomarker to determine whether psychotic symptoms are under control and to identify those patients that are experiencing sufficient cognitive deficit that would warrant treatment. Latent inhibition scores will be used to determine which treatments patients will be most likely to respond to.

(i) Attenuated latent inhibition: Indicative of an individual with increased likelihood of being responsive to dopaminergic-based anti-psychotic drug treatments, e.g., dopamine antagonists, because latent inhibition score indicates a hyper-dopaminergic dysfunction underlay the symptoms of psychosis. Recommend treating with a dopaminergic-based anti-psychotic drug and pro-cognitive drug to control cognitive symptoms. Monitor for non-adherence and consider dosage of anti-psychotic drug as attenuation not expected in this group if psychosis is seemingly stable.

(ii) Enhanced latent inhibition: Indicative of an individual being somewhat responsive to dopaminergic-based anti-psychotic drug treatments because latent inhibition score indicates management of positive symptoms but cognitive/negative symptoms are prominent. Recommend continued treatment a dopaminergic-based anti-psychotic drug with additional pro-cognitive drug to control cognitive symptoms.

(iii) Normal latent inhibition: Indicative of management of positive symptoms of psychosis in individual and cognitive/negative symptoms that are minimal. Recommend maintenance of current treatment regime with monitoring.

Example 8

Working Memory Latent Inhibition Assay to Direct Treatment of Chronic Treatment Responsive Schizophrenia Same use case as above with the addition of working memory assessment during the pre-exposure phase of the latent inhibition task (Working Memory Latent Inhibition; WMLI). An assessment of working memory has the additional benefit of being able to determine whether an individual is experiencing a deficit to their working memory in addition to demonstrating a dysfunction of attentional gating though latent inhibition. Individuals that flag up as having a deficit in both latent inhibition and working memory will increase confidence and provide additional information regarding the optimal diagnosis and/or treatment for a patient to receive.

(i) Attenuated latent inhibition and working memory deficit: Indicative of an individual with increased likelihood of being responsive to dopaminergic-based anti-psychotic drug treatments, e.g., dopamine antagonists, because latent inhibition score indicates a hyper-dopaminergic dysfunction underlay the symptoms of psychosis. Additional finding of working memory deficit confirms presence of a cognitive deficit that could start to affect functional outcome if untreated. Recommend treating with a dopaminergic-based anti-psychotic drug and a pro-cognitive drug to control cognitive symptoms. Monitor for non-adherence and consider dosage of anti-psychotic drug as attenuation not expected in this group if psychosis is seemingly stable.

(ii) Enhanced latent inhibition and working memory deficit: Indicative of an individual being somewhat responsive to dopaminergic-based anti-psychotic drug treatments because latent inhibition score indicates management of positive symptoms but cognitive/negative symptoms are prominent. Additional finding of working memory deficit confirms presence of a cognitive deficit that could start to affect functional outcome if untreated. Recommend treating with a dopaminergic-based anti-psychotic drug with additional pro-cognitive drug to control negative/cognitive symptoms.

(iii) Normal latent inhibition and working memory deficit: Indicative of management of positive symptoms of psychosis in individual but working memory deficit confirms cognitive impairment. Recommend maintenance of current treatment regime for psychosis with additional pro-cognitive drug therapy due to a working memory deficit to minimize impairment to functional outcome and day-to-day life.

(iv) In other cases where only latent inhibition or working memory are abnormal treatment recommendation for an individual is made based on the range of normality on the non-deficit task.

Example 9

Latent Inhibition Assay for Chronic Treatment-Resistant Schizophrenia (TRS)

One-third of schizophrenia patients do not respond to anti-psychotic drugs. The longer patients are left without treatment during a psychotic episode, the less responsive they continue to become to treatment and are thus more difficult to treat. TRS patients have a different neurobiological profile: rather than being hyper-dopaminergic, they have normal dopaminergic levels but may have low levels of glutamate/acetylcholine. Currently, the only effective drug for patients who are treatment resistant to APD's is clozapine but this drug does have some unpleasant side effects and so more tolerable drugs for patients are desirable (and are in development). Attenuated latent inhibition is a predictor of hyper-dopaminergic activity, whereas enhanced latent inhibition is a predictor of normo-dopaminergic/glutamatergic activity and as such latent inhibition can be used to diagnose/identify and subsequently treat TRS vs non-TRS patients. Latent inhibition can be used as way to pre-select patients, and thus effectively treat those, who flag us as being phenotypically treatment resistant.

(i) Attenuated latent inhibition: Indicative of an individual somewhat non-responsive (i.e., treatment resistance) to dopaminergic-based anti-psychotic drug treatments, e.g., dopamine antagonists, because latent inhibition score indicates anti-psychotic drug treatment-resistance due to non-biological underpinnings (e.g. medication non-compliance, recreational drug abuse, other substance abuse). Recommend treating with a dopaminergic-based anti-psychotic drug with additional pro-cognitive drug to control cognitive symptoms and enhance treatment efficacy. Monitor for non-adherence and consider dosage modification of anti-psychotic drug as attenuation not expected in this group if psychosis is seemingly stable.

(ii) Enhanced latent inhibition: Indicative of an individual being unresponsive to dopaminergic-based anti-psychotic drug treatments because latent inhibition score indicates cognitive/negative symptoms and a non-dopaminergic dysfunction underlay symptoms of psychosis and cognitive impairment. Recommend fast-track implementation of clozapine treatment or an alternative drug for treatment-resistant psychotic symptoms with a pro-cognitive drug therapy and likely responesivness to non-dopaminergic-based drug treatments and increased likelihood of resistance to dopaminergic-based anti-psychotic drug treatments.

(iii) Normal latent inhibition: Indicative of management of positive symptoms of psychosis in individual and cognitive/negative symptoms that are minimal. Recommend maintenance of current treatment regime with monitoring. If range of normality is extreme, consider clozapine or an alternative drug for treatment-resistant psychotic symptoms and pro-cognitive drug for symptom reduction.

Example 10

Working Memory Latent Inhibition Assay for Chronic Treatment-Resistant Schizophrenia (TRS)

Same use case as above with the addition of working memory assessment during the pre-exposure phase of the latent inhibition task (Working Memory Latent Inhibition; WMLI). An assessment of working memory has the additional benefit of being able to determine whether an individual is experiencing a deficit to their working memory in addition to demonstrating a dysfunction of attentional gating though latent inhibition. Individuals that flag up as having a deficit in both latent inhibition and working memory will increase confidence and provide additional information regarding the optimal diagnosis and/or treatment for a patient to receive.

(i) Attenuated latent inhibition and working memory deficit: Indicative of an individual somewhat non-responsive (i.e., treatment resistant) to dopaminergic-based anti-psychotic drug treatments, e.g., dopamine antagonists, because latent inhibition score indicates anti-psychotic drug treatment-resistance due to non-biological underpinnings (e.g. medication non-compliance, recreational drug abuse, other substance abuse). Additional finding of working memory deficit confirms cognitive deficit that could start to affect functional outcome if untreated. Recommend treating with a dopaminergic-based anti-psychotic drug with additional pro-cognitive drug to ameliorate cognitive symptoms and enhance treatment efficacy. Monitor for non-adherence and consider dosage modification of anti-psychotic drug as attenuation not expected in this group if psychosis is seemingly stable.

(ii) Enhanced latent inhibition and working memory deficit: Indicative of an individual being unresponsive to dopaminergic-based anti-psychotic drug treatments because latent inhibition score indicates cognitive/negative symptoms and a non-dopaminergic dysfunction underlay symptoms of psychosis and cognitive impairment. Additional finding of working memory deficit confirms cognitive deficit that could start to affect functional outcome if untreated. Recommend fast-track implementation of clozapine treatment or an alternative drug for treatment-resistant psychotic symptoms with additional pro-cognitive drug therapy to ameliorate cognitive and negative symptoms and enhance efficacy of clozapine treatment or an alternative drug for treatment-resistant psychotic symptoms.

(iii) Normal latent inhibition and working memory deficit: Indicative of management of positive symptoms of psychosis in individual but working memory deficit indicates cognitive impairment. Recommend maintenance of current treatment regime for psychosis with additional pro-cognitive drug therapy due to a working memory deficit to minimize impairment to functional outcome and day-to-day life.

(iv) In other cases where only latent inhibition or working memory are abnormal, treatment recommendation for an individual is made based on the range of normality on the non-deficit task.

Example 11

Latent Inhibition Assay in APD Antipsychotic Drug Action

Antipsychotic trials currently rely on the Positive and Negative Syndrome Scale (PANSS) assessment as a primary outcome and/or subjective way to determine the efficacy of a drug for improving symptomatology. Assessment of latent inhibition will be used as an objective way to measure responsiveness to treatment.

(i) Attenuated latent inhibition: Indicative of an individual who is experiencing psychosis with an increased likelihood of being responsive to dopaminergic-based antipsychotic drug treatments. If attenuation of latent inhibition remains through the course of an anti-psychotic trial then the compound in question may be deemed ineffective for remediating psychosis or the dosage may need increasing.

(ii) Enhanced latent inhibition: Indicative of an individual who has responded to the APD if latent inhibition was previously attenuated and the dose of the APD may require decreasing to attain normal latent inhibition. If latent inhibition was enhanced from the start of the trial, then this is indicative of an individual with an increased likelihood of being unresponsive to dopaminergic-based anti-psychotic drug treatments because latent inhibition score indicates a non-dopaminergic dysfunction underlay symptoms of psychosis and cognitive impairment. In this instance this patient would be deemed a non-responder to the compound in question.

(iii) Normal latent inhibition: Indicative of management of positive symptoms of psychosis in individual and cognitive/negative symptoms that are minimal. If this score was previously an attenuated or enhanced latent inhibition, the compound may be considered effective.

(iv) No change in latent inhibition score from initial assessment mat be considered as a non-response to the treatment.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended embodiments and embodiments hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the embodiments appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and embodimented individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended embodiments.

Unless otherwise indicated, all numbers expressing a characteristic, item, quantity, parameter, property, term, and so forth used in the present specification and embodiments are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached embodiments are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the embodiments, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the embodimented subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following embodiments) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise embodimented. No language in the present specification should be construed as indicating any non-embodimented element essential to the practice of the invention.

When used in the embodiments, whether as filed or added per amendment, the open-ended transitional term "comprising", variations thereof such as "comprise" and "comprises", and equivalent open-ended transitional phrases thereof like "including," "containing" and "having", encompasses all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the embodiment. Specific embodiments disclosed herein may be further limited in the embodiments using the closed-ended transitional phrases "consisting of" or "consisting essentially of" (or variations thereof such as "consist of", "consists of", "consist essentially of", and "consists essentially of") in lieu of or as an amendment for "comprising." When used in the embodiments, whether as filed or added per amendment, the closed-ended transitional phrase "consisting of" excludes any element, limitation, step, integer, or feature not expressly recited in the embodiments. The closed-ended transitional phrase "consisting essentially of" limits the scope of a embodiment to the expressly recited elements, limitations, steps, integers, and/or features and any other elements, limitations, steps, integers, and/or features that do not materially affect the basic and novel characteristic(s) of the embodimented subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the embodiment whereas the meaning of the closed-ended transitional phrase "consisting essentially of" is being defined as only including those elements, limitations, steps, integers, and/or features specifically recited in the embodiment and those elements, limitations, steps, integers, and/or features that do not materially affect the basic and novel characteristic(s) of the embodimented subject matter. Therefore, the open-ended transitional phrase "comprising" (and equivalent open-ended transitional phrases thereof) includes within its meaning, as a limiting case, embodimented subject matter specified by the closed-ended transitional phrases "consisting of" or "consisting essentially of." As such embodiments described herein or so embodimented with the phrase "comprising" are expressly or inherently unambiguously described, enabled and supported herein for the phrases "consisting essentially of" and "consisting of."

All patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents is based on the information available to the applicant and does not constitute any admission as to the correctness of the dates or contents of these documents.

Lastly, the terminology used herein is for the purpose of describing particular embodiments only, and is not intended to limit the scope of the present invention, which is defined solely by the embodiments. Accordingly, the present invention is not limited to that precisely as shown and described.

The invention claimed is:

1. A method of treating an individual subjected to a non-invasive computational device-based test for latent inhibition assessment, comprising:
   a. having the individual perform a latent inhibition assessment using the computational device and a graphical user interface coupled thereto, the latent inhibition assessment comprising a pre-exposure phase and a test phase,
      i. wherein the pre-exposure phase comprises,
         presenting the individual with a first set of directions for how to respond to each stimulus of a first group of stimuli, wherein the first set of directions include pre-exposure phase instructions which require the individual to respond to each stimulus of the first group of stimuli in a defined manner;
         presenting the individual with a random order of the first group of stimuli, each stimulus being presented for a presentation time between 10 msec to 10,000 msec, wherein the first group of stimuli comprises a plurality of stimuli including at least one preexposed stimulus and one or more neutral stimuli, wherein the at least one preexposed stimulus is a pre-target stimulus;
      ii. wherein the test phase comprises,
         presenting the individual with a second set of directions for how to respond to each stimulus of a second group of stimuli, wherein the second set of directions include test phase instructions which require the individual to anticipate the occurrence of a target stimulus; presenting the individual with the second group of stimuli, each stimulus being presented for the presentation time between 10 msec to 10,000 msec, wherein the second group of stimuli comprises a plurality of stimuli including the at least one preexposed stimuli, a non-preexposed stimulus, the target stimulus, and the one or more neutral stimuli, wherein the non-preexposed stimulus is a pre-target stimulus that was not shown during the pre-exposure phase;

recording and analyzing the individual's interaction with the graphical user interface following presentation of each stimulus from the second group of stimuli by measuring a response time associated with each stimulus from the plurality of stimuli to determine a target anticipated response, wherein an anticipatory response to the target stimulus of less than the sum of the presentation time and interval time according to the second set of directions is indicative that the individual anticipated the occurrence of the target stimulus, and wherein an anticipatory response to the target stimulus of equal to or more than the sum of the presentation time and interval time according to the second set of directions is indicative that the individual failed to anticipate the occurrence of the target stimulus;

b. measuring a latent inhibition response of the individual by calculating a latent inhibition score by modeling each target anticipated response in one or more statistical analyses within a computing environment in which a plurality of data processing components are executed in conjunction with at least one specifically configured processor, the one or more statistical analyses comprising:
  i. determining one or more reaction times associated with each target stimulus from the plurality of stimuli,
  ii. determining a number of anticipatory responses indicative that the individual anticipated the occurrence of the target stimulus,
  iii. determining a number of anticipatory responses indicative that the individual failed to anticipate the occurrence of the target stimulus,
  iv. determining a percentage of anticipatory responses indicative that the individual anticipated the occurrence of the target stimulus,
  v. determining a percentage of anticipatory responses indicative that the individual failed to anticipate the occurrence of the target stimulus, or
  vi. determining an accuracy sensitivity d',
  wherein the calculated latent inhibition score is used to classify whether the individual exhibited an attenuated latent inhibition response, a normal latent inhibition response or an enhanced latent inhibition response from the latent inhibition score; and c. treating the individual, wherein the treating comprises at least one of:
  i. calculating the attenuated latent inhibition response in step (b) and treating the individual with an antipsychotic drug; or
  ii. calculating the enhanced latent inhibition response in step (b) and treating the individual with a procognitive drug.

2. The method of claim 1, wherein in step (b)
i. the latent inhibition score is calculated by
  calculating a first average time based on the target anticipated response measured for each presentation of the target stimulus presented after presentation of the at least one non-preexposed stimulus;
  calculating a second average time based on the target anticipated response measured for each presentation of the target stimulus presented after presentation of the at least one preexposed stimulus; and
  calculating the latent inhibition score by (a) subtracting the second average time by the first average time or (b) subtracting the first average time by the second average time; or ii. the latent inhibition score is calculated by
  calculating a first average time based on the target anticipated response measured for each presentation of the target stimulus presented after presentation of the at least one non-preexposed stimulus;
  calculating a second average time based on the target anticipated response measured for each presentation of the target stimulus presented after presentation of the at least one preexposed stimulus; and
  calculating the latent inhibition score by determining whether the first average time is slower or faster than the second average time; or iii. the latent inhibition score is calculated by
  pairing the target anticipated response time based on the at least one non-preexposed stimulus with the target anticipated response time based on the at least one preexposed stimulus;
  calculating whether the target anticipated response time based on the at least one non-preexposed stimulus of the pairing was faster relative to the target anticipated response time based on the at least one preexposed stimulus of the pairing; and
  calculating the latent inhibition score by determining (a) the total number of pairings that were higher for the target anticipated response time based on the non-preexposed stimulus relative to the target anticipated response time based on the preexposed stimulus, (b) the total number of pairings that were lower for the target anticipated response time based on the non-preexposed stimulus relative to the target anticipated response time based on the preexposed stimulus, or (c) both (a) and (b); or iv. the latent inhibition score is calculated by
  calculating a first average number of anticipatory responses based on the target anticipated response measured for each presentation of the target stimulus presented after presentation of the at least one non-preexposed stimulus;
  calculating a second average number of anticipatory responses based on target anticipated response measured for each presentation of the target stimulus presented after presentation of the at least one preexposed stimulus; and
  calculating the latent inhibition score by (a) subtracting the second average number of anticipatory responses by the first average number of anticipatory responses or (b) subtracting the first average number of anticipatory responses by the second average number of anticipatory responses; or v. the latent inhibition score is calculated by
  calculating a first average number of anticipatory responses based on the target anticipated response measured for each presentation of the target stimulus presented after presentation of the at least one non-preexposed stimulus;
  calculating a second average number of anticipatory responses based on the target anticipated response measured for each presentation of the target stimulus presented after presentation of the at least one preexposed stimulus; and
  calculating the latent inhibition score by determining whether the first average number of anticipatory responses is lower or higher than the second average number of anticipatory responses; or vi. the latent inhibition score is calculated by
pairing the target anticipated response based on the at least one non-preexposed stimulus with the target anticipated response based on the at least one pre-exposed stimulus;
calculating whether the target anticipated response based on the at least one non-preexposed stimulus of the pairing was faster relative to the target anticipated response based on the at least one preexposed stimulus of the pairing; and
calculating the latent inhibition score by determining (a) the total number of pairings that were higher for the target anticipated response based on the non-preexposed stimulus relative to the target anticipated response based on the preexposed stimulus, (b) the total number of pairings that were lower for the target anticipated response based on the non-preexposed stimulus relative to the target anticipated response based on the preexposed stimulus, or (c) both (a) and (b); or vii. the latent inhibition score is calculated by
calculating a first percent of anticipatory responses based on the target anticipated response measured for each presentation of the target stimulus presented after presentation of the at least one non-preexposed stimulus;
calculating a second percent of anticipatory responses based on the target anticipated response measured for each presentation of the target stimulus presented after presentation of the at least one preexposed stimulus; and
calculating the latent inhibition score by (a) subtracting the second percent of anticipatory responses by the first percent of anticipatory responses; or (b) subtracting the first percent of anticipatory responses by the second percent of anticipatory responses; or viii. the latent inhibition score is calculated by
calculating a first d' score of anticipatory responses based on the target anticipated response measured for each presentation of the target stimulus presented after presentation of the at least one non-preexposed stimulus;
calculating a second d' score of anticipatory responses based on the target anticipated response measured for each of the target stimulus presented after presentation of the at least one preexposed stimulus; and
calculating the latent inhibition score by subtracting the second d' score of anticipatory responses by the first d' score of anticipatory responses.

3. The method of claim 2, wherein in step (b) the measuring a latent inhibition response of the individual to calculate a latent inhibition score further comprises comparing the latent inhibition score to a reference score comprising a standard range of latent inhibition scores.

4. The method of claim 1, wherein step (a)(i) further comprises measuring a response of the individual to each stimulus from the first group of stimuli.

5. The method of claim 1, further comprising evaluating working memory.

6. The method of claim 1, wherein the presenting the individual with the random order of the first group of stimuli further comprises an interval time between each stimulus of 1 msec to 10,000 msec; and
the presenting the individual with the second group of stimuli further comprises the interval time between each stimulus of 1 msec to 10,000 msec.

7. The method of claim 1, wherein the anti-psychotic drug comprises Chlorpromazine, Haloperidol, Loxapine, Perphenazine, Prochlorperazine, Thiothixene, Thioridazine, Trifluoperazine, Olanzapine, Paliperidone, Quetiapine, Risperidone, or Aripiprazole; and
the pro-cognitive drug is an agonist, an antagonist, a partial agonist, a positive allosteric modulator, a negative allosteric modulator, a silent allosteric modulator, or an inverse agonist of an ionotropic receptor, a metabotropic receptor, or a phosphodiesterase (PDE).

8. The method of claim 1, comprising treating the individual with the anti-psychotic drug, wherein the anti-psychotic drug comprises Chlorpromazine, Haloperidol, Loxapine, Perphenazine, Prochlorperazine, Thiothixene, Thioridazine, Trifluoperazine, Olanzapine, Paliperidone, Quetiapine, Risperidone, or Aripiprazole.

9. The method of claim 1, comprising treating the individual with the pro-cognitive drug, wherein the pro-cognitive drug is an agonist, an antagonist, a partial agonist, a positive allosteric modulator, a negative allosteric modulator, a silent allosteric modulator, or an inverse agonist of an ionotropic receptor, a metabotropic receptor, or a phosphodiesterase (PDE).

10. A method of treating an individual subjected to a non-invasive computational device-based test for latent inhibition assessment, comprising:
a. having the individual perform a latent inhibition assessment using the computational device and a graphical user interface coupled thereto, the latent inhibition assessment comprising a pre-exposure phase and a test phase,
i. wherein the pre-exposure phase comprises,
presenting the individual with a first set of directions for how to respond to each stimulus of a first group of stimuli, wherein the first set of directions include pre-exposure phase instructions which require the individual to respond to each stimulus of the first group of stimuli in a defined manner;
presenting the individual with a random order of the first group of stimuli, each stimulus being presented for a presentation time between 10 msec to 10,000 msec, wherein the first group of stimuli comprises a plurality of stimuli including at least one preexposed stimulus and one or more neutral stimuli, wherein the at least one preexposed stimulus is a pre-target stimulus;
ii. wherein the test phase comprises,
presenting the individual with a second set of directions for how to respond to each stimulus of a second group of stimuli, wherein the second set of directions include test phase instructions which require the individual to anticipate the occurrence of a target stimulus; presenting the individual with the second group of stimuli, each stimulus being presented for the presentation time between 10 msec to 10,000 msec, wherein the second group of stimuli comprises a plurality of stimuli including the at least one preexposed stimuli, a non-preexposed stimulus, the target stimulus, and the one or more neutral stimuli, wherein the non-preexposed stimulus is a pre-target stimulus that was not shown during the pre-exposure phase;
recording and analyzing the individual's interaction with the graphical user interface following presentation of each stimulus from the second group of stimuli by measuring a response time associated with each stimulus from the plurality of stimuli to determine a target anticipated response, wherein an anticipatory response to the target stimulus of less than the sum of the presentation time and interval time according to the second set of directions is indicative that the individual anticipated the occurrence of the target stimulus, and wherein an anticipatory response to the target stimulus of equal to or more than the sum of the presentation time and interval time according to the second set of directions is indicative that the individual failed to anticipate the occurrence of the target stimulus;

b. measuring a latent inhibition response of the individual by calculating a latent inhibition score by modeling each target anticipated response in one or more statistical analyses within a computing environment in which a plurality of data processing components are executed in conjunction with at least one specifically configured processor, the one or more statistical analyses comprising:
 i. determining one or more reaction times associated with each target stimulus from the plurality of stimuli,
 ii. determining a number of anticipatory responses indicative that the individual anticipated the occurrence of the target stimulus,
 iii. determining a number of anticipatory responses indicative that the individual failed to anticipate the occurrence of the target stimulus,
 iv. determining a percentage of anticipatory responses indicative that the individual anticipated the occurrence of the target stimulus,
 v. determining a percentage of anticipatory responses indicative that the individual failed to anticipate the occurrence of the target stimulus, or
 vi. determining an accuracy sensitivity d',
 wherein the calculated latent inhibition score is used to classify whether the individual exhibited an attenuated latent inhibition response, a normal latent inhibition response or an enhanced latent inhibition response from the latent inhibition score;

c. evaluating working memory, wherein the evaluating working memory comprises classifying whether the individual exhibited a working memory deficit or no working memory deficit;

d. treating the individual, wherein the treating comprises at least one of:
 i. calculating the attenuated latent inhibition response in step (b), classifying the individual as exhibiting the working memory deficit in step (c), and treating the individual with an anti-psychotic and a pro-cognitive drug;
 ii. calculating the normal latent inhibition response in step (b), classifying the individual as exhibiting the working memory deficit in step (c), and treating the individual with a pro-cognitive drug; or
 iii. calculating the enhanced latent inhibition response in step (b), classifying the individual as exhibiting the working memory deficit in step (c), and treating the individual with a pro-cognitive drug.

11. The method of claim 10, further comprising:
providing instructions in the pre-exposure phase which require the individual to respond to a current stimulus of the first group of stimuli only if the current stimulus is the same as a stimulus shown one position back in a sequence of the first group of stimuli; or
providing instructions in the pre-exposure phase which require the individual to respond to a current stimulus of the first group of stimuli only if the current stimulus is the same as a stimulus shown two positions back in a sequence of the first group of stimuli.

12. The method of claim 11, wherein the percent of pre-exposure responses selected correctly by the individual is used to classify whether the individual exhibited the working memory deficit or the no working memory deficit.

13. The method of claim 12, wherein the classifying whether the individual exhibited the working memory deficit or the no working memory deficit comprises:
 classifying the individual as exhibiting the working memory deficit when less than 50% of the pre-exposure one position back or two position back responses were selected correctly; or
 classifying the individual as exhibiting the no working memory deficit when 50% or more of the pre-exposure one position back or two position back responses were selected correctly.

14. The method of claim 11, wherein evaluating working memory comprises:
 counting the number of pre-exposure responses presented based on the pre-exposure one position back or two position back stimulus;
 counting the number of pre-exposure responses selected correctly by the individual based on the pre-exposure one position back or two position back stimulus; and
 calculating the percent of pre-exposure responses selected correctly by the individual, wherein 50% or more is indicative of no working memory deficit.

15. The method of claim 11, wherein evaluating working memory comprises:
 counting the number of pre-exposure responses selected incorrectly by the individual based on the pre-exposure one position back or two position back stimulus; and
 calculating the percent of pre-exposure responses selected incorrectly by the individual, wherein 50% or more is indicative of impaired working memory.

16. The method of claim 10, wherein evaluating working memory comprises calculating the average reaction time of pre-exposure responses selected incorrectly by the individual.

17. The method of claim 10, wherein in step (b):
 i. the latent inhibition score is calculated by
  calculating a first average time based on the target anticipated response measured for each presentation of the target stimulus presented after presentation of the at least one non-preexposed stimulus;
  calculating a second average time based on the target anticipated response measured for each presentation of the target stimulus presented after presentation of the at least one preexposed stimulus; and
  calculating the latent inhibition score by (a) subtracting the second average time by the first average time or (b) subtracting the first average time by the second average time; or
 ii. the latent inhibition score is calculated by
  calculating a first average time based on the target anticipated response measured for each presentation of the target stimulus presented after presentation of the at least one non-preexposed stimulus;
  calculating a second average time based on the target anticipated response measured for each presentation of the target stimulus presented after presentation of the at least one preexposed stimulus; and calculating the latent inhibition score by determining whether the first average time is slower or faster than the second average time; or iii. the latent inhibition score is calculated by pairing the target anticipated response time based on the at least one non-preexposed stimulus with the target anticipated response time based on the at least one preexposed stimulus;

calculating whether the target anticipated response time based on the at least one non-preexposed stimulus of the pairing was faster relative to the target anticipated response time based on the at least one pre-exposed stimulus of the pairing; and calculating the latent inhibition score by determining (a) the total number of pairings that were higher for the target anticipated response time based on the non-preexposed stimulus relative to the target anticipated response time based on the preexposed stimulus, (b) the total number of pairings that were lower for the target anticipated response time based on the non-preexposed stimulus relative to the target anticipated response time based on the preexposed stimulus, or (c) both (a) and (b); or iv. the latent inhibition score is calculated by calculating a first average number of anticipatory responses based on the target anticipated response measured for each presentation of the target stimulus presented after presentation of the at least one non-preexposed stimulus;

calculating a second average number of anticipatory responses based on target anticipated response measured for each presentation of the target stimulus presented after presentation of the at least one pre-exposed stimulus; and calculating the latent inhibition score by (a) subtracting the second average number of anticipatory responses by the first average number of anticipatory responses or (b) subtracting the first average number of anticipatory responses by the second average number of anticipatory responses; or v. the latent inhibition score is calculated by calculating a first average number of anticipatory responses based on the target anticipated response measured for each presentation of the target stimulus presented after presentation of the at least one non-preexposed stimulus;

calculating a second average number of anticipatory responses based on the target anticipated response measured for each presentation of the target stimulus presented after presentation of the at least one pre-exposed stimulus; and calculating the latent inhibition score by determining whether the first average number of anticipatory responses is lower or higher than the second average number of anticipatory responses; or vi. the latent inhibition score is calculated by pairing the target anticipated response based on the at least one non-preexposed stimulus with the target anticipated response based on the at least one pre-exposed stimulus;

calculating whether the target anticipated response based on the at least one non-preexposed stimulus of the pairing was faster relative to the target anticipated response based on the at least one preexposed stimulus of the pairing; and calculating the latent inhibition score by determining (a) the total number of pairings that were higher for the target anticipated response based on the non-preexposed stimulus relative to the target anticipated response based on the preexposed stimulus, (b) the total number of pairings that were lower for the target anticipated response based on the non-preexposed stimulus relative to the target anticipated response based on the preexposed stimulus, or (c) both (a) and (b); or vii. the latent inhibition score is calculated by calculating a first percent of anticipatory responses based on the target anticipated response measured for each presentation of the target stimulus presented after presentation of the at least one non-preexposed stimulus;

calculating a second percent of anticipatory responses based on the target anticipated response measured for each presentation of the target stimulus presented after presentation of the at least one preexposed stimulus; and calculating the latent inhibition score by (a) subtracting the second percent of anticipatory responses by the first percent of anticipatory responses; or (b) subtracting the first percent of anticipatory responses by the second percent of anticipatory responses; or viii. the latent inhibition score is calculated by calculating a first d' score of anticipatory responses based on the target anticipated response measured for each presentation of the target stimulus presented after presentation of the at least one non-preexposed stimulus;

calculating a second d' score of anticipatory responses based on the target anticipated response measured for each of the target stimulus presented after presentation of the at least one preexposed stimulus; and calculating the latent inhibition score by subtracting the second d' score of anticipatory responses by the first d' score of anticipatory responses.

18. The method of claim 17, wherein in step (b) the measuring a latent inhibition response of the individual to calculate a latent inhibition score further comprises comparing the latent inhibition score to a reference score comprising a standard range of latent inhibition scores.

19. The method of claim 10, wherein step (a)(i) further comprises measuring a response of the individual to each stimulus from the first group of stimuli.

20. The method of claim 10, wherein the presenting the individual with the random order of the first group of stimuli further comprises an interval time between each stimulus of 1 msec to 10,000 msec; and the presenting the individual with the second group of stimuli further comprises an interval time between each stimulus of 1 msec to 10,000 msec.

21. The method of claim 10, wherein the anti-psychotic drug comprises Chlorpromazine, Haloperidol, Loxapine, Perphenazine, Prochlorperazine, Thiothixene, Thioridazine, Trifluoperazine, Olanzapine, Paliperidone, Quetiapine, Risperidone, or Aripiprazole; and the pro-cognitive drug is an agonist, an antagonist, a partial agonist, a positive allosteric modulator, a negative allosteric modulator, a silent allosteric modulator, or an inverse agonist of an ionotropic receptor, a metabotropic receptor, or a phosphodiesterase (PDE).

22. The method of claim 10, comprising treating the individual with the anti-psychotic drug, wherein the anti-psychotic drug comprises Chlorpromazine, Haloperidol, Loxapine, Perphenazine, Prochlorperazine, Thiothixene, Thioridazine, Trifluoperazine, Olanzapine, Paliperidone, Quetiapine, Risperidone, or Aripiprazole.

23. The method of claim 10, comprising treating the individual with the pro-cognitive drug, wherein the pro-cognitive drug is an agonist, an antagonist, a partial agonist, a positive allosteric modulator, a negative allosteric modulator, a silent allosteric modulator, or an inverse agonist of an ionotropic receptor, a metabotropic receptor, or a phosphodiesterase (PDE).

24. The method of claim 11, wherein evaluating working memory comprises calculating a d' score of pre-exposure responses presented based on the pre-exposure one position back or two position back stimulus.

* * * * *